United States Patent
Fordham

(10) Patent No.: US 11,789,014 B2
(45) Date of Patent: Oct. 17, 2023

(54) METHOD OF DETERMINING THE PRESENCE OR ABSENCE OF A TARGET ANALYTE COMPRISING USING A REPORTER POLYNUCLEOTIDE AND A TRANSMEMBRANE PORE

(71) Applicant: Oxford Nanopore Technologies PLC, Oxford (GB)

(72) Inventor: Daniel George Fordham, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 354 days.

(21) Appl. No.: 16/610,891

(22) PCT Filed: May 3, 2018

(86) PCT No.: PCT/GB2018/051190
§ 371 (c)(1),
(2) Date: Nov. 4, 2019

(87) PCT Pub. No.: WO2018/203071
PCT Pub. Date: Nov. 8, 2018

(65) Prior Publication Data
US 2021/0148903 A1 May 20, 2021

(30) Foreign Application Priority Data
May 4, 2017 (GB) ...................................... 1707140

(51) Int. Cl.
*G01N 33/543* (2006.01)

(52) U.S. Cl.
CPC .............................. *G01N 33/54306* (2013.01)

(58) Field of Classification Search
CPC ............. G01N 33/52; G01N 33/54306; G01N 33/54366
See application file for complete search history.

(56) References Cited

U.S. PATENT DOCUMENTS

| | | |
|---|---|---|
| 6,465,193 B2 | 10/2002 | Akeson et al. |
| 6,916,665 B2 | 7/2005 | Bayley et al. |
| 8,986,528 B2 | 3/2015 | Denison et al. |
| 10,246,741 B2 | 4/2019 | Clarke |
| 11,098,355 B2 | 8/2021 | Heron et al. |
| 11,466,317 B2 | 10/2022 | Clarke et al. |
| 2002/0197618 A1 | 12/2002 | Sampson |
| 2013/0048499 A1 | 2/2013 | Mayer et al. |
| 2014/0134618 A1 | 5/2014 | Kokoris et al. |
| 2015/0152492 A1* | 6/2015 | Brown ................. C12Q 1/6869 435/6.1 |
| 2015/0275289 A1 | 10/2015 | Otwinowski et al. |
| 2015/0344945 A1 | 12/2015 | Mandell et al. |
| 2016/0041179 A1 | 2/2016 | Ju et al. |
| 2016/0237488 A1 | 8/2016 | Ke et al. |
| 2016/0326578 A1 | 11/2016 | Bielas |
| 2017/0044605 A1 | 2/2017 | Merriman et al. |
| 2019/0352709 A1 | 11/2019 | Clarke et al. |
| 2020/0010887 A1 | 1/2020 | Heron et al. |
| 2021/0363577 A1 | 11/2021 | Clarke et al. |
| 2022/0090192 A1 | 3/2022 | Heron et al. |
| 2023/0084931 A1 | 3/2023 | Clarke et al. |

FOREIGN PATENT DOCUMENTS

| | | |
|---|---|---|
| CN | 1860370 A | 11/2006 |
| CN | 103695530 A | 4/2014 |
| WO | WO 2000/28312 A1 | 5/2000 |
| WO | WO 2000/034527 A2 | 6/2000 |
| WO | WO 2001/042782 A1 | 6/2001 |
| WO | WO 2002/028312 A1 | 4/2002 |
| WO | WO 2005/124888 A1 | 12/2005 |
| WO | WO 2006/100484 A2 | 9/2006 |
| WO | WO 2008/102120 A1 | 8/2008 |
| WO | WO 2008/102121 A1 | 8/2008 |
| WO | WO 2009/035647 A1 | 3/2009 |
| WO | WO 2009/077734 A2 | 6/2009 |
| WO | WO 2010/004265 A1 | 1/2010 |
| WO | WO 2010/004273 A1 | 1/2010 |
| WO | WO 2010/055307 A1 | 5/2010 |

(Continued)

OTHER PUBLICATIONS

Peng et al., "Reverse DNA translocation through a solid-state nanopore by magnetic tweezers," Nanotechnology, 2009, vol. 20, No. 18, pp. 1-8.*
International Search Report and Written Opinion for Application No. PCT/GB2018/051190, dated Jul. 26, 2018.
International Preliminary Report on Patentability for Application No. PCT/GB2018/051190, dated Nov. 14, 2019.
Anderson, The clinical plasma proteome: a survey of clinical assays for proteins in plasma and serum. Clin Chem. Feb. 2010;56(2):177-85. doi: 10.1373/clinchem.2009.126706. Epub Nov. 2, 2009.
Braha et al., Designed protein pores as components for biosensors. Chem Biol. Jul. 1997;4(7):497-505. doi: 10.1016/s1074-5521(97)90321-5.

(Continued)

*Primary Examiner* — Galina M. Yakovleva
(74) *Attorney, Agent, or Firm* — Wolf, Greenfield & Sacks, P.C.

(57) ABSTRACT

The invention relates to a method of determining the presence or absence of a target analyte in a sample. The method comprises immobilising any target analyte present in the sample on a surface; contacting the surface with: (i) a first detection agent that binds specifically to the target analyte; and (ii) a reporter polynucleotide, wherein the reporter polynucleotide is bound to, or binds to, the first detection agent; and contacting a transmembrane pore with any reporter polynucleotide that has been immobilised on the surface, wherein the reporter polynucleotide is immobilised on the surface by binding of the first agent to the target analyte, and using the transmembrane pore to detect the reporter polynucleotide, thereby determining the presence or absence of the target analyte in the sample.

20 Claims, 5 Drawing Sheets
Specification includes a Sequence Listing.

(56) References Cited

FOREIGN PATENT DOCUMENTS

| | | |
|---|---|---|
| WO | WO 2010/086602 A1 | 8/2010 |
| WO | WO 2010/086603 A1 | 8/2010 |
| WO | WO 2010/086620 A1 | 8/2010 |
| WO | WO 2011/067559 A1 | 6/2011 |
| WO | WO 2012/003330 A2 | 1/2012 |
| WO | WO 2012/042226 A2 | 4/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/109970 A1 | 7/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/074922 A1 | 5/2014 |
| WO | WO 2014/135838 A1 | 9/2014 |
| WO | WO 2015/014035 A1 | 2/2015 |
| WO | WO 2015/022544 A1 | 2/2015 |
| WO | WO 2015/055981 A2 | 4/2015 |
| WO | WO 2015/110777 A1 | 7/2015 |
| WO | WO 2015/110813 A1 | 7/2015 |
| WO | WO 2015/124935 A1 | 8/2015 |
| WO | WO 2015/127387 A1 | 8/2015 |
| WO | WO 2015/150786 A1 | 10/2015 |
| WO | WO 2015/150787 A1 | 10/2015 |
| WO | WO 2015/166275 A1 | 11/2015 |
| WO | WO 2015/176034 A1 | 11/2015 |
| WO | WO 2016/034591 A2 | 3/2016 |
| WO | WO 2016/055777 A2 | 4/2016 |
| WO | WO 2016/059363 A1 | 4/2016 |
| WO | WO 2016/059375 A1 | 4/2016 |
| WO | WO 2016/059427 A1 | 4/2016 |
| WO | WO 2016/059436 A1 | 4/2016 |
| WO | WO 2016/099673 A1 | 6/2016 |
| WO | WO 2016/161402 A1 | 10/2016 |
| WO | WO 2017/125565 A1 | 7/2017 |
| WO | WO 2017/203269 A1 | 11/2017 |
| WO | WO 2018/100370 A1 | 6/2018 |

OTHER PUBLICATIONS

Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.

Edwards et al., The role of proteomics in clinical cardiovascular biomarker discovery. Mol Cell Proteomics. Oct. 2008;7(10):1824-37. doi: 10.1074/mcp.R800007-MCP200. Epub Jul. 30, 2008.

González-Pérez et al., Biomimetic triblock copolymer membrane arrays: a stable template for functional membrane proteins. Langmuir. Sep. 15, 2009;25(18):10447-50. doi: 10.1021/la902417m.

Grant et al., A facile method for attaching nitroxide spin labels at the 5' terminus of nucleic acids. Nucleic Acids Res. 2007;35(10):e77. doi: 10.1093/nar/gkm240. Epub May 21, 2007.

Heron et al., Simultaneous measurement of ionic current and fluorescence from single protein pores. J Am Chem Soc. Feb. 11, 2009;131(5):1652-3. doi: 10.1021/ja808128s.

Holden et al., Direct introduction of single protein channels and pores into lipid bilayers. J Am Chem Soc. May 11, 2005;127(18):6502-3. doi: 10.1021/ja042470p.

Holden et al., Functional bionetworks from nanoliter water droplets. J Am Chem Soc. Jul. 11, 2007;129(27):8650-5. doi: 10.1021/ja072292a. Epub Jun. 16, 2007.

Hornblower et al., Single-molecule analysis of DNA-protein complexes using nanopores. Nat Methods. Apr. 2007;4(4):315-7. doi: 10.1038/nmeth1021. Epub Mar. 4, 2007.

Ivanov et al., DNA tunneling detector embedded in a nanopore. Nano Lett. Jan. 12, 2011;11(1):279-85. doi: 10.1021/nl103873a. Epub Dec. 6, 2010.

Jacquet et al., Identification of cardiac myosin-binding protein C as a candidate biomarker of myocardial infarction by proteomics analysis. Mol Cell Proteomics. Dec. 2009;8(12):2687-99. doi: 10.1074/mcp.M900176-MCP200. Epub Aug. 31, 2009.

Jiang et al., miR2Disease: a manually curated database for microRNA deregulation in human disease. Nucleic Acids Res. Jan. 2009;37(Database issue):D98-104. doi: 10.1093/nar/gkn714. Epub Oct. 15, 2008.

Köhler et al., Continuous cultures of fused cells secreting antibody of predefined specificity. Nature. Aug. 7, 1975;256(5517):495-7. doi: 10.1038/256495a0.

Kumar et al., Nonradioactive labeling of synthetic oligonucleotide probes with terminal deoxynucleotidyl transferase. Anal Biochem. Mar. 1988;169(2):376-82. doi: 10.1016/0003-2697(88)90299-0.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.

Maddox et al., Elevated serum levels in human pregnancy of a molecule immunochemically similar to eosinophil granule major basic protein. J Exp Med. Oct. 1, 1983;158(4):1211-26. doi: 10.1084/jem.158.4.1211.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Nikolov et al., Behavior of giant vesicles with anchored DNA molecules. Biophys J. Jun. 15, 2007;92(12):4356-68. doi: 10.1529/biophysj.106.100032. Epub Mar. 23, 2007.

Patz et al., Panel of serum biomarkers for the diagnosis of lung cancer. J Clin Oncol. Dec. 10, 2007;25(35):5578-83. doi: 10.1200/JCO.2007.13.5392.

Pfeiffer et al., Bivalent cholesterol-based coupling of oligonucleotides to lipid membrane assemblies. J Am Chem Soc. Aug. 25, 2004;126(33):10224-5. doi: 10.1021/ja048514b.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Troutt et al., Ligation-anchored PCR: a simple amplification technique with single-sided specificity. Proc Natl Acad Sci U S A. Oct. 15, 1992;89(20):9823-5. doi: 10.1073/pnas.89.20.9823. Erratum in: Proc Natl Acad Sci U S A Apr. 15, 1993;90(8):3775.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f. PMID: 20180548; PMCID: PMC2877162.

Yoshina-Ishii et al., Arrays of mobile tethered vesicles on supported lipid bilayers. J Am Chem Soc. 2003 Apr. 2, 2003;125(13):3696-7. doi: 10.1021/ja029783+.

International Search Report and Written Opinion for Application No. PCT/GB2017/051493, dated Oct. 24, 2017.

International Preliminary Report on Patentability for Application No. PCT/GB2017/051493, dated Dec. 6, 2018.

International Search Report and Written Opinion for Application No. PCT/GB2017/053603, dated Apr. 6, 2018.

International Preliminary Report on Patentability for Application No. PCT/GB2017/053603, dated Jun. 13, 2019.

International Search Report and Written Opinion for Application No. PCT/GB2019/051571, dated Sep. 10, 2019.

International Preliminary Report on Patentability for Application No. PCT/GB2019/051571, dated Dec. 17, 2020.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

(56) References Cited

OTHER PUBLICATIONS

Biswas et al., Click Addition of a DNA Thread to the N-Termini of Peptides for Their Translocation through Solid-State Nanopores. ACS Nano. Oct. 27, 2015;9(10):9652-64. doi: 10.1021/acsnano.5b04984. Epub Sep. 16, 2015. Author Manuscript, 26 pages.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Technologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Chen et al., High spatial resolution nanoslit SERS for single-molecule nucleobase sensing. Nat Commun. Apr. 30, 2018;9(1):1733. doi: 10.1038/s41467-018-04118-7.

Colas et al., Microscopical investigations of nisin-loaded nanoliposomes prepared by Mozafari method and their bacterial targeting. Micron. 2007;38(8):841-7.

Devereux et al., A comprehensive set of sequence analysis programs for the VAX. Nucleic Acids Res. Jan. 11, 1984;12(1 Pt 1):387-95.

Eliseev et al., Molecular Recognition of Nucleotides, Nucleosides, and Sugars by Aminocyclodextrins. J. Am. Chem. Soc., 1994;116:6081-6088.

Feng et al., Nanopore-based fourth-generation DNA sequencing technology. Genomics Proteomics Bioinformatics. Feb. 2015;13(1):4-16. doi: 10.1016/j.gpb.2015.01.009. Epub Mar. 2, 2015. Erratum in: Genomics Proteomics Bioinformatics. Dec. 2015;13(6):383. Erratum in: Genomics Proteomics Bioinformatics. Jun. 2015;13(3):200-201. Erratum in: Genomics Proteomics Bioinformatics. Dec. 2015;13(6):383.

Howorka et al., A Protein Pore with a Single Polymer Chain Tethered within the Lumen. J. Am. Chem. Soc. Feb. 29, 2000;122(11):2411-2416. https://doi.org/10.1021/ja993221h.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Hu et al., Detection and analysis of DNA recapture through a solid-state nanopore. Chinese science bulletin. Dec. 2014;59(35):4953-9.

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Kozarewa et al., 96-plex molecular barcoding for the Illumina Genome Analyzer. Methods Mol Biol. 2011;733:279-98. doi: 10.1007/978-1-61779-089-8_20.

Langecker et al., Synthetic lipid membrane channels formed by designed DNA nanostructures. Science. Nov. 16, 2012;338(6109):932-6. doi: 10.1126/science.1225624.

Liu et al., Adding new chemistries to the genetic code. Annu Rev Biochem. 2010;79:413-44. doi: 10.1146/annurev.biochem.052308.105824.

Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.

Stranges et al., Design and characterization of a nanopore-coupled polymerase for single-molecule DNA sequencing by synthesis on an electrode array. Proc Natl Acad Sci U S A. Nov. 1, 2016;113(44):E6749-E6756. doi: 10.1073/pnas.1608271113. Epub Oct. 11, 2016.

United States District Court for the District of Delaware Order. *Pacific Biosciences of California, Inc*, v. *Oxford Nanopore Technolgoies, Inc*. Civil Action No. 17-275-RGA. Nov. 9, 2017.

Wendell et al., Translocation of double-stranded DNA through membrane-adapted phi29 motor protein nanopores. Nat Nanotechnol. Nov. 2009;4(11):765-72. doi: 10.1038/nnano.2009.259. Epub Sep. 27, 2009. Author Manuscript, 17 pages.

Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.

\* cited by examiner

METHOD OF DETERMINING THE PRESENCE OR ABSENCE OF A TARGET ANALYTE COMPRISING USING A REPORTER POLYNUCLEOTIDE AND A TRANSMEMBRANE PORE

RELATED APPLICATIONS

This Application is a national stage filing under 35 U.S.C. 371 of international application number PCT/GB2018/051190, filed May 3, 2018, which claims the benefit of United Kingdom application number 1707140.8, filed May 4, 2017, each of which is incorporated by reference in its entirety.

FIELD OF THE INVENTION

The invention relates to a new assay for detecting molecular interactions, such as protein-protein interactions. The method may be used to of determine the presence, absence or amount of a target analyte in a sample. The method may be carried out in a multiplex format and may be used to determine the presence, absence or amount of multiple analytes simultaneously. The method may be used to screen for binding partners of a target analyte.

BACKGROUND

There is a need for techniques which can detect the presence of low concentrations of analytes with high accuracy, particularly when multiple analytes are present in a single sample. The need is particularly acute for detection of biomarkers and thus the diagnosis of the associated disease or disorder.

Transmembrane pores (nanopores) have great potential as direct, electrical biosensors for a variety of analytes, such as polymers and small molecules. When a potential is applied across a nanopore, there is a change in the current flow when a molecule, such as a nucleotide or a polynucleotide, resides transiently in the barrel or channel of the nanopore for a certain period of time. Specific molecules, such as specific nucleotides and specific polynucleotides, give current changes of known signature and duration. Such current changes can be used to identify the nucleotide or polynucleotide present in the pore. Devices comprising an array of nanopores may be used to detect and characterise polynucleotides, for example to sequence the polynucleotides.

SUMMARY

The inventors have demonstrated that a combination of antibodies and polynucleotides can be used in a nanopore-based immunosorbent assay to determine the presence, absence or concentration of an analyte. The assay is ideal for determining the presence, absence or concentration of one or more analytes. The assay may detect one target analyte or may be a multiplex assay that is capable of detecting more than one target analyte.

More specifically, the inventors have demonstrated that the concentration of a target analyte can be determined in a uniplex assay using a capture antibody immobilised on a surface and a detection antibody and a polynucleotide reporter. The detection antibody and the polynucleotide used by the inventors were functionalised with biotin and streptavidin was used to bind the polynucleotide reporter to the detection antibody, but other attachment means may be used. The amount of reporter polynucleotide bound to the detection antibody depends on the amount of analyte immobilized on the surface. The reporter polynucleotide immobilised on the surface by binding to the detection antibody bound to the captured analyte was detected directly (after being released from the surface but without amplification) using a transmembrane pore. The inventors have shown that the amount of reporter polynucleotide detected is proportional to the amount of analyte captured on the surface. By using a suitable calibration method, the concentration of analyte in the sample can therefore be determined.

The inventors have also demonstrated that the concentrations of more than one target analyte (i.e. two or more target analytes) can be determined in a multiplex assay. In the method used by the inventors, each analyte was captured and labelled with a different reporter polynucleotide. The bound reporter polynucleotides were eluted and pooled for detection using a transmembrane pore. Different known concentrations of each analyte were used, with each concentration being detected using a different reporter polynucleotide, to show that the assay can be used to simultaneously determine the concentration of multiple analytes. The sensitivity of detection for each analyte was found to exceed that required to detect and measure the concentrations of the analytes at their physiological concentrations. In the Examples, the assay was multiplexed at the level of sequencing. However, by using specific attachment means (such as attaching a different oligonucleotide (or multiple copies thereof) that specifically hybridises to one reporter polynucleotide to each detection agent) or by pre-assembling the detection agent/reporter polynucleotide, several analytes can be assayed in a single reaction.

In the diagnosis and assessment of disease, such as the measurement of disease progress or response to treatment or the determination of likely responsiveness to a treatment, it is typically necessary to detect and/or quantify at least one biomarker, more often two or more biomarkers. The inventors have determined that a panel of biomarkers can be quantified simultaneously using their method. The method can be performed easily without the need for bulky equipment. For example, the method can be carried out using a standard immunoassay plate (such as an ELISA plate) or beads, and the reporter polynucleotides can be detected using a hand-held device comprising an array of nanopores (flowcell).

The method allows the reporter read count to be balanced for all the different biomarkers in a panel, even though they may occur at vastly different levels in the sample (such as serum). The relatively low number of reporter reads needed for sensitive protein quantification means that a large biomarker panel can be quantified on a single flowcell while that same flowcell is used to sequence the exome and/or transcriptome simultaneously. Thus, the method can be used to provide a comprehensive assessment of the status of the health of an individual.

The inventors have recognised that the method can be used to identify binding partners of a target analyte, such as a drug target. Hence, a method of drug screening is also provided.

Accordingly, provided are:

a method of determining the presence or absence of a target analyte in a sample, the method comprising:
  (a) immobilising any target analyte present in the sample on a surface;
  (b) contacting the surface with: (i) a first detection agent that binds specifically to the target analyte; and (ii) a reporter polynucleotide, wherein the reporter polynucleotide is bound to, or binds to, the first detection agent; and (c) contacting a transmembrane pore with any reporter polynucleotide that has been immobilised on the surface, wherein the reporter polynucleotide is immobilised on the surface by binding of the first agent to the target analyte, and using the transmembrane pore to detect the reporter polynucleotide, thereby determining the presence or absence of the target analyte in the sample;

a method of determining the presence or absence of two or more target analytes in a sample, wherein each target analyte is detected using a different reporter polynucleotide and the identities of the reporter polynucleotides are determined using the transmembrane pore and the method steps are as defined above;

a method of identifying a binding partner of a target analyte, the method comprising:

(a) immobilising the target analyte on a surface;

(b) contacting the surface with a candidate binding partner and a reporter polynucleotide, wherein the reporter polynucleotide is bound to, or binds to, the candidate binding partner; and (c) detecting using a transmembrane pore any reporter polynucleotide that has been immobilised on the surface, wherein the reporter polynucleotide is immobilised on the surface by binding of the first agent to the target analyte, thereby determining whether the candidate molecule is a binding partner of the target analyte; and a kit for detecting a target analyte comprising:

(a) (i) a polynucleotide attached to first component of an affinity tag;
(ii) a second component of the affinity tag; and
(iii) a specific binding agent for the target analyte which is attached to the second component of the affinity tag or comprises an antibody and a first component of the affinity tag; or (b) (i) a polynucleotide; and
(ii) a specific binding agent for the target analyte which is attached to an oligonucleotide that hybridises to at least a portion of the polynucleotide; or (c) (i) a specific binding agent for the target analyte; and
(ii) a polynucleotide, wherein the polynucleotide is bound to, or is capable of binding to, the specific binding agent and comprises an adaptor at a free end, which adaptor facilitates interaction of the reporter polypeptide with the transmembrane pore.

Figure 1:
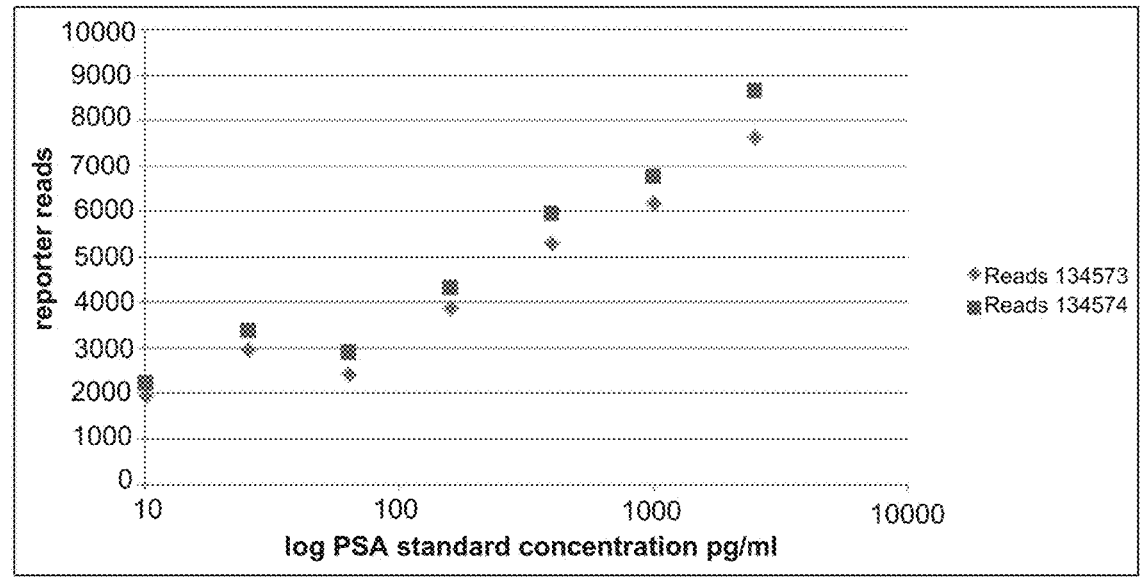
FIG. 1: Sequencing results for two Flow Cell runs of the barcoded reporter polynucleotide pool collected from the PSA ELISA wells. The concentration of PSA protein (pg/ml) added to each ELISA well is correlated with the number of reads of the associated barcoded reporter polynucleotide.

1. A capture agent which is an antibody that specifically binds to the target analyte is attached to the surface, the first detection agent is an antibody to the target analyte and the reporter polynucleotide is bound directly to or bind directly to the first detection agent. The capture agent is preferably an antibody that binds to a different epitope on the analyte from the first detection agent. The epitope to which the first detection agent binds is accessible when the target analyte is bound to the capture antibody.

2. A capture agent which is an antibody that specifically binds to the target analyte is attached to the surface, the first detection agent is an antibody to the target analyte (primary antibody), the second detection agent is an antibody that binds to the first detection agent (secondary antibody) and the reporter polynucleotide is bound to, or binds to, the second detection agent. The capture agent is preferably an antibody that binds to a different epitope on the analyte from the first detection agent. The epitope to which the first detection agent binds is accessible when the target analyte is bound to the capture antibody.

3. The target analyte is non-specifically bound to the surface. The first detection agent is an antibody to the target analyte (primary antibody), the second detection agent is an antibody that binds to the first detection agent (secondary antibody) and the reporter polynucleotide is bound to, or binds to, the second detection agent.

4. A capture agent which is an antibody that binds to the target analyte, which is an antibody (target antibody), is attached to the surface. The antibody may bind to a common epitope on a group of similar molecules, such as antibodies of the same isotype from a particular species, e.g. human IgG antibodies. The first detection agent is the antigen of the target antibody. The second detection agent is an antibody to the antigen and the reporter polynucleotide is bound to, or binds to, the second detection agent. The second detection agent is preferably an antibody that binds to a different epitope on the antigen from the target antibody. The epitope to which the second detection agent binds is preferably accessible when the target analyte is bound to the target antibody.

5. A capture agent which is an antibody that binds to the target analyte, which is an antibody (target antibody), is attached to the surface. The antibody may bind to a common epitope on a group of similar molecules, such as antibodies of the same isotype from a particular species, e.g. human IgG antibodies. The first detection agent is the antigen of the target antibody and the reporter polynucleotide is bound to, or binds to, the second detection agent.

6. A capture agent which is an antigen that binds to the target analyte, which is an antibody (target antibody), may be attached to the surface. The first detection agent is an antibody that binds to the target antibody and the reporter polynucleotide is bound to, or binds to, the second detection agent.

DETAILED DESCRIPTION

It is to be understood that different applications of the disclosed products and methods may be tailored to the specific needs in the art. It is also to be understood that the terminology used herein is for the purpose of describing particular embodiments only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a surface" includes two or more such surfaces, reference to "a antibody" includes two or more such antibodies, reference to "a polynucleotide" includes two or more such polynucleotides, and the like.

All publications, patents and patent applications cited herein, whether supra or infra, are hereby incorporated by reference in their entirety.

Methods

Provided is a method of determining the presence or absence of a target analyte. The target analyte is typically present in a sample. The method may be a uniplex method that measures one target analyte. The target analyte is typically predetermined. The method uses components that are designed to specifically recognise the target analyte.

The method has several advantages. The method is highly sensitive, does not require a large amount of starting material, has a high throughput, does not require amplification of target polynucleotides and can be performed directly on blood, serum or plasma. The method can also be used to detect and quantify multiple target analytes at the same time, i.e. the method may be a multiplex method. The method can be used to detect many target analytes from a single sample, thus obviating the need for multiple tests on a single sample. The number of target analytes is not limited. Each target analyte is specifically detected and associated with a unique reporter polynucleotide. There are no restrictions on the length of the polynucleotide. Therefore, a vast number of different reporter polynucleotide sequences can be generated and distinguished by sequencing using a transmembrane pore.

The method is rapid and cheap compared to existing assays, whilst still having high specificity. The output is analysed in real time, allowing the assays to be stopped when sufficient information has been obtained. The methods can be carried out by someone with minimal training or qualification.

The method may be based on a sandwich immunosorbent assay that uses a capture antibody to specifically immobilise the target analyte to a surface, and a detection antibody that specifically binds to the target analyte to bind to the captured target analyte. The method is not, however, limited to the typical sandwich immunosorbent assay format and may be carried out in other ways.

The method of determining the presence or absence of a target analyte comprises:

(a) immobilising any target analyte present in the sample on a surface;

(b) contacting the surface with a first detection agent that binds specifically to the target analyte and with a reporter polynucleotide, wherein the reporter polynucleotide is bound to, or binds to, the first detection agent; and (c) contacting a transmembrane pore with any reporter polynucleotide that has been immobilised on the surface, wherein the reporter polynucleotide is immobilised on the surface by binding of the first agent to the target analyte, and using the transmembrane pore to detect the reporter polynucleotide, thereby determining the presence or absence of the target analyte in the sample.

Due to the specificity of the first detection agent for the target analyte, the reporter polynucleotide is only bound to the surface and then detected by the transmembrane pore if the target analyte is present in the sample. The target analyte is determined to be present if the reporter polynucleotide is detected using the transmembrane pore. The target analyte is absent if the reporter polynucleotide is not detected using the transmembrane pore. The method does not include an amplification step, such as PCR. The reporter polynucleotide molecules that are bound to the surface via the detection agent(s) and target analyte are the same polynucleotide molecules that interact with the transmembrane pore. The number of copies of the reporter polynucleotide detected using the pore (reporter read count) is correlated with the concentration of the target analyte in the sample. The method is a quantitative method. Hence the reporter read count may be used to determine the concentration of the target analyte in the sample. This may be achieved using standard methods, such as by comparing the read count with a correlation curve generated by performing the method using known concentrations of the target analyte.

The target analyte may be immobilised on the surface by any suitable means. The target analyte may be bound non-specifically to the surface. The non-specific binding of the target analyte to the surface may involve capturing all molecules of a given type to the surface, such as all proteins present in the sample. In one embodiment, all proteins of a certain type, such as all antibodies or all antibodies of a given subtype, such as IgG, IgM, IgA or IgE may be captured on the surface. This may be achieved by coating the surface with suitable antibodies, such as, for example, anti-human IgG antibodies.

It is preferred that the target analyte is specifically bound to the surface. This can be achieved by standard means. Typically, the target analyte is immobilised on the surface by binding to a capture agent that binds specifically to the target analyte, which capture agent is immobilised on the surface. Suitable capture agents are known in the art and include antibodies, aptamers, receptor molecules where the target analyte is a ligand, ligand molecules where the target analyte is a receptor and antigens where the target analyte is an antibody. Methods of coating a surface with a capture agent are known in the art and typically include a blocking step to reduce or prevent non-specific binding to the surface. Preferably the capture agent is an antibody, or an antigen. The antibody preferably binds specifically to the target analyte.

The first detection agent may be any molecule that binds specifically to the target analyte. The detection agent is preferably an antibody, but may be an aptamer, a receptor molecule where the target analyte is a ligand, a ligand molecule where the target analyte is a receptor or an antigen where the target analyte is an antibody.

For example, where the target analyte is an antibody, the first detection agent may be an antibody which binds to the target antibody and the capture agent may be an antigen to which the target antibody binds; or the first detection agent may be an antigen to which the target antibody binds and the capture agent may be an antibody which binds to the target antibody. The first detection agent may be referred to as a primary antibody.

The reporter polynucleotide may be attached to the first detection agent directly or indirectly.

The reporter polynucleotide may be attached to the first detection agent prior to step (b) of the claimed method, i.e. the reporter polynucleotide may be pre-bound to the first detection agent before the first detection agent is added to the surface on which the target analyte (if any) is immobilised. The reporter polynucleotide may alternatively be added to the assay separately from the first detection agent. It may then bind to the first detection agent in the vicinity of the surface. For example, the first detection agent may be added to the surface and allowed to bind to any target analyte on the surface. Any unbound first detection agent may be removed, typically by washing. The reporter polynucleotide may then be added and allowed to bind to the immobilised first detection agent.

In one embodiment, the reporter polynucleotide is attached to a second detection agent. The second detection agent is a molecule that binds to the first detection agent, but not to any other components of the assay. The second detection agent is preferably an antibody, but may be an aptamer, a receptor molecule where the first detection agent is a ligand, a ligand molecule where the first detection agent is a receptor, or an antigen where the first detection agent is an antibody. The second detection agent may be an antibody that binds to the first detection agent, such as an antibody that binds specifically to the constant region of an antibody of a particular species and/or isotype. For example, if the first detection agent is a mouse IgG antibody, the second detection agent may be a goat anti-mouse IgG antibody. The use of such first and second detection agents is routine in the art, for example in ELISA assays. The second detection agent may be referred to as a secondary antibody.

Where the reporter polynucleotide binds to the first detection agent via a second detection agent, the second detection agent is typically added to the assay after the first detection agent has been allowed to bind to any target analyte on the surface, and any unbound first detection agent has been removed, typically by washing. The reporter polynucleotide may be pre-bound to the second detection agent before the second detection agent is added to the surface on which the first detection agent (if any) is immobilised. The reporter polynucleotide may alternatively be added to the assay separately from the second detection agent. It may then bind to the second detection agent in the vicinity of the surface. For example, the second detection agent may be added to the surface and allowed to bind to any first detection agent on the surface. Any unbound second detection agent may be removed, typically by washing. The reporter polynucleotide may then be added and allowed to bind to the immobilised second detection agent.

The reporter polynucleotide may be bound to, or bind to, the first detection agent, or the second detection agent directly or indirectly. Any suitable means may be used to attach the reporter polynucleotide to a detection agent. Indirect binding includes binding via a second detection agent. Indirect binding also includes binding via a linker or a linker molecule.

In one embodiment, an affinity tag may be used to attach the reporter polynucleotide to the first or second detection agent. Suitable affinity tags include Streptavidin/Biotin, his tags, glutathione and Ni-NTA. Preferably, the affinity tag is biotin/streptavidin. The detection agent and/or reporter polynucleotide may be functionalised by the addition of biotin.

The reporter polynucleotide may be bound to, or may bind to, the first detection agent via a second detection agent that binds to the first agent. The second detection agent typically comprises an antibody.

In particular embodiments of the method, the first detection agent or the second detection agent comprises a first component of affinity tag and (a) the reporter polynucleotide is attached to a second component of the affinity tag that specifically binds to the first component; or (b) the reporter polynucleotide is attached to first component of affinity tag, and a second component of the affinity tag that specifically binds to the first component is used to link the first detection agent or the second detection agent to the reporter polynucleotide. For example, the first component of the affinity tag may be biotin and the second component of the affinity tag may be streptavidin.

In the method, the first detection agent or the second detection agent may comprise an oligonucleotide that hybridises to at least part of the reporter polynucleotide.

In the method, the reporter polynucleotide is typically from about 10 to 5000, such as 20 to 1000, 30 to 500 or 50 to 100, nucleotides in length. The reporter polynucleotide may comprise DNA, RNA, or a synthetic nucleic acid.

Two or more reporter polynucleotides, which may be identical, may be bound to, or bind to, the first detection agent.

The method may be a multiplex method used to simultaneously detect and/or quantify two or more target analytes. Typically, the assay may be used to detect and/or quantify two, ten, 20, 50 or more target analytes simultaneously, such as from 2 to 1000, 5 to 800, 10 to 500, 20 to 200, or 30 to 100 target analytes. Not all of the target analytes the assay is designed to detect may be present in the sample. The multiplex method may therefore determine the presence or absence of each member of a specific and predetermined group of two or more target analytes. The multiplex method may be used to determine the amount, such as concentration, of the target analytes in the sample. Where a target analyte is not present in the sample, the amount is zero. Thus, the method may be used to determine the amounts of all the target analytes of interest. In the multiplex method, multiple components as defined above are used. In order for the multiplex method to work effectively, typically each target analyte is specifically labelled with a different reporter polynucleotide. Each different reporter polypeptide typically has a different nucleotide sequence. The different reporter polynucleotides may be distinguished from one another by virtue of their different sequences. The sequences of the reporter polynucleotides may readily be determined using a nanopore sequencing method. The reporter polynucleotides may be mixed together and separated at the level of the nanopore, which can interact only with one polynucleotide at a time. All or part of the sequence of the reporter polynucleotide may be determined. It is sufficient to only sequence a distinct, preferably unique, part of a reporter polynucleotide in order to identify it.

Attachment of Reporter Polynucleotide to Detection Agent

The detection agent may be labelled with the reporter polynucleotide in any manner. The detection agent is typically labelled with the reporter polynucleotide in such a manner that the reporter polynucleotides are not removed by any washing step discussed below, but may be removed from the surface when being detected by the transmembrane pore. The labelling is preferably transient, i.e. the reporter polynucleotides do not detach from the detection agent during washing steps but may detach from the detection agent during the detecting step when interacting with the pore. A preferred transient attachment is via hybridisation. The detection agent may be functionalised with an oligonucleotide or a polynucleotide (such as any of those discussed above) which hybridises or specifically hybridises to the reporter polynucleotide.

The antibody is typically functionalized at a point distant from the antigen binding site of the antibody, typically in the constant region and preferably at the end of the antibody molecule. An oligonucleotide or polynucleotide specifically hybridises to a target polynucleotide when it hybridises with preferential or high affinity to the target polynucleotide but does not substantially hybridise, does not hybridise or hybridises with only low affinity to other polynucleotide.

An oligonucleotide or polynucleotide specifically hybridises if it hybridises to the target polynucleotide with a melting temperature ($T_m$) that is at least 2° C., such as at least 3° C., at least 4° C., at least 5° C., at least 6° C., at least 7° C., at least 8° C., at least 9° C. or at least 10° C., greater than its $T_m$, for other sequences. More preferably, the oligonucleotide or polynucleotide hybridises to the target polynucleotide with a $T_m$, that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$, for other nucleic acids. Preferably, the oligonucleotide or polynucleotide hybridises to the target polynucleotide with a $T_m$, that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$, for a sequence which differs from the target polynucleotide by one or more nucleotides, such as by 1, 2, 3, 4 or 5 or more nucleotides. The oligonucleotide or polynucleotide typically hybridises to the target polynucleotide with a $T_m$, of at least 90° C., such as at least 92° C. or at least 95° C. $T_m$, can be measured experimentally using known techniques, including the use of DNA microarrays, or can be calculated using publicly available $T_m$, calculators, such as those available over the internet.

Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a 20 wash in from 1× (0.1650 M Na$^+$) to 2× (0.33 M Na$^+$) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na$^+$) to 1× (0.1650 M Na$^+$) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na$^+$) SSC at 60° C.

The oligonucleotide or polynucleotide may comprise a portion or region which is substantially complementary to a portion or region of the reporter polynucleotide. The region or portion of the oligonucleotide or polynucleotide may therefore have 1, 2, 3, 4, 5, 6, 7, 8, 9, 10 or more mismatches across a region of 5, 10, 15, 20, 21, 22, 30, 40 or 50 nucleotides compared with the portion or region in the reporter polynucleotide.

A portion of region is typically 50 nucleotides or fewer, such as 40 nucleotides or fewer, 30 nucleotides or fewer, 20 nucleotides or fewer, 10 nucleotides or fewer or 5 nucleotides or fewer.

Alternatively, both the detection agent and the reporter polynucleotide may be attached to oligonucleotide or polynucleotides which hybridise together or are complementary to each other.

Other preferred transient attachments include, but are not limited to, attachment using a polyhistidine-tag (hexa histidine-tag, 6xHis-tag, His6 tag or His-tag®), Ni-NTA or streptavidin-biotin.

A preferred method is for the first or second detection agent and the reporter polynucleotide to be biotinylated and then bound together using streptavidin. The skilled person can devise other suitable labelling methods. The first or second detection agent may be functionalised with any of the groups discussed above with reference to the surface.

In some embodiments, the first and/or second detection agent is a chemically modified antibody. The antibody can be chemically modified in any way and at any site. The antibody can be chemically modified by attachment of a molecule to one or more cysteines (cysteine linkage), attachment of a molecule to one or more lysines, attachment of a molecule to one or more non-natural amino acids, enzyme modification of an epitope or modification of a terminus.

Suitable methods for carrying out such modifications are well-known in the art. Suitable non natural amino acids include, but are not limited to, 4-azido-L-phenylalanine (Faz) and any one of the amino acids numbered 1-71 in FIG. 1 of Liu C. C. and Schultz P. G., Annu. Rev. Biochem. 2010, 79, 413-444. The antibody may be chemically modified by the attachment of any molecule. For instance, the antibody may be chemically modified by attachment of a polyethylene glycol (PEG), a nucleic acid such as DNA, a dye, a fluorophore or a chromophore.

In some embodiments, the antibody is chemically modified with a molecular adaptor. The molecular adaptor can be a cyclic molecule, for example a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding. The adaptor more preferably comprises one or more chemical groups that are capable of interacting with one or more amino acids via non-covalent interactions, such as hydrophobic interactions, hydrogen bonding, Van der Waal's forces, cation interactions and/or electrostatic forces. The chemical groups that are capable of interacting with one or more amino acids are typically hydroxyls or amines. The hydroxyl groups can be attached to primary, secondary or tertiary carbon atoms. The hydroxyl groups may form hydrogen bonds with uncharged amino acids.

The adaptor can be covalently attached to the antibody using any method known in the art. The adaptor is typically attached via chemical linkage. If the molecular adaptor is attached via cysteine linkage the one or more cysteines have preferably been introduced to the mutant by substitution. The antibody may be chemically modified by attachment of a molecular adaptor to one or both of these cysteines. Alternatively, the antibody may be chemically modified by attachment of a molecule to one or more cysteines or non-natural amino acids, such as FAz, introduced at other positions. The reactivity of cysteine residues may be enhanced by modification of the adjacent residues. For instance, the basic groups of flanking arginine, histidine or lysine residues will change the pKa of the cysteines thiol group to that of the more reactive S group. The reactivity of cysteine residues may be protected by thiol protective groups such as dTNB. These may be reacted with one or more cysteine residues of the antibody before a linker is attached.

The molecule is preferably attached to the antibody using a linker, such as a chemical crosslinker or a peptide linker. Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the antibody. Suitable linkers include, but are not limited to, iodoacetamide-based and Maleimide-based linkers. In other embodiment, the antibody may be attached to a polynucleotide binding protein. Polynucleotide binding proteins are discussed below.

The polynucleotide binding protein can be covalently attached to the antibody using any method known in the art. The antibody and polynucleotide binding protein may be chemically fused or genetically fused. Genetic fusion of a protein to a polynucleotide binding protein is discussed in WO 2010/004265.

The polynucleotide binding protein may be attached directly to the antibody via one or more linkers. The polynucleotide binding protein may be attached to the antibody using the hybridization linkers described in WO 2010/086602. Alternatively, peptide linkers may be used. Peptide linkers are amino acid sequences. The length, flexibility and hydrophilicity of peptide linker are typically designed such that it does not to disturb the functions of the antibody. Preferred flexible peptide linkers are stretches of 2 to 20, such as 4, 6, 8, 10 or serine and/or glycine amino acids. More preferred flexible linkers include (SG)i, (SG)~, (SG)~ (SG)4, (SG)q And (SG)8 wherein S is serine and G is glycine. Preferred rigid linkers are stretch of 2 to 30, such as 4, 6, 8, 16 or 24, proline amino acids. More preferred rigid linkers include (P)iz wherein P is proline.

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPyS (Grant, G. P. and P. Z. Qin (2007). "A facile method for attaching nitroxide spin labels at the 5' terminus of nucleic acids." Nucleic Acids Res 35(10): e77). A more diverse selection of chemical groups, such as biotin, thiols and fluorophores, can be added using terminal transferase to incorporate modified oligonucleotides to the 3' of ssDNA Kumar, A., P. Tchen, et al. (1988). "Nonradioactive labeling of synthetic oligonucleotide probes with terminal deoxynucleotidyl transferase." Anal Biochem 169(2): 376-82).

Alternatively, the reactive group could be considered to be the addition of a short piece of DNA complementary to one already coupled to the antibody, so that attachment can be achieved via hybridisation. Ligation of short pieces of ssDNA have been reported using T4 RNA ligase I Troutt, A. B., M. G. McHeyzer-Williams, et al. (1992). "Ligation-anchored PCR: a simple amplification technique with single-sided specificity." Proc Natl Acad Sci USA 89(20): 98235). Alternatively either ssDNA or dsDNA could be ligated to native dsDNA and then the two strands separated by thermal or chemical denaturation. It is possible to add either a piece of ssDNA to one or both of the ends of a native DNA duplex, or dsDNA to one end or both ends. Then, when the duplex is melted, each single strand will have either a 5' or 3' modification if ssDNA was used for ligation, or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it. A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has reactive group, such as a cholesterol, thiol, biotin or lipid, each copy of the target DNA amplify will contain a reactive group for coupling.

A polynucleotide binding protein can be used. It is straightforward in the art determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target sequence. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be and of those disclosed WO 010/086603. Preferred enzymes are polymerases, exonucleases, helicases and topoisomerases, such as gyrases.

Sample

Each analyte is typically present in any suitable sample. The method is typically carried out on two or more samples that are known to contain or suspected to contain the analytes. Alternatively, the method may be carried out on two or more samples to confirm the identity of two or more analytes whose presence in the samples is known or expected.

The sample may be a biological sample. The method may be carried out in vitro using at least one sample obtained from or extracted from any organism or microorganism. The organism or microorganism is typically archaeal, prokaryotic or eukaryotic and typically belongs to one of the five kingdoms: plantae, animalia, fungi, monera and protista. The method may be carried out in vitro on a sample obtained from or extracted from any virus. The sample is preferably a fluid sample.

The sample may comprise a body fluid of a patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs.

Alternatively, the first sample and/or second sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa or cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the method, for example by centrifugation or by passage through a membrane that filters out unwanted molecules or cells, such as red blood cells. The sample may be measured immediately upon being taken. The sample may also be typically stored prior to assay, preferably below −70° C.

Analyte

The method is for determining in a sample the presence or absence of one (uniplex method) or more than one (multiplex method) target analyte. In the uniplex method, the target analyte is either present or absent. The method is quantitative and may be used to determine the amount of target analyte present in the sample. The concentration of the analyte may be determined using a suitable calibration curve. The use of calibration curves is standard in the art.

Any number of analytes such as 2, 5, 10, 15, 20, 30, 40, 50, 100, 500, 1000, 1500, 1750, 2000 or more analytes may be analysed at the same time using the method. Preferably from about 2 to about 2000 analytes, such as from about 5 to about 1500 analytes, from about 10 to about 1000 analytes, from about 20 to about 500 analytes or from about 50 to about 100 analytes may be analysed simultaneously using the method.

The analyte may be any analyte which may be detected using an antibody. The analyte is preferably selected from metal ions, inorganic salts, polymers, amino acids, peptides, polypeptides, proteins, nucleotides, oligonucleotides, polynucleotides, dyes, bleaches, pharmaceuticals, diagnostic agents, recreational drugs, explosives and environmental pollutants. In the multiplex method, the group may comprise two or more analytes of the same type, such as two or more proteins, two or more nucleotides or two or more pharmaceuticals. Alternatively, the group may comprise two or more analytes of different types, such as one or more proteins, one or more nucleotides and one or more pharmaceuticals.

The analyte can be an analyte that is secreted from cells. Alternatively, the analyte can be an analyte that is present inside cells such that the analyte must be extracted from the cells before the method can be carried out.

The analyte is preferably selected from amino acids, peptides, polypeptides and/or proteins. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are discussed below with reference to the transmembrane pore. For present purposes, it is to be understood that the analyte can be modified by any method available in the art.

The protein can be selected from enzymes, antibodies, hormones, growth factors or growth regulatory proteins, such as cytokines. The cytokine may be selected from interleukins, preferably IFN-1, IL-1, IL-2, IL-4, IL-5, IL-6, IL-10, IL-12 and IL-13, interferons, preferably IL-γ, and other cytokines such as TNF-α. The protein may be a bacterial protein, a fungal protein, a viral protein or a parasite-derived protein.

The analyte is preferably selected from oligonucleotides and/or polynucleotides. A nucleotide typically contains a nucleobase, a sugar and at least one phosphate group. The nucleobase is typically heterocyclic. Nucleobases include, but are not limited to, purines and pyrimidines and more specifically adenine (A), guanine (G), thymine (T), uracil (U) and cytosine (C). The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

A nucleotide may be abasic (i.e. lack a nucleobase). A nucleotide may also lack a nucleobase and a sugar (i.e. is a C3 spacer).

Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the template polynucleotide may be damaged. For instance, the polynucleotide may comprise a pyrimidine dimer. Such dimers are typically associated with damage by ultraviolet light and are the primary cause of skin melanomas. One or more nucleotides in the template polynucleotide may be modified, for instance with a label or a tag. Suitable labels are described below. The template polynucleotide may comprise one or more spacers.

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be double stranded. The polynucleotide is preferably single stranded. The polynucleotide may be one strand from a double stranded polynucleotide.

The polynucleotides can be nucleic acids, such as deoxyribonucleic acid (DNA) or a ribonucleic acid (RNA). The polynucleotide may be any synthetic nucleic acid known in the art, such as peptide nucleic acid (PNA), glycerol nucleic acid (GNA), threose nucleic acid (TNA), locked nucleic acid (LNA), morpholino nucleic acid, a bridged nucleic acid (BNA) or another synthetic polymer with nucleotide side chains. The polynucleotide may comprise any of the nucleotides discussed above, including the modified nucleotides.

The target polynucleotide is preferably from about 15 to about 30 nucleotides in length, such as from about 20 to about 25 nucleotides in length. For example, the polynucleotide can be about 15, about 16, about 17, about 18, about 19, about 20, about 21, about 22, about 23, about 24, about 25, about 26, about 27, about 28, about 29 or about 30 nucleotides in length.

The group of two or more target polynucleotides may be any group of polynucleotides. For instance, the group may be associated with a particular phenotype. The group may be associated with a particular type of cell. For instance, the group may be indicative of a bacterial cell. The group may be indicative of a virus, a fungus or a parasite.

The target polynucleotide is preferably a microRNA (or miRNA). The group of two or more target polynucleotides is preferably a group of two or more miRNAs. Suitable miRNAs are well known in the art. For instance, suitable miRNAs are stored on publically available databases (Jiang Q., Wang Y., Hao Y., Juan L., Teng M., Zhang X., Li M., Wang G., Liu Y., (2009) miR2Disease: a manually curated database for microRNA deregulation in human disease. Nucleic Acids Res.).

The miRNA(s) can preferably be used to diagnose or prognose a disease or condition. The disease or condition is preferably cancer, coronary heart disease, cardiovascular disease or sepsis. The disease or condition is more preferably abdominal aortic aneurysm, acute lymphoblastic leukemia (ALL), acute myeloid leukemia (AML), acute myocardial infarction, acute promyelocytic leukemia (APL), adenoma, adrenocortical carcinoma, alcoholic liver disease, Alzheimer's disease, anaplastic thyroid carcinoma (ATC), anxiety disorder, asthma, astrocytoma, atopic dermatitis, autism spectrum disorder (ASD), B-cell chronic lymphocytic leukemia, B-cell lymphoma, Becker muscular dystrophy (BMD), bladder cancer, brain neoplasm, breast cancer, Burkitt lymphoma, cardiac hypertrophy, cardiomyopathy, cardiovascular disease, cerebellar neurodegeneration, cervical cancer, cholangiocarcinoma, cholesteatoma, choriocarcinoma, chronic lymphocytic leukemia, chronic myeloid leukemia, chronic pancreatitis, colon carcinoma, colorectal cancer, congenital heart disease, coronary artery disease, cowden syndrome, dermatomyositis (DM), diabetic nephropathy, diarrhea predominant irritable bowel syndrome, diffuse large B-cell lymphoma, dilated cardiomyopathy, down syndrome (DS), duchenne muscular dystrophy (DMD), endometrial cancer, endometrial endometrioid adenocarcinoma, endometriosis, epithelial ovarian cancer, esophageal cancer, esophagus squamous cell carcinoma, essential thrombocythemia (ET), facioscapulohumeral muscular dystrophy (FSHD), follicular lymphoma (FL), follicular thyroid carcinoma (FTC), frontotemporal dementia, gastric cancer (stomach cancer), glioblastoma, glioblastoma multiforme (GBM), glioma, glomerular disease, glomerulosclerosis, hamartoma, HBV-related cirrhosis, HCV infection, head and neck cancer, head and neck squamous cell carcinoma (HNSCC), hearing loss, heart disease, heart failure, hepatitis B, hepatitis C, hepatocellular carcinoma (HCC), hilar cholangiocarcinoma, Hodgkin's lymphoma, homozygous sickle cell disease (HbSS), Huntington's disease (HD), hypertension, hypopharyngeal cancer, inclusion body myositis (IBM), insulinoma, intrahepatic cholangiocarcinoma (ICC), kidney cancer, kidney disease, laryngeal carcinoma, late insomnia (sleep disease), leiomyoma of lung, leukemia, limb-girdle muscular dystrophies types 2A (LGMD2A), lipoma, lung adenocarcinoma, lung cancer, lymphoproliferative disease, malignant lymphoma, malignant melanoma, malignant mesothelioma (MM), mantle cell lymphoma (MCL), medulloblastoma, melanoma, meningioma, metabolic disease, miyoshi myopathy (MM), multiple myeloma (MM), multiple sclerosis, MYC-rearranged lymphoma, myelodysplastic syndrome, myeloproliferative disorder, myocardial infarction, myocardial injury, myoma, nasopharyngeal carcinoma (NPC), nemaline myopathy (NM), nephritis, neuroblastoma (NB), neutrophilia, Niemann-Pick type C (NPC) disease, non-alcoholic fatty liver disease (NAFLD), non-small cell lung cancer (NSCLC), obesity, oral carcinomaosteosarcoma ovarian cancer (OC), pancreatic cancer, pancreatic ductal adenocarcinoma (PDAC), pancreatic neoplasia, panic disease, papillary thyroid carcinoma (PTC), Parkinson's disease, PFV-1 infection, pharyngeal disease, pituitary adenoma, polycystic kidney disease, polycystic liver disease, polycythemia vera (PV), polymyositis (PM), primary biliary cirrhosis (PBC), primary myelofibrosis, prion disease, prostate cancer, psoriasic arthritis, psoriasis, pulmonary hypertension, recurrent ovarian cancer, renal cell carcinoma, renal clear cell carcinoma, retinitis pigmentosa (RP), retinoblastoma, rhabdomyosarcoma, rheumatic heart disease and atrial fibrillation, rheumatoid arthritis, sarcoma, schizophrenia, sepsis, serous ovarian cancer, Sezary syndrome, skin disease, small cell lung cancer, spinocerebellar ataxia, squamous carcinoma, T-cell leukemia, teratocarcinoma, testicular germ cell tumor, thalassemia, thyroid cancer, tongue squamous cell carcinoma, tourette's syndrome, type 2 diabetes, ulcerative colitis (UC), uterine leiomyoma (ULM), uveal melanoma, vascular disease, vesicular stomatitis or Waldenstrom macroglobulinemia (WM). Since the multiplex method may determine the presence of absence of two or more miRNAs, it is possible to prognose or diagnose two or more of any of the diseases listed above.

The method may be used to detect a group of two or more analytes, which may be any group of analytes. For instance, the group may be associated with a particular phenotype. The group may be associated with a particular type of cell. For instance, the group may be indicative of a bacterial cell. The group may be indicative of a virus, a fungus or a parasite. The group may be a specific panel of recreational drugs (such as the SAMHSA 5 panel test), of explosives or of environmental pollutants.

The group of two or more analytes is preferably a group of two or more biomarkers that can be used to diagnose or prognose a disease or condition. The biomarkers may be any of the analytes mentioned above, such as proteins or polynucleotides. Suitable panels of biomarkers are known in the art, for example as described in Edwards, A. V. G. et al. (2008) *Mol. Cell. Proteomics* 7, p 1824-1837; Jacquet, S. et al. (2009), *Mol. Cell. Proteomics* 8, p 2687-2699; Anderson N. L. et al (2010) *Clin. Chem.* 56, 177-185. The disease or condition is preferably cancer, coronary heart disease, cardiovascular disease or sepsis.

The group may comprise two or more analytes in the same class. Analytes are within the same class if they have structural similarity. If the analytes are proteins, they are within the same class if they are in the same Structural Classification of Proteins (SCOP) classification. Analytes are within the same class if they related functionally or related phylogenetically. For instance, the opiates, such as heroin, codeine and morphine, may be considered to be in the same class of analytes. Similarly, the different forms of interleukin 1, such as IL-1α, IL-1β and IL-1RA, may be considered to be in same class of analytes. In the present context, a class of analytes is typically two or more analytes that are different structurally but can be bound by one aptamer. The method preferably comprises the use of at least one probe which comprises an aptamer that binds to the analyte members in a class. For instance, such an embodiment allows the determination of the presence or absence of one or more IL-1 analytes in a sample. The ability to detect the presence or absence of one or more analyte members in a particular class has its advantages. For instance, an initial multiplex assay may be carried out for a variety of classes of analytes. Once the presence of one more classes has been determined, more specific multiplex assays relating to those classes may be carried out to determine the presence or absence of one or more of the analyte members within each class.

The inventors have recognised that the method can be used to identify binding partners of a target analyte, such as a drug target. Hence, a method of drug screening is also provided. In this embodiment, the drug target is immobilized on the surface, for example by non-specific binding (such as absorption) to the surface or by binding to a suitable capture agent. A panel of candidate agents, each associated with a different reporter gene may be added under conditions suitable for binding to the drug target. The candidate agents may each be bound to its respective reporter polynucleotide prior to addition to the assay, or detection agents specific for each of the candidate agents may be used, wherein the reporter polynucleotides are bound to or bind to the detection agents in a specific manner. The reporter nucleotides are then sequenced to identify the reporter polynucleotides and hence the candidate agents that have bound in the assay.

Surface

Any surface may be used in the method. Suitable examples include, but are not limited to, a probe, a plate, a column, a pin, a bead and a dipstick. The probe may be any of those discussed in M. A. Holden, H. Bayley. J. Am. Chem. Soc. 2005, 127, 6502-6503 and WO 2006/100484.

The surface may be any surface used in an enzyme-linked immunosorbent assay (ELISA). The surface may be a standard 96 or 384 well plate. Such plates are commercially available Fisher scientific, VWR suppliers, Nunc, Starstedt or Falcon.

The strength of binding of the capture agent to its target is typically sufficient such that the target remains bound to the antibody following any washing steps discussed below.

The capture agent, which may be an antibody, may be attached to the surface in any way. The attachment may be direct. The attachment may be indirect via one or more linkers or functionalisation molecules. The attachment may be covalent. The capture agent is typically attached to the surface such that it is not removed by any washing step discussed below. Methods for attaching capture agents to surfaces, such as microparticles, are known in the art.

The surface is preferably surface of one or more microparticles. Any number of microparticles can be used in the method. For instance, the method may use a single microparticle or 2, 3, 4, 5, 6, 7, 8, 9, 10, 20, 30, 50, 100, 1,000, 5,000, 10,000, 100,000, 500,000 or 1,000,000 or more microparticles. If two or more microparticles are used, the microparticles may be the same. Alternatively, a mixture of different microparticles may be used.

Each microparticle may have one capture agent attached. Alternatively, each microparticle may have two or more capture agents, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more capture agents, attached. A microparticle may be substantially or completed coated or covered with analyte. A microparticle may have a capture agent attached over substantially all of or all of its surface.

A microparticle is a microscopic particle whose size is typically measured in micrometres (μm). Microparticles may also known as microspheres or microbeads. The microparticle may be a nanoparticle. A nanoparticle is a microscopic particle whose size is typically measured in nanometres (nm).

A microparticle typically has a particle size of from about 0.001 μm to about 500 μm. For instance, a microparticle may have a particle size of from about 0.01 μm to about 200 μm or about 0.1 μm to about 100 μm. More often, a microparticle has a particle size of from about 0.5 μm to about 100 μm, or for instance from about 1 μm to about 50 μm. The microparticle may have a particle size of from about 1 nm to about 1000 nm, such as from about 10 nm to about 500 nm, about 20 nm to about 200 nm or from about 30 nm to about 100 nm.

A microparticle may be spherical or non-spherical. Spherical microparticles may be called microspheres. Non-spherical particles may for instance be plate-shaped, needle-shaped, irregular or tubular. The term "particle size" as used herein means the diameter of the particle if the particle is spherical or, if the particle is non-spherical, the volume-based particle size. The volume-based particle size is the diameter of the sphere that has the same volume as the non-spherical particle in question.

If two or more microparticles are used in the method, the average particle size of the microparticles may be any of the sizes discussed above, such as from about 0.5 μm to about 500 μm. A population of two or more microparticles preferably has a coefficient of variation (ratio of the standard deviation to the mean) of 10% or less, such as 5% or less or 2% or less.

Any method may be used to determine the size of the microparticle. Suitable methods include, but are not limited to, flow cytometry (see, for example, Chandler et al., J Thromb Haemost. 2011 June; 9(6):1216-24).

The microparticle may be formed from any material. The microparticle is preferably formed from a ceramic, glass, silica, a polymer or a metal. The polymer may be a natural polymer, such as polyhydroxyalkanoate, dextran, polylactide, agarose, cellulose, starch or chitosan, or a synthetic polymer, such as polyurethane, polystyrene, poly(vinyl chloride), silane or methacrylate. Suitable microparticles are known in the art and are commercially available. Ceramic and glass microspheres are commercially available from 3M®. Silica and polymer microparticles are commercially available from EPRUI Nanoparticles & Microspheres Co. Ltd. Microparticles are also commercially available from Polysciences Inc., Bangs Laboratories Inc. and Life Technologies.

The microparticle may be solid. The microparticle may be hollow. The microparticle may be formed from polymer fibers.

The surface of the microparticle may interact with and attach to the capture agent. The surface may naturally interact with the capture agent without functionalisation. The surface of the microparticle is typically functionalised to facilitate attachment of the capture agent. Suitable functionalisations are known in the art. For instance, the surface of the microparticle may be functionalised with a polyhistidine-tag (hexa histidine-tag, 6xHis-tag, His6 tag or His-tag®), Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide, polynucleotide binding proteins (including any of those discussed below), peptides, proteins, antibodies or antibody fragments. Antibody fragments are discussed in more detail below. The microparticle may also be functionalised with other linkers or groups.

The microparticle is preferably paramagnetic or magnetic. The microparticle preferably comprises a paramagnetic or a superparamagnetic material or a paramagnetic or a super-paramagnetic metal, such as iron. Any suitable magnetic microparticle may be used. For instance, magnetic beads commercially available from, for instance, Clontech, Promega, Invitrogen ThermoFisher Scientific and NEB, may be used. In some embodiments, the microparticle comprises a magnetic particle with an organic group such as a metal-chelating group, such as nitrilotriacetic acid (NTA), attached. The organic component may, for instance, comprise a group selected from —C(=O)O—, —C—O—C—, —C(=O)—, —NH—, —C(=O)—NH, —C(=O)—CH$_2$—I, —S(=O)$_2$— and —S—. The organic component may comprise a metal chelating group, such as NTA (nitrilotriacetic acid). Usually, a metal such as gold, iron, nickel or cobalt is also attached to the metal-chelating group. Magnetic beads of this sort are commonly used for capturing His-tagged proteins, but are also suitable for use in the present method.

The microparticle is most preferably a His-Tag Dynabead® which is commercially available from Life Technologies, Mag Strep beads from IBA, Streptavidin magnetic beads from NEB, Solid Phase Reversible Immobilization (SPRI) beads or Agencourt AMPure XP beads from Beckman Coulter or Dynabeads® MyOne™ Streptavidin C1 (ThermoFisher Scientific).

Figure 6:
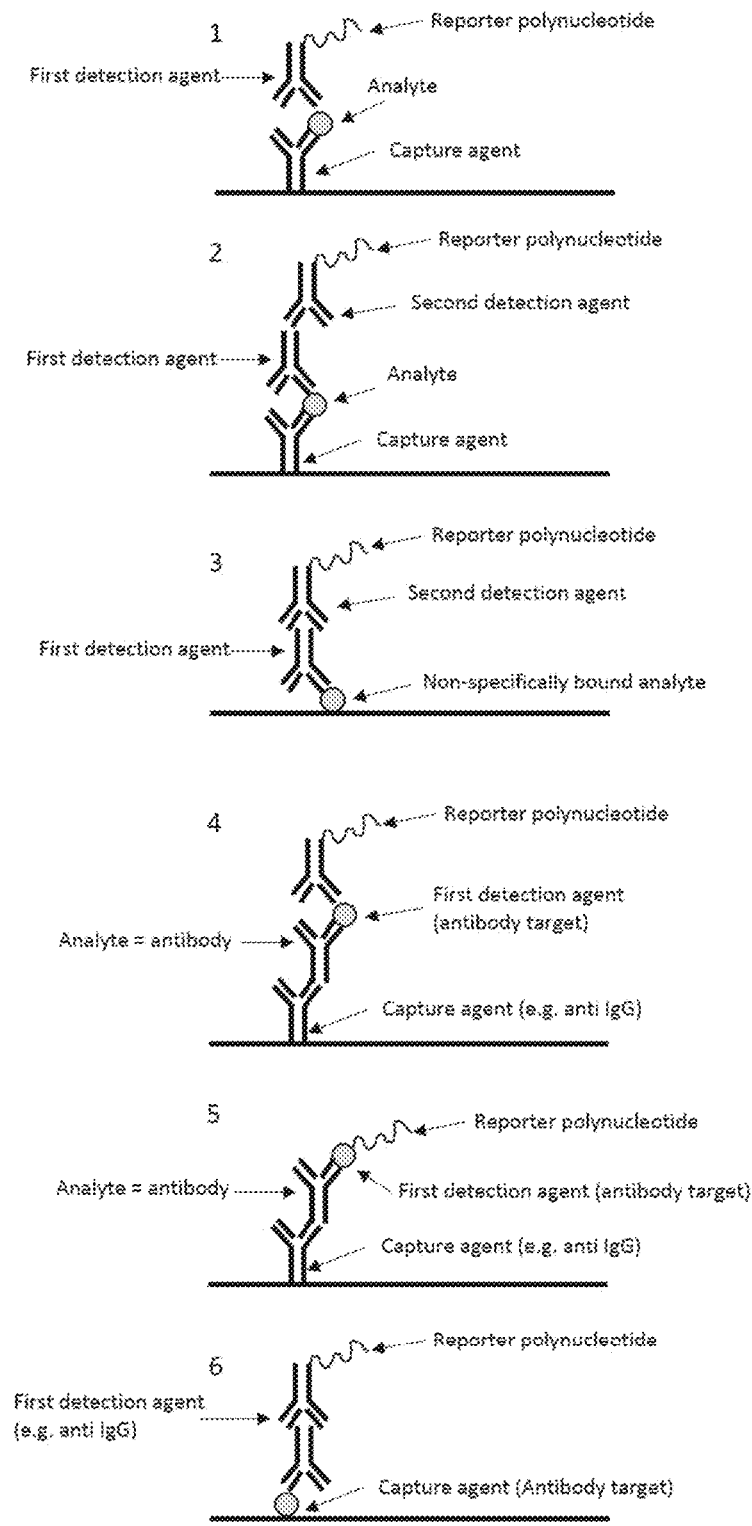
FIG. 6: Examples of different applications of the method.

The method may be carried out using any suitable capture and/or detection agent(s). The skilled person will readily be able to choose suitable agents. The format of the method may be adapted to fit the nature of the target analyte, the purpose of the method, the level of target analyte expected including the relative levels of multiple target analytes, the capture and detection agents used, the surface being used etc. Examples of some suitable assay formats are shown in FIG. 6.

Antibodies

The antibodies used in the method may be a monoclonal or polyclonal. For present purposes, the term "antibody", unless specified to the contrary, includes fragments that specifically bind the relevant target. Such fragments include Fv, F(ab') and F(ab')$_2$ fragments, as well as single chain antibodies. The antibody or fragment thereof may be a chimeric antibody, a CDR-grafted antibody or a humanised antibody. The antibodies can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising an antibody in a host animal against the whole polypeptide or a fragment thereof, for example an antigenic epitope thereof, hereinafter the "immunogen". The fragment may be any of the fragments mentioned herein (typically at least 10 or at least 15 amino acids long). A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Antibodies are also commercially available.

An antibody, or other molecule or group, "specifically binds" to a target when it binds with preferential or high affinity to the target for which it is specific, but does substantially bind, does not bind or binds with only low affinity to other analytes. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific target and its antibody and the measurement of complex formation.

An antibody, or other molecule or group, binds with preferential or high affinity if it binds with a Kd of $1\times10^{-6}$ M or less, more preferably $1\times10^{-7}$ M or less, $5\times10^{-8}$ M or less, more preferably $1\times10^{-8}$ M or less or more preferably $5\times10^{-9}$ M or less. A molecule or group binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

Preferably, the antibody binds the target with an affinity that is at least 10 times, such as at least 50, at least 100, at least 200, at least 300, at least 400, at least 500, at least 1000 or at least 10,000 times, greater than its affinity for other analytes or other molecules. Affinity can be measured using known binding assays, such as those that make use of fluorescence and radioisotopes. Competitive binding assays are also known in the art. The strength of binding can be measured using nanopore force spectroscopy as described in Hornblower et al., Nature Methods. 4: 315-317. (2007).

Reporter Polynucleotides

The reporter polynucleotide may be any of the types of polynucleotide described above. The detection agent may be labelled with any number of reporter polynucleotide molecules, such as 2, 3, 4, 5, 6, 7, 8, 9, 10, 20, 50, 100, 200, 500 or 1000 or more reporter polynucleotide molecules. The more reporter polynucleotide molecules attached to a single detection agent molecule, the greater the amplification of the signal and the lower the concentration of target analyte which may be detected. All of the reporter polynucleotide molecules attached to a single detection agent molecule are preferably identical, or at least comprise the same nucleotide sequence.

The method may comprise specifically labelling two or more target analytes, if present, each with a specific reporter polynucleotide. This means that the method involves labelling a target analyte, if present, with a reporter polynucleotide which is specific for that analyte. The assay is designed so that the first detection agent which specifically binds a first target analyte is labelled (either directly or via a second detection agent) with the reporter polynucleotide specific for that target analyte.

The transmembrane pore is capable of determining any difference between polynucleotides, such as a difference in (i) the length of the polynucleotides, (ii) the identity of the polynucleotides, (iii) the sequences of the polynucleotides, (iv) the secondary structures of the polynucleotides and (v) whether or not the polynucleotides are modified. Any combination of the differences in (i) to (v) may be used to design specific reporter polynucleotides, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Preferably, each reporter polynucleotide has a unique sequence that can be used to detect the corresponding target analyte.

A detection agent is preferably labelled with two or more identical polynucleotides as discussed above. In such embodiments, each detection agent in the panel will be labelled with two or more identical polynucleotides and the polynucleotides will be different between each detection agent. The polynucleotides may be different based on any combination of (i) to (v) discussed above. The specific polynucleotides typically have different sequences. This ensures that each target analyte in the group is labelled with different, i.e. specific, polynucleotides.

The reporter polynucleotide may be single stranded. The reporter polynucleotides are preferably double stranded. The one or more double stranded polynucleotides are preferably linked at one end using a hairpin loop or hairpin loop adaptor. When the one or more double stranded polynucleotides are detected by the pore, the two strands may be interrogated by the pore. Linking and interrogating both strands on a double stranded construct in this way increases the efficiency and accuracy of characterisation. This is well known in the art and described in WO 2013/014451.

Suitable hairpin loops and adaptors can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin adaptor may be provided at either end of the polynucleotide, i.e. the 5' or the 3' end. The hairpin adaptor may be ligated to the polynucleotide using any method known in the art. The hairpin adaptor may be ligated using a ligase, such as T4 DNA ligase, E. coli DNA ligase, Taq DNA ligase, Tma DNA ligase and 9° N DNA ligase.

The two strands of the polynucleotide may be separated using any method known in the art. For instance, they may be separated by a polynucleotide binding protein or using conditions which favour dehybridsation (examples of conditions which favour dehybridisation include, but are not limited to, high temperature, high pH and the addition of agents that can disrupt hydrogen bonding or base pairing, such as formamide and urea).

The hairpin adaptor preferably comprises a selectable binding moiety. This allows the polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the method. In preferred embodiments, the moiety binds to a surface to which no other moiety used in the method binds.

Suitable selective binding moieties are known in the art. Preferred selective binding moieties include, but are not limited to, biotin, a polynucleotide sequence, antibodies, antibody fragments, such as Fab and ScFv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologues sequences. Alternatively, selectable polynucleotide sequences specifically bind to a surface coated with polynucleotide binding proteins.

The hairpin adaptor and/or the selectable binding moiety may comprise a region that can be cut, nicked, cleaved or hydrolysed. Such a region can be designed to allow the polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The reporter polynucleotides may also be provided with a leader sequence which preferentially threads into the pore. The leader sequence facilitates the method. The leader sequence is designed to preferentially thread into the transmembrane pore and thereby facilitate the movement of polynucleotide analyte through the pore. The leader sequence can also be used to link the polynucleotide to the one or more anchors as discussed below.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

If the one or more double stranded polynucleotides comprise a hairpin loop or hairpin loop adaptor at one end, they may comprise a Y adaptor at the other end. The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor may comprise the one or more anchors discussed in more detail above. The Y adaptor preferably comprises a leader sequence which preferentially threads into the pore. Leader sequences are discussed above. The Y adaptor may be ligated to the reporter polynucleotides as discussed above with respect to hairpin loops and hairpin loop adaptors.

The transmembrane pore is typically present in a membrane as discussed in more detail below. The reporter polynucleotides preferably comprise one or more anchors which are capable of coupling to the membrane. The method preferably further comprises coupling the reporter polynucleotides to the membrane using the one or more anchors.

The anchor comprises a group which couples (or binds) to the reporter polynucleotide and a group which couples (or binds) to the membrane. Each anchor may covalently couple (or bind) to the reporter polynucleotide and/or the membrane.

The reporter polynucleotide may be coupled to the membrane using any number of anchors, such as 2, 3, 4 or more anchors. For instance, the reporter polynucleotide may be coupled to the membrane using two anchors each of which separately couples (or binds) to both the reporter polynucleotide and membrane.

The one or more anchors may comprise one or more polynucleotide binding proteins. Each anchor may comprise one or more polynucleotide binding proteins. The polynucleotide binding protein(s) may be any of those discussed below.

If the membrane is an amphiphilic layer, such as a triblock copolymer membrane, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The reporter polynucleotide may be coupled directly to the membrane. The one or more anchors used to couple the reporter polynucleotide to the membrane preferably comprise a linker. The one or more anchors may comprise one or more, such as 2, 3, 4 or more, linkers. One linker may be used to couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The reporter polynucleotide may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the present context, the protein may be present in the membrane or may be used to couple (or bind) to the reporter polynucleotide.

Crosslinkage of polynucleotides can be avoided using a "lock and key" arrangement. Only one end of each linker may react together to form a longer linker and the other ends of the linker each react with the reporter polynucleotide or membrane respectively. Such linkers are described in WO 2010/086602.

The use of a linker is preferred in the sequencing embodiments discussed below. If the reporter polynucleotides are permanently coupled directly to the membrane in the sense that they do not uncouple when interacting with the pore, then some sequence data will be lost as the sequencing run cannot continue to the end of the reporter polynucleotide due to the distance between the membrane and the pore. If a linker is used, then the reporter polynucleotide can be processed to completion.

The coupling may be permanent or stable. In other words, the coupling may be such that the reporter polynucleotides remain coupled to the membrane when interacting with the pore.

The coupling may be transient. In other words, the coupling may be such that the reporter polynucleotides may decouple from the membrane when interacting with the pore. For certain applications, such as aptamer detection and polynucleotide sequencing, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The reporter polynucleotides may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

The reporter polynucleotides are preferably coupled to an amphiphilic layer such as a triblock copolymer membrane or lipid bilayer. Coupling of nucleic acids to synthetic lipid bilayers has been carried out previously with various different tethering strategies. These are summarised in Table 1 below.

TABLE 1

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the reporter polynucleotides to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the reporter polynucleotides. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used. It may also be possible that anchors may be directly added to polynucleotides using terminal transferase with suitably modified nucleotides (e.g. cholesterol or palmitate).

The one or more anchors preferably couple the reporter polynucleotide to the membrane via hybridisation. The hybridisation may be present in any part of the one or more anchors, such as between the one or more anchors and the reporter polynucleotide, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. The one or more anchors may hybridise directly to the reporter polynucleotide, directly to a Y adaptor and/or leader sequence attached to the reporter polynucleotide or directly to a hairpin loop adaptor attached to the reporter polynucleotide (as discussed in more detail above). Alternatively, the one or more anchors may be hybridised to one or more, such as 2 or 3, intermediate polynucleotides (or "splints") which are hybridised to the reporter polynucleotide, to a Y adaptor and/or leader sequence attached to the reporter polynucleotide or to a hairpin loop adaptor attached to the reporter polynucleotide (as discussed in more detail above).

The one or more anchors may comprise a single stranded or double stranded polynucleotide. One part of the anchor may be ligated to a single stranded or double stranded polynucleotide. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatamer or dimer formation) or using "sticky-ends" generated by restriction digestion of the one or more polynucleotides and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the reporter polynucleotides are synthetic strands, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and E. coli Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the reporter polynucleotides are coupled to the membrane without having to functionalise the reporter polynucleotides. This can be achieved by coupling the one or more anchors, such as a polynucleotide binding protein or a chemical group, to the membrane and allowing the one or more anchors to interact with the reporter polynucleotides or by functionalizing the membrane. The one or more anchors may be coupled to the membrane by any of the methods described herein. In particular, the one or more anchors may comprise one or more linkers, such as maleimide functionalised linkers.

The one or more anchors can comprise any group that couples to, binds to or interacts with single or double stranded polynucleotides, specific nucleotide sequences within the polynucleotides or patterns of modified nucleotides within the polynucleotides, or any other ligand that is present on the polynucleotide.

Suitable binding proteins for use in anchors include, but are not limited to, E. coli single stranded binding protein, P5 single stranded binding protein, T4 gp32 single stranded binding protein, the TOPO V dsDNA binding region, human histone proteins, E. coli HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a reporter polynucleotide. The group may intercalate or interact with the reporter polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). The reporter polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2,6-diaminopurine monophosphate).

The one or more anchors may couple to (or bind to) the reporter polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or reporter polynucleotide which form Hoogsteen hydrogen bonds or reversed Hoogsteen hydrogen bonds with the reporter polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the reporter polynucleotide before delivery to the membrane, but the one or more anchors may be contacted with the membrane and subsequently contacted with the reporter polynucleotide.

In another aspect the reporter polynucleotide may be functionalised, using methods described above, so that it can be recognised by a specific binding group. Specifically the reporter polynucleotide may be functionalised with a ligand such as biotin (for binding to streptavidin), amylose (for binding to maltose binding protein or a fusion protein), Ni-NTA (for binding to poly-histidine or poly-histidine tagged proteins) or a peptides (such as an antigen).

The reporter polynucleotide may comprise one or more polynucleotide binding proteins. The polynucleotide binding protein may be any protein that is capable of binding to the polynucleotide and controlling its movement through the transmembrane pore. The protein facilitates the detection of the reporter polynucleotide using the pore.

It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases, translocases and topoisomerases, such as gyrases. Suitable enzymes include, but are not limited to, exonuclease I from *E. coli*, exonuclease III enzyme from *E. coli*, RecJ from *T. thermophilus* and bacteriophage lambda exonuclease, TatD exonuclease and variants thereof. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase or a variant thereof. The topoisomerase is preferably a member of any of the Moiety Classification (EC) groups 5.99.1.2 and 5.99.1.3.

The enzyme is most preferably derived from a helicase. The helicase may be or be derived from a Hel308 helicase, a RecD helicase, such as TraI helicase or a TrwC helicase, a XPD helicase or a Dda helicase. The helicase may be or be derived from Hel308 Mbu, Hel308 Csy, Hel308 Tga, Hel308 Mhu, TraI Eco, XPD Mbu or a variant thereof.

The helicase may be any of the helicases, modified helicases or helicase constructs disclosed in WO 2013/057495; WO 2013/098562; WO2013/098561; WO 2014/013260; WO 2014/013259; WO 2014/013262 and WO/2015/055981).

The helicase preferably is Trwc Cba or a variant thereof, Hel308 Mbu or a variant thereof or Dda or a variant thereof. Variants may differ from the native sequences in any of the ways discussed below for transmembrane pores. A preferred variant of Dda comprises (a) E94C and A360C or (b) E94C, A360C, C109A and C136A and then optionally (ΔM1)G1 (i.e. deletion of M1 and then addition G1). It may also be termed M1G. Any of the variants discussed above may further comprise M1G.

Any number of helicases may be used. For instance, 1, 2, 3, 4, 5, 6, 7, 8, 9, 10 or more helicases may be used. In some embodiments, different numbers of helicases may be used.

The method preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs are described in WO 2014/013260; WO 2014/013259; WO 2014/013262) and WO2015/055981.

A variant of any of the above enzymes is an enzyme that has an amino acid sequence which varies from that any of the above enzymes and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

The enzyme may be covalently attached to the pore. Any method may be used to covalently attach the enzyme to the pore.

A preferred molecular brake is TrwC Cba-Q594A. This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the detection method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Washing Steps

Between the various steps of the method, the surface is typically washed to remove molecules of the reagents which have not bound to the surface and retain only those molecules which have bound to the surface. For instance, the method may involves one or more washing steps. For example, the method may comprise one or more washing steps (i) after contacting the surface having attached thereto a first capture agent which specifically binds to the target analyte with the sample, but before contacting the surface with the first detection agent which specifically binds to the target analyte, (ii) after contacting the surface with the second first detection agent which specifically binds to the target analyte, but before contacting the surface with a detection agent which specifically binds to the first detection agent and/or with the reporter polynucleotide, (iii) after contacting the surface with a second detection agent which specifically binds to the first detection agent, but before contacting the surface with the reporter polynucleotide, and/or (iv) after contacting the surface with the reporter polynucleotide, but before eluting the reporter polynucleotide or before delivering the surface towards a membrane comprising the transmembrane pore.

The washing step is typically performed using the same buffer used throughout the method, but without the relevant components. Any suitable buffer may be used and suitable buffers are known in the art.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the method. The pore may be biological or artificial. Suitable pores include, but are not limited to, protein pores, polynucleotide pores and solid state pores.

Any membrane may be used in the method. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in WO 2009/077734.

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in WO 2009/035647.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method is typically carried out in vitro.

The transmembrane pore is preferably a transmembrane protein pore. A transmembrane protein pore is a polypeptide or a collection of polypeptides that permits hydrated ions, such as analyte, to flow from one side of a membrane to the other side of the membrane. The transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably made up of 6, 7, 8 or 9 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores such as lysenin. α-helix bundle pores comprise a barrel or channel that is formed from α-helices. Suitable α-helix bundle pores include, but are not limited to, inner membrane proteins and a outer membrane proteins, such as WZA, ClyA toxin and FraC. The transmembrane pore may be derived from lysenin. Suitable pores derived from lysenin are disclosed in WO 2013/153359. Suitable pores derived from CsgG are disclosed in WO2016/034591. The transmembrane pore may be derived from Msp or from α-hemolysin (α-HL). The transmembrane protein pore is preferably derived from Msp, preferably from MspA.

Methods are known in the art for inserting pore subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and WO 2006/100484.

The transmembrane pore may be any of the pores disclosed in WO 2015/166275.

The monomers of the pore may be modified to assist their identification or purification, for example by the addition of histidine residues (a his tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomers may be labelled with a revealing label. The revealing label may be any suitable label which allows the pore to be detected. Suitable labels are described above.

The monomers may also be produced using D-amino acids. For instance, the monomer may comprise a mixture of L-amino acids and D-amino acids. This is conventional in the art for producing such proteins or peptides.

The monomer contains one or more specific modifications to facilitate nucleotide discrimination. The monomer may also contain other non-specific modifications as long as they do not interfere with pore formation. A number of non-specific side chain modifications are known in the art and may be made to the side chains of the monomers. Such modifications include, for example, reductive alkylation of amino acids by reaction with an aldehyde followed by reduction with $NaBH_4$, amidination with methylacetimidate or acylation with acetic anhydride.

The monomers can be produced using standard methods known in the art. The monomers derived from Msp may be made synthetically or by recombinant means. For example, the pore may be synthesized by in vitro translation and transcription (IVTT). Suitable methods for producing pores and inserting pores into membranes are discussed WO 2010/004273 WO 2010/004265 and WO 2010/086603. Methods for inserting pores into membranes are also discussed.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Detection Using a Pore

Methods for detecting and characterising reporter polynucleotides using a transmembrane pore are well known in the art. Step (c) of the method preferably may comprises (i) delivering the surface towards a membrane comprising the transmembrane pore, or eluting the reporter polynucleotides from the surface after removing unbound reporter polynucleotides and delivering the eluted reporter polynucleotides to the membrane comprising the transmembrane pore (ii) allowing the reporter polynucleotide(s), if present, to interact with the transmembrane pore such that the reporter polynucleotide moves through the pore, and (ii) taking one or more measurements as the reporter polynucleotide, if present, moves with respect to the pore, wherein the measurements are indicative of the characteristics of the reporter polynucleotides.

The reporter polypeptide may be eluted from the surface by any suitable means. For example, by enzymatic cutting of the reporter polynucleotides, a linker between the polynucleotide and the first or second detection agent or of the first or second digestion agent at a site close to the attachment point of the reporter polynucleotide, digestion of the proteins on the surface and recovering the polynucleotides.

The characteristics, such as sequence, of the reporter polynucleotides are used to determine whether the target analyte is present in the sample and, where there are multiple target analytes, to determine which target analytes are present. The amount of a reporter polynucleotide corresponding to a target analyte detected can be used to determine the amount or abundance of the target analyte in the sample. The concentration of the target analyte can be determined, for example, by using a calibration curve.

Some examples of alternative types of measurement include without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (for example as disclosed in Ivanov A P et al., Nano Lett. 2011 Jan. 12; 11(1):279-85), and FET measurements (for example as disclosed in International Application WO2005/124888). Optical measurements may be combined with electrical measurements (Soni G V et al., Rev Sci Instrum. 2010 January; 81(1):014301). The measurement may be a transmembrane current measurement such as measurement of ion current flow through a transmembrane pore. The ion current may typically be the DC ion current, although in principle an alternative is to use the AC current flow (i.e. the magnitude of the AC current flowing under application of an AC voltage).

Step (c) is preferably carried out with a potential applied across the pore. The applied potential typically causes the reporter polynucleotide to translocate or move through the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The method preferably comprises measuring the current flowing through the pore to detect the reporter polynucleotides.

The current may be measured using any method known in the art. Specific methods are discussed below.

The method comprises delivering the surface, such as one or more microparticles, towards a membrane. The surface (such as one or more microparticles) delivers the reporter polynucleotides, if present, to the transmembrane pore in the membrane. The surface may be delivered towards the membrane in any manner. The method preferably comprises positioning the surface near to or adjacent to the membrane and allowing the surface to move towards the membrane. The surface may be positioned any distance from the membrane, for instance about 500 µm from the membrane or closer, about 200 µm from the membrane or closer, about 100 µm from the membrane or closer, about 50 µm from the membrane or closer or about 30 µm from the membrane or closer.

The surface moves towards the membrane. The surface typically moves to the membrane. The surface may contact the membrane. The surface does not have to contact the membrane. For instance, the surface may not contact the membrane if it is substantially or completely coated with reporter polynucleotides or if substantially all of or all of the surface is attached to the reporter polynucleotides. In some embodiments, the reporter polynucleotides may be larger or longer than the size of the surface or one or more microparticles. The reporter polynucleotides may act as a cushion between the surface and the membrane. The surface moves close enough to the membrane to deliver reporter polynucleotides to the pore. The skilled person can design the system such that the reporter polynucleotides are delivered to the pore.

The one or more microparticles may move towards the membrane in any manner. The method preferably comprises allowing the one or more microparticles to move along an electrochemical gradient, diffusion gradient, hydrophilic gradient or hydrophobic gradient. A gradient is an increase or decrease in the magnitude of a property observed when passing from one point or moment to another. The skilled person will understand how to generate any of the gradients mentioned above and how to get one or more microparticles to move along them. For instance, a charged microparticle will typically move along an electrochemical gradient. A microparticle will typically diffuse towards the membrane. A microparticle will typically flow in solution along a pressure gradient. A hydrophilic or hydrophobic microparticle will typically move along a hydrophilic or hydrophobic gradient. The reporter polynucleotide, antibodies and any associated molecule, such as the one or more anchors, may affect the charge and/or hydrophilicity/hydrophobicity of the one or more microparticles.

The method preferably comprises allowing the one or more microparticles to move within a magnetic field. The method preferably comprises using a magnetic field to deliver the one or more microparticles to the membrane. Magnetic microparticles are discussed above. Suitable methods are known for creating magnetic fields and include, but are not limited to, magnetic materials or electromagnets.

The method preferably comprises allowing the one or more microparticles to move within an electrical field. The method preferably comprises using an electrical field to deliver the one or more microparticles to the membrane. Charged microparticles are known in the art and discussed above. Suitable methods are known for creating electrical fields also known.

The method preferably comprises allowing the one or more microparticles to move under pressure. The method preferably comprises using pressure or flow to deliver the one or more microparticles to the membrane. The pressure may be physical pressure or osmotic pressure. Suitable methods are known for creating such pressures.

The method preferably comprises allowing the one or more microparticles to move within a gravitational field or with gravity. The method preferably comprises using gravity to deliver the one or more microparticles to the membrane. A dense microparticle placed above a membrane in solution will move towards the membrane under the influence of gravity. The method may comprise allowing the one or more microparticles to travel, move, slide or roll along a surface towards the membrane. The surface typically slopes away from the vertical walls of a chamber comprising the membrane (where the walls are approximately perpendicular to the plane of the membrane) at an angle of about 45° to about 69°. The surface typically slopes towards the membrane at an angle of about 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44° to about 45° compared with the plane of the membrane. In a preferred embodiment, the sloping surface is formed by pre-treatment of one or more surfaces of a chamber comprising the membrane with a suitable pre-treatment, such as silicon oil, AR20 or hexadecane. Suitable apparatuses comprising chambers for use in the method are discussed below.

If the one or more microparticles contacts the membrane, the method may comprise allowing the microparticle(s) to travel, move, slide or roll along the membrane. If the one or more microparticles do not contact the membrane, the method may comprise allowing the microparticle(s) to travel, move, slide or roll in parallel with the membrane.

Apparatus and Conditions

Electrical measurements may be made using standard single channel recording equipment as describe in Stoddart, D. S., et al., (2009), *Proceedings of the National Academy of Sciences of the United States of America* 106, p 7702-7707, Lieberman K R et al, J Am Chem Soc. 2010; 132(50):17961-72, and International Application WO-2000/28312. Alternatively, electrical measurements may be made using a multi-channel system, for example as described in WO2009/077734 and WO2011/067559.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in WO 2008/102120.

The methods involve measuring the current flowing through the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods may be carried out on a silicon-based array of wells where each array comprises 128, 256, 512, 1024 or more wells.

The methods may involve the measuring of a current flowing through the pore. Suitable conditions for measuring ionic currents through transmembrane pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of binding/no binding to be identified against the background of normal current fluctuations.

The methods are typically carried out in the presence of a buffer. In the exemplary apparatus discussed above, the buffer is present in the aqueous solution in the chamber. Any buffer may be used in the method. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Methods of Measuring Concentration

The method preferably further comprises, for those target analytes that are present, measuring the number of reporter polynucleotides detected with the transmembrane pore. This helps to determine the concentration of the analyte(s) present in the sample, generally by reference to a calibration curve, use of equilibrium constants or reference to control data. Methods for calculating the concentration are well known in the art.

Also provided is a method of determining in a sample the concentration of a target analyte, the method comprising:

(i) carrying out steps (a) to (c) of the method of determining the presence or absence of a target analyte in a sample; and (ii) if the target analyte is shown to be present in the sample comparing the number of reporter polynucleotides detected using the pore with control or reference data for the target analyte and thereby determining the concentration of the target analyte in the sample.

Control or reference data can be generated by conducting control experiments in which known concentrations of an analyte member are used to calibrate the assay. The calibration experiments are typically carried out using the same components and under the same conditions, especially component concentration, as the experimental assay.

Products and Kits

Also provided is an antibody labelled with a reporter polynucleotide, wherein the reporter polynucleotide is adapted for analysis using a transmembrane pore. Preferably, the reporter polynucleotide is double stranded and comprises a double stranded polynucleotide adapter an one end. For example the adapter may comprise a site in one of the strands that can be cut with an enzyme to release the reporter polynucleotide from the antibody such that a single stranded end is available to interact with a transmembrane pore. The antibody may be any of those discussed above. The antibody typically specifically binds to a target analyte or an antibody which specifically binds a target analyte. The antibody may be labelled with the reporter polynucleotides using streptavidin, or the reporter may be attached to the antibody by any of the means disclosed herein. The antibody may be labelled with any number of polynucleotides as discussed above. The reporter polynucleotide may be any of those discussed above.

Also provided is a panel of two or more antibodies as disclosed herein.

Also provided is a kit carrying out the disclosed method. The kit comprises a capture agent which specifically binds the target analyte, a detection agent which specifically binds the target analyte and a reporter polynucleotide. The reporter polynucleotide may be attached to the first detection agent. The kit may further comprise streptavidin and/or the reporter polynucleotide and the first detection agent may be biotinylated.

Also provided is a kit comprising a panel of two or more detection agents, such as antibodies, each of which specifically binds to a different target analyte and a panel of reporter polynucleotides, wherein each reporter nucleotide is different, e.g. comprises a unique nucleotide sequence, and, optionally, two or more second detection agents, such as antibodies, that specifically bind to one first detection agent in the panel. The reporter polynucleotides may be attached to the first detection agents, or optionally to the second detection agents.

The kit may further comprise (a) a panel of two or more capture agents which each specifically binds to a different target analyte, which capture agents may be attached to one or more surfaces. The kit may further comprise a surface.

If the surface comprises one or more microparticles, the different capture agents in the panel may be combined on the same microparticle. Alternatively, the different capture agents in the panel may be on different microparticles.

The panels of capture agents and first detection agents are preferably different, for example are different. Preferably each panel comprises an antibody to each one of the target analytes where the antibody to the target analyte in the panel of capture agents is different from the antibody to the same target analyte in the panel of detection agents.

The kits preferably further comprise a surface, such as one or more microparticles. The capture agent(s) are preferably attached to the surface.

Any of the embodiments discussed above with reference to the methods equally apply to the panels and kits.

The kit may further comprise the components of a membrane, such as the phospholipids needed to form an amphiphilic layer, such as a lipid bilayer.

The kits may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above, a transmembrane pore or voltage or patch clamp apparatus. Reagents may be present in the kit in a dry state such that a fluid sample resuspends the reagents. The kit may also, optionally, comprise instructions to enable the kit to be used in the method disclosed herein or details regarding which patients the method may be used for. The kit may, optionally, comprise nucleotides.

EXAMPLE 1

This Example demonstrates how a combination of an enzyme-linked immunosorbent assay (ELISA) and sequencing of barcoded polynucleotides on a MinION can be used to indicate the presence and concentration of the protein Prostate-Specific Antigen (PSA) in a sample.

Materials and Methods

The Human PSA ELISA Kit (KLK3) (Abcam, ab113327) was selected for use in detection of PSA. The protein standard dilution series was used as an indicator of whether barcoded biotinylated reporter polynucleotides can be used for concentration-dependent protein detection. The initial ELISA protocol steps differed little from Abcam's kit protocol. One strip of 8 wells was prepared. The protein standards were prepared as instructed in Abcam's kit protocol. This resulted in the following concentrations of proteins, which were each assigned a barcoded reporter polynucleotide (see polynucleotide sequences; all oligonucleotides synthesised by IDT) in preparation for reporter binding at the end of the protocol:

TABLE 1

| Well | concentration of protein standard (pg/ml) added to each ELISA well. | |
|---|---|---|
| | Prostate-specific antigen (PSA) protein standard concentration (pg/ml) | Reporter Polynucleotide Sequence |
| 1 | 100000 | SEQ ID NO: 1 |
| 2 | 50000 | SEQ ID NO: 2 |
| 3 | 25000 | SEQ ID NO: 3 |
| 4 | 12500 | SEQ ID NO: 4 |
| 5 | 6250 | SEQ ID NO: 5 |
| 6 | 3125 | SEQ ID NO: 6 |
| 7 | 1563 | SEQ ID NO: 7 |
| 8 | 0 | SEQ ID NO: 8 |

PSA was detected using the following protocol:

1. Prepare reagents as described in detail in Abcam protocol.
2. Prepare PSA standards as described in detail in Abcam protocol. Here, diluted standards in assay diluent A.
3. Add standards:
    a. Add 100 µl standard per well of an 8-well ELISA plate, adding one standard dilution per well. Cover wells and incubate for 2.5 hours at room temperature with gentle agitation.
4. Wash:
    a. Discard solution.
    b. Add 300 µl 1× wash solution (Human PSA ELISA Kit (KLK3), Abcam, ab113327). Discard wash solution.
    c. Repeat (b) for a total of 4 washes.
    d. Remove any residual wash solution.
5. Add Biotinylated PSA Detection Antibody:
    a. Dilute 80× stock Biotinylated PSA Detection Antibody (Human PSA ELISA Kit (KLK3), Abcam, ab113327) to 1× with 1× Assay Diluent B (Human PSA ELISA Kit (KLK3), Abcam, ab113327).
    b. Add 100 µl 1× Detection Antibody to each well, cover wells and incubate for 1 hour at room temperature with gentle agitation.
6. Wash (as step 5).
7. Add Streptavidin:
    a. Dilute Streptavidin (Streptavidin from *Streptomyces avidinii*, Sigma-Aldrich, S4762) to 40 ng/µl with 1× PBS (Phosphate buffered saline 10×, Sigma-Aldrich, P5493).
    b. Add 50 µl 40 ng/ul Streptavidin in PBS to each well. Cover wells and incubate for 50 minutes at room temperature with gentle agitation.
8. Wash (as step 5).
9. Add barcoded reporters (see polynucleotide sequences for barcode reporter polynucleotide assigned to each well. All oligonucleotides synthesised by IDT.):
    a. Assign one barcoded reporter to each well. Dilute each to 80 ng in 50 µl 1× TE (TE buffer (20×), ThermoFisher Scientific, T11493).
    b. Add one 50 µl barcoded reporter polynucleotide sample to each appropriate well. Cover wells and incubate for 30 minutes with gentle agitation.
10. Wash (as step 5).
11. Elute barcoded reporters:
    a. Prepare a solution containing 1 µl USER™ Enzyme (USER™ Enzyme, NEB, M5505) in 50 µl 1× PBS per well.
    b. Add 50 µl USER™/TE solution per well, cover wells and incubate for 20 minutes at 37° C. with agitation.
    c. Pool all eluted samples in a 1.5 ml DNA LoBind tube (Eppendorf® LoBind microcentrifuge tubes, Sigma-Aldrich, Z666548) to form one 400 µl sample.

d. SPRI clean:
   i. Add 400 µl Agencourt AMPure XP DNA SPRI beads (Agencourt AMPure XP, Beckman-Coulter, A63880), incubate for 5 minutes at room temperature with agitation. Pellet beads by placing tube on a magnetic rack.
   ii. Wash twice with 200 µl 70% ethanol.
   iii. Spin down and re-pellet beads, remove residual wash, dry pellet at room temperature for 5-10 minutes.
   iv. Elute in 51 µl nuclease-free water (Nuclease-Free Water, ThermoFisher Scientific, AM9937) for 5 minutes at room temperature. Pellet beads, collect eluted sample.

12. Ligate adapters in preparation for sequencing:
   a. Combine the following in a 1.5 ml DNA LoBind tube (Eppendorf):
      50 µl barcoded reporter pool
      20 µl 1D Barcode Adapter Mix (BAM) (Native Barcoding Kit 1D, Oxford Nanopore Technologies, EXP-NBD103)
      20 µl NEBNext T4 Quick ligation buffer (NEBNext® Quick Ligation Module, NEB, E6056)
      10 µl NEBNext T4 Quick ligase (NEBNext® Quick Ligation Module, NEB, E6056)
   b. Incubate for 10 minutes at room temperature.
   c. Clean up with SPRI beads:
      i. Add 40 µl Agencourt AMPure XP DNA SPRI beads, incubate for 5 minutes at room temperature with agitation. Pellet beads by placing tube on a magnetic rack. Remove supernatant.
      ii. Add 140 µl Adapter Bead Binding Buffer (ABB) (Ligation Sequencing Kit 1D, Oxford Nanopore Technologies, SQK-LSK108), flick tube to mix. Pellet beads and remove buffer.
      iii. Add 25 µl Elution Buffer (ELB) (Ligation Sequencing Kit 1D, Oxford Nanopore Technologies, SQK-LSK108) and mix. Incubate for 10 minutes at room temperature. Pellet beads and collect eluted library.

13. Prepare the adapted library for loading on to Flow Cells:
   a. Combine the following, in duplicate:
      12 µl eluted adapter-ligated library
      25.5 µl library loading beads (LLB) (Library Loading Bead Kit, Oxford Nanopore Technologies, EXP-LLB001)
      37.5 µl Running buffer (RBF) (Ligation Sequencing Kit 1D, Oxford Nanopore Technologies, SQK-LSK108)
   b. Load one 75 µl sample per SpotON Mk I (R9.4) Flow Cell (Oxford Nanopore Technologies, FLO-MIN106), set up on MinIONs (MinION Mk 1B, Oxford Nanopore Technologies) and primed as described in the protocol 1D Native barcoding genomic DNA (with EXP-NBD103 and SQK-LSK108) (Oxford Nanopore Technologies).
   c. Sequence for 19 hours. Basecall sequencing data via the EPI2ME platform (Metrichor Ltd).

Discussion

Sequencing data demonstrated that a higher PSA concentration is correlated with a higher number of reads of the associated barcoded reporter polynucleotide. This indicates that this combination of ELISA and barcode sequencing allows for concentration-dependent protein detection.

PSA is used as a biomarker in screening for prostate cancer; there is some disagreement regarding cut-off PSA levels for referral recommendation, but an age-dependent threshold starting at 3 ng/ml is recommended by The National Institute for Health and Care Excellence (NICE). This demonstrates that protein detection via sequencing is within the required range for this test.

EXAMPLE 2

This Example illustrates that a combination of an enzyme-linked immunosorbent assay (ELISA) and sequencing of barcoded polynucleotides on a MinION can be used to indicate the presence and concentrations of several proteins in multiplex.

Materials and Methods

The following three ELISA kits were used to test concentration-dependent multiplex protein detection for the specified three proteins:
   Human PSA ELISA Kit (KLK3) (Abcam, ab113327)
   Human Retinol binding protein ELISA Kit (RBP) (Abcam, ab108899)
   Human alpha 1 Antitrypsin ELISA Kit (SERPINA1) (Abcam, ab108799)

The protein standard dilution series for each kit was used as an indicator of whether barcoded biotinylated "reporter" polynucleotides can be used for concentration-dependent protein detection in multiplex.

One strip of 8 wells was prepared per kit. For each, the protein standards were prepared as instructed in each protocol (n.b. diluents and concentrations vary protocol to protocol). This resulted in the following concentrations of proteins, which were each assigned a barcoded reporter polynucleotide (see polynucleotide sequences; all oligonucleotides synthesised by IDT) in preparation for reporter binding at the end of the protocol:

TABLE 2 concentration of protein standard (pg/ml) added to each ELISA well.

| | Prostate-specific antigen (PSA) | | Retinol binding protein (RBP) | | alpha-1 antitrypsin (AAT) | |
|---|---|---|---|---|---|---|
| Well | Conc pg/ml | Reporter Polynucleotide | Conc pg/ml | Reporter Polynucleotide | Conc pg/ml | Reporter Polynucleotide |
| 1 | 2500 | SEQ ID NO: 9 | 500000 | SEQ ID NO: 17 | 100000 | SEQ ID NO: 25 |
| 2 | 1000 | SEQ ID NO: 10 | 250000 | SEQ ID NO: 18 | 25000 | SEQ ID NO: 26 |
| 3 | 400 | SEQ ID NO: 11 | 125000 | SEQ ID NO: 19 | 6250 | SEQ ID NO: 27 |
| 4 | 160 | SEQ ID NO: 12 | 63000 | SEQ ID NO: 20 | 1563 | SEQ ID NO: 28 |
| 5 | 64 | SEQ ID NO: 13 | 31000 | SEQ ID NO: 21 | 391 | SEQ ID NO: 29 |
| 6 | 25.6 | SEQ ID NO: 14 | 16000 | SEQ ID NO: 22 | 97.65 | SEQ ID NO: 30 |
| 7 | 10.24 | SEQ ID NO: 15 | 8000 | SEQ ID NO: 23 | 24.41 | SEQ ID NO: 31 |
| 8 | 0 | SEQ ID NO: 16 | 0 | SEQ ID NO: 24 | 0 | SEQ ID NO: 32 |

PSA, RBP and AAT were detected using the following protocol:

1. Prepare reagents as described in detail in individual kit protocols.
2. Prepare standards as described in detail in individual kit protocols. Here, diluted PSA standards in assay diluent A (option of A or B) and RBP/AAT standards in diluent N provided in respective kits.
3. Add standards:
   a. Add (100 µl for PSA, 50 µl for RBP and AAT) standard per well of an 8-well ELISA plate. Cover wells and incubate at 4° C. overnight, then incubate for 2.5 hours at room temperature with gentle agitation.
4. Wash:
   a. Discard solution.
   b. Add (300 µl for PSA, 200 µl for RBP and AAT) 1× appropriate wash solution provided in each ELISA kit. Discard wash solution.
   c. Repeat (b) for a total of (4 washes for PSA, 5 washes for RBP and AAT).
   d. Remove any residual wash solution.
5. Add specified Biotinylated Detection Antibody:
   a. Dilute required detection antibody specific to each protein as described in relevant kit protocols.
   b. Add (100 µl for PSA, 50 µl for RBP/AAT) 1× Detection Antibody to each well, cover wells and incubate for 1 hour at room temperature with gentle agitation.
6. Wash (as step 5).
7. Add Streptavidin:
   a. Dilute Streptavidin (Streptavidin from *Streptomyces avidinii*, Sigma-Aldrich, S4762) to 40 ng/µl with 1× PBS (Phosphate buffered saline 10×, Sigma-Aldrich, P5493).
   b. Add 50 µl ng/µl Streptavidin to each well. Cover wells and incubate for 50 minutes at room temperature with gentle agitation.
8. Wash (as step 5).
9. Add barcoded reporters (see polynucleotide sequences for barcode reporter polynucleotide assigned to each well. All oligonucleotides synthesised by IDT.):
   a. Assign one barcoded reporter to each well. Dilute each to 80 ng in 50 µl 1× TE (TE buffer (20×), ThermoFisher Scientific, T11493).
   b. Add one 50 µl barcoded reporter sample to each appropriate well. Cover wells, incubate at 4° C. overnight, then incubate for 30 minutes at room temperature with gentle agitation.
10. Wash (as step 5).
11. Elute barcoded reporters:
    a. Prepare a solution containing 1 µl USER™ Enzyme (USER™ Enzyme, NEB, M5505) in 50 µl 1× PBS per well.
    b. Add 50 µl USER™/TE solution per well, cover wells and incubate for 20 minutes at 37° C. with agitation.
    c. Pool all eluted samples in a 1.5 ml DNA LoBind tube (Eppendorf® LoBind microcentrifuge tubes, Sigma-Aldrich, Z666548) to form one 1.2 ml pooled sample. Split between two 1.5 ml DNA LoBind tubes to form two 600 µl samples.
    d. SPRI clean:
       i. Add 600 µl Agencourt AMPure XP DNA SPRI beads (Agencourt AMPure XP, Beckman-Coulter, A63880) to each sample and incubate for 5 minutes at room temperature with agitation. Pellet beads by placing tubes on a magnetic rack.
       ii. Wash twice with 200 µl 170% ethanol.
       iii. Spin down and re-pellet beads, remove residual wash, dry pellets at room temperature for 5-10 minutes.
       iv. Elute each sample in 26 µl nuclease-free water (Nuclease-Free Water, ThermoFisher Scientific, AM9937) for 5 minutes at room temperature. Pellet beads, collect and combine eluted samples to form one barcoded reporter pool.
12. Ligate adapters in preparation for sequencing:
    a. Combine the following in a 1.5 ml DNA LoBind tube (Eppendorf):
       50 µl barcoded reporter pool
       20 µl 1D Barcode Adapter Mix (BAM) (Native Barcoding Kit 1D, Oxford Nanopore Technologies, EXP-NBD103)
       20 µl NEBNext T4 Quick ligation buffer (NEBNext® Quick Ligation Module, NEB, E6056)
       10 µl NEBNext T4 Quick ligase (NEBNext® Quick Ligation Module, NEB, E6056)
    b. Incubate for 10 minutes at room temperature
    c. Clean up with SPRI beads:
       i. Add 40 µl Agencourt AMPure XP DNA SPRI beads, incubate for 5 minutes at room temperature with agitation. Pellet beads by placing tube on a magnetic rack. Remove supernatant.
       ii. Add 140 µl Adapter Bead Binding Buffer (ABB) (Ligation Sequencing Kit 1D, Oxford Nanopore Technologies, SQK-LSK108), flick tube to mix. Pellet beads and remove buffer.
       iii. Add 25 µl Elution Buffer (ELB) (Ligation Sequencing Kit 1D, Oxford Nanopore Technologies, SQK-LSK108) and mix. Incubate for 10 minutes at room temperature. Pellet beads and collect eluted library.
13. Prepare the adapted library for loading on to Flow Cells:
    a. Combine the following, in duplicate:
       12 µl eluted adapter-ligated library
       25.5 µl library loading beads (LLB) (Library Loading Bead Kit, Oxford Nanopore Technologies, EXP-LLB001)
       37.5 µl Running buffer (RBF) (Ligation Sequencing Kit 1D, Oxford Nanopore Technologies, SQK-LSK108)
    b. Load one 75 µl sample per SpotON Mk I (R9.4) Flow Cell (Oxford Nanopore Technologies, FLO-MIN106), set up on MinIONs (MinION Mk 1B, Oxford Nanopore Technologies) and primed as described in the protocol *1D Native barcoding genomic DNA (with EXP-NBD103 and SQK-LSK108)* (Oxford Nanopore Technologies).
    c. Sequence for 48 hours. Basecall sequencing data via the EPI2ME platform (Metrichor Ltd).

Discussion

Figure 2:
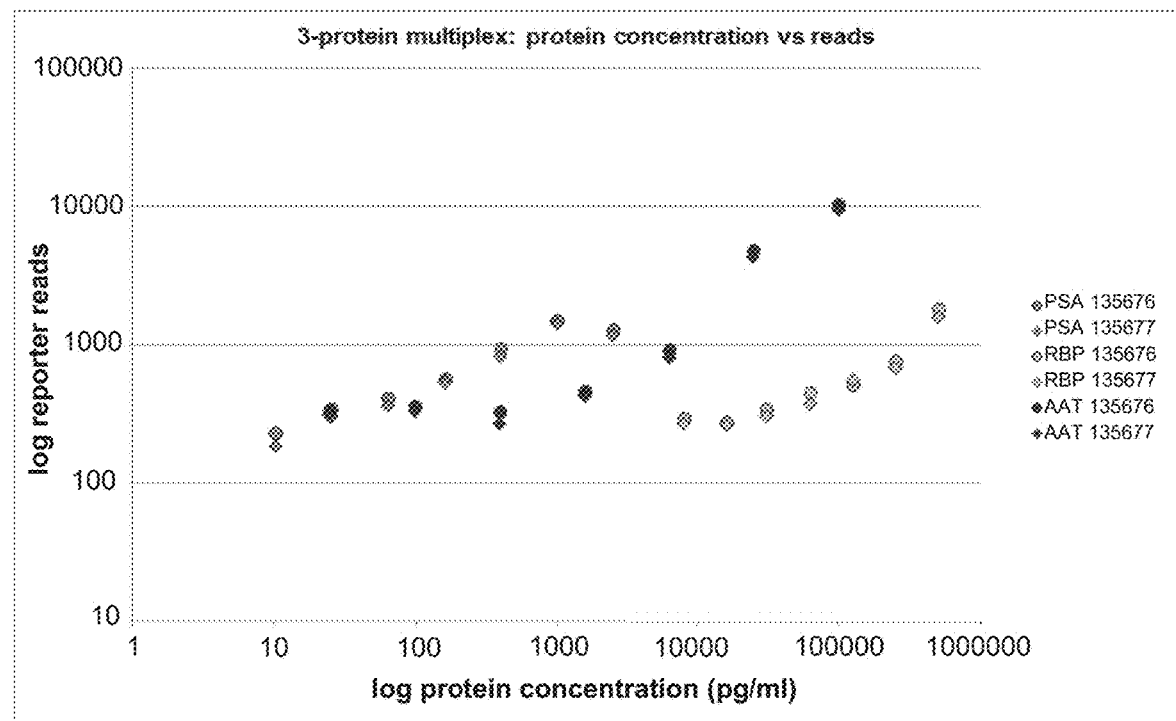
FIG. 2: Sequencing results for two Flow Cell runs of the barcoded reporter polynucleotide pool collected from the PSA, RBP and AAT ELISA well strips. The concentration of protein (pg/ml) added to each ELISA well is correlated with the number of reads in sequencing for the barcoded reporter polynucleotide associated with that well. Concentration dependence is observed for each of the three proteins detected in multiplex.
Figure 3A:
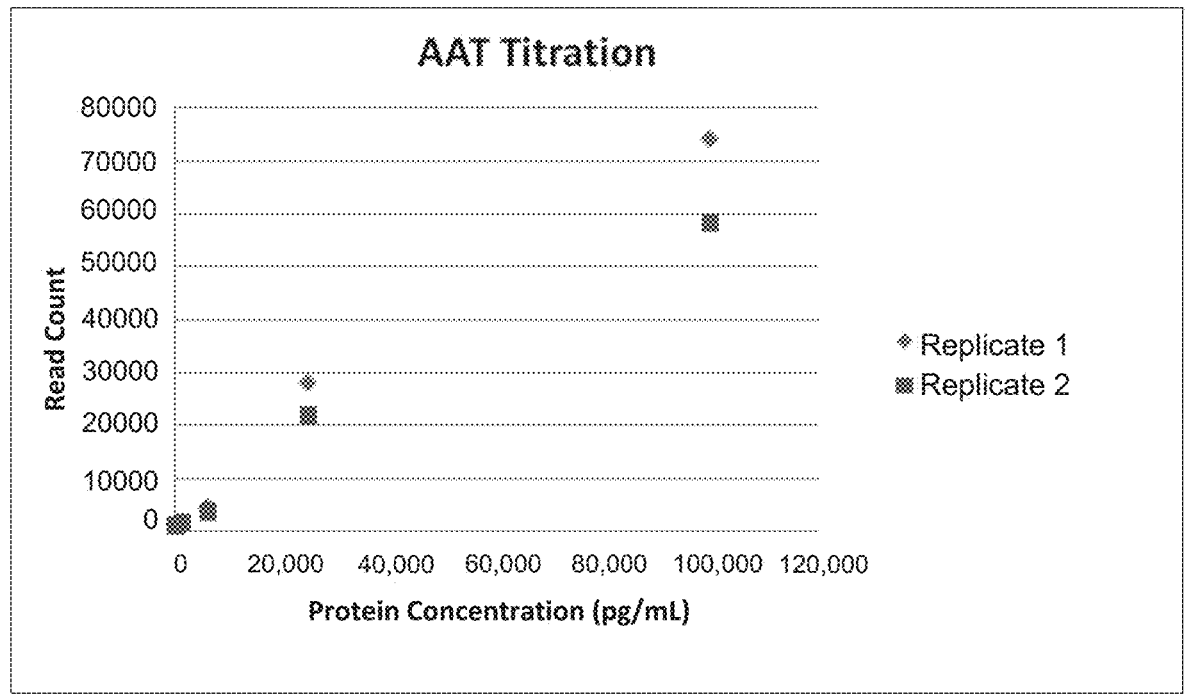
FIGS. 3A-3D: Sequencing results for two Flow Cell runs of the barcoded reporter polynucleotide pool collected from the AAT (FIG. 3A), CEA (FIG. 3B), RBP (FIG. 3C) and SCC (FIG. 3D) ELISA well strips. The concentration of protein (pg/ml) added to each ELISA well is correlated with the number of reads in sequencing for the barcoded reporter polynucleotide associated with that well. Concentration dependence is observed for each of the four proteins detected in multiplex.
Figure 3B:
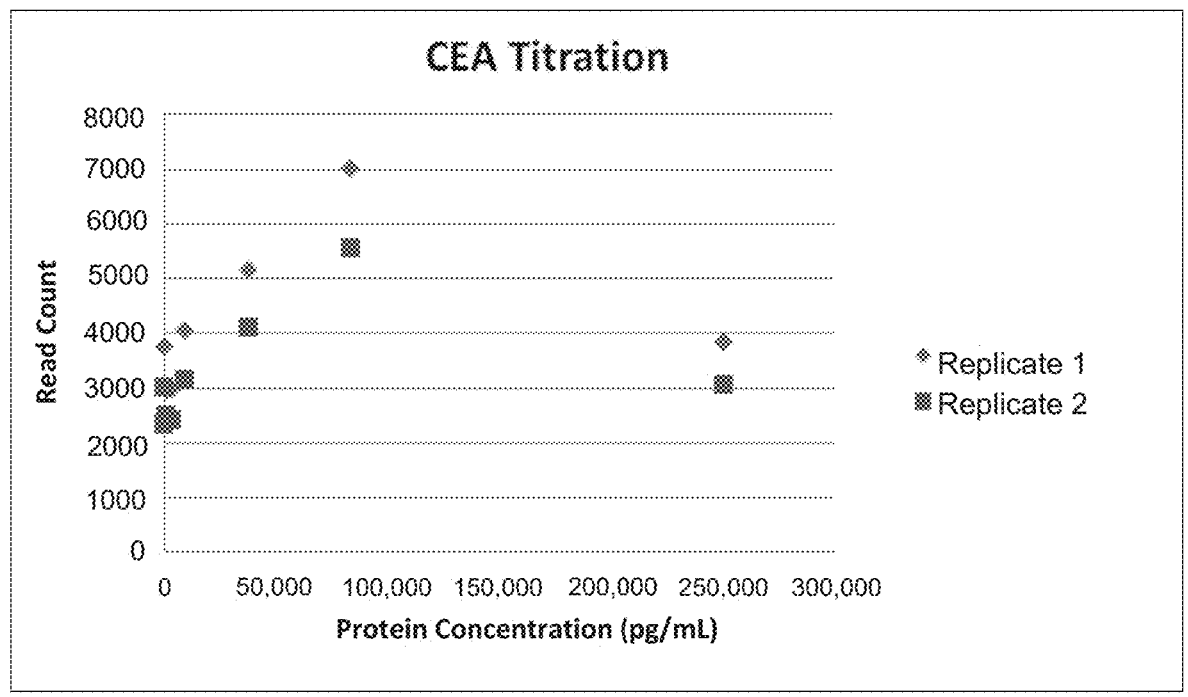
Figure 3C:
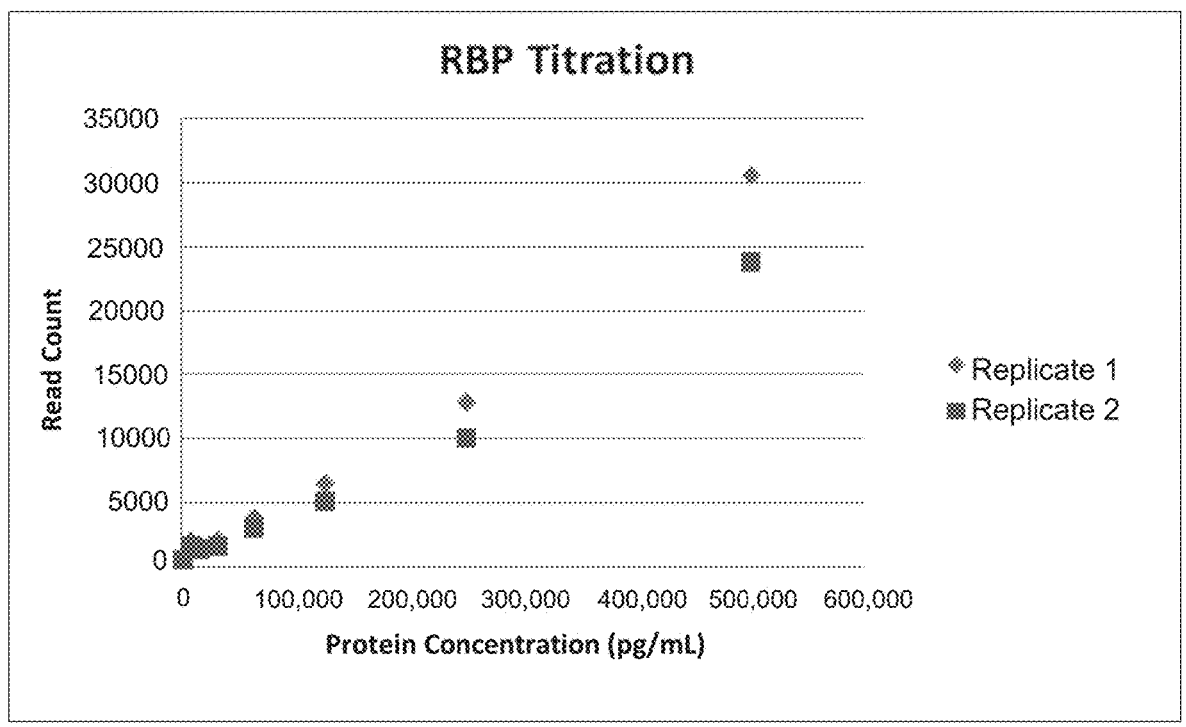
Figure 3D:
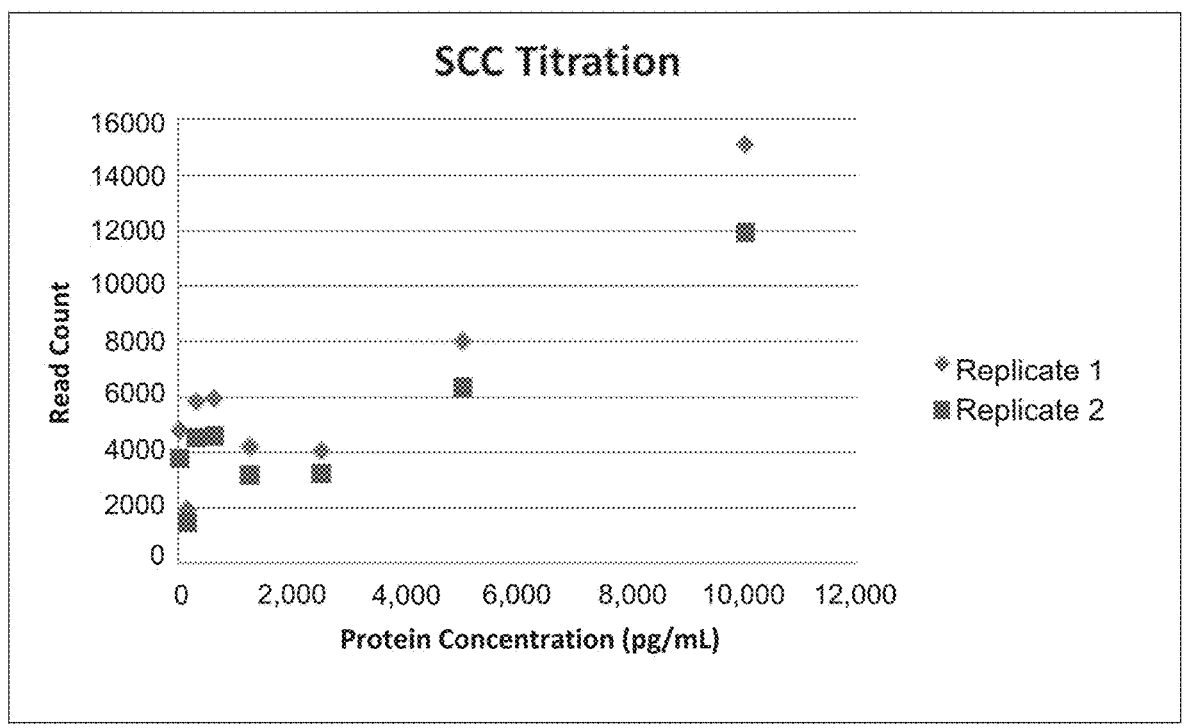
Figure 4:
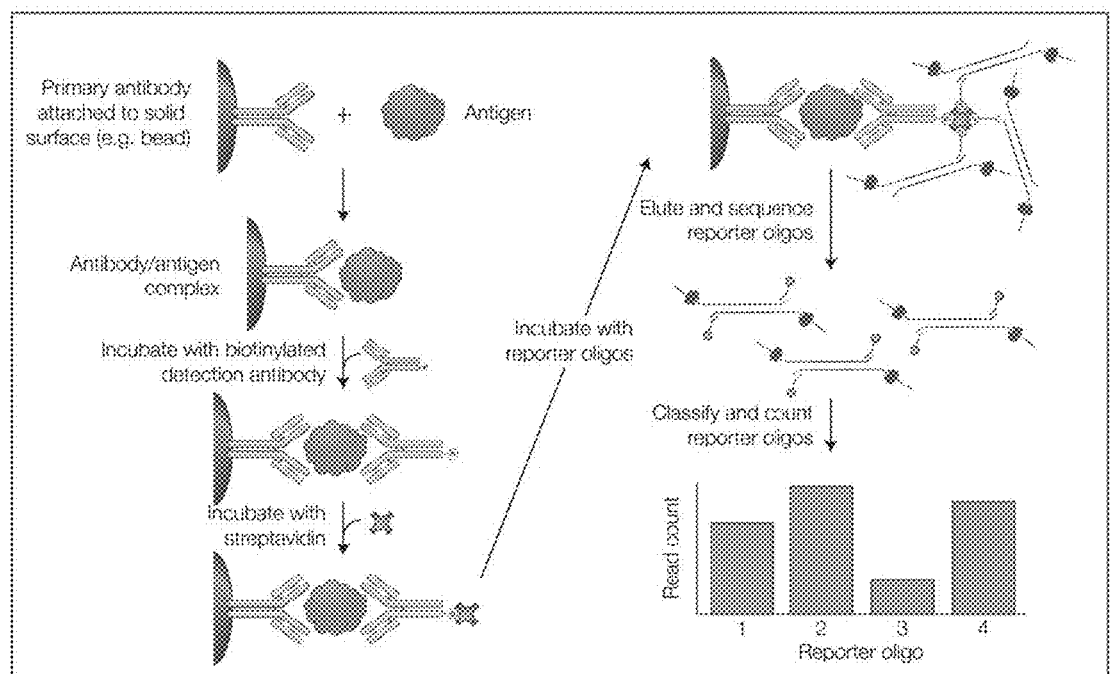
FIG. 4: Workflow diagram for nanopore protein quantification. An adapted version of a sandwich ELISA utilising a secondary antibody which has a biotin group attached to the free end of one heavy chain. Following antibody/antigen complex formation streptavidin is added. Streptavidin is capable of binding four biotin groups meaning that when a streptavidin molecule binds to a heavy chain, an average of three binding sites are still available. Reporter polynucleotides are then added to these available binding sites.
Figure 5:
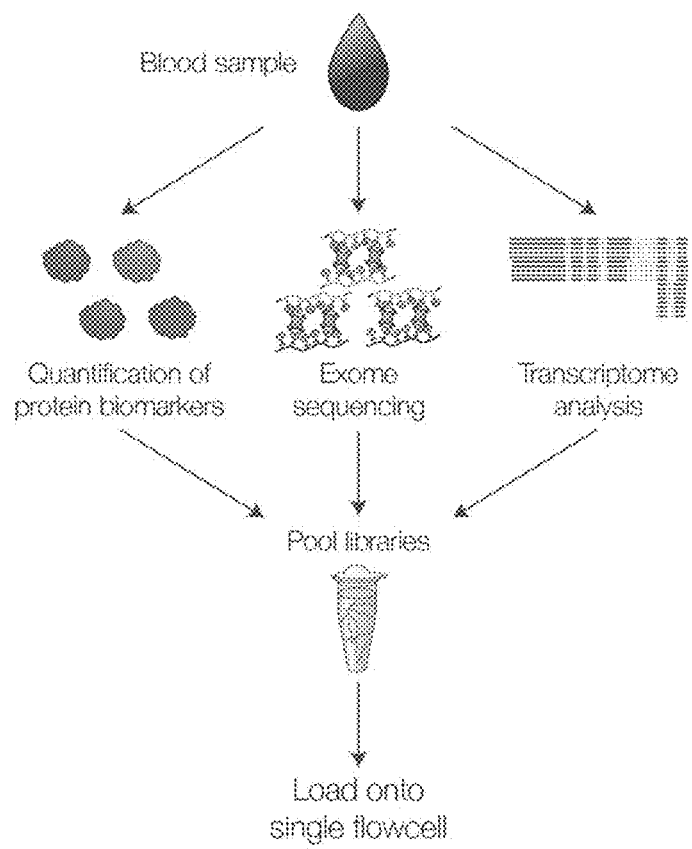
FIG. 5: Combined testing of biomarker proteins, transcriptome and exome on a single flow cell. The relatively low number of reporter reads needed for sensitive protein quantification means that a large biomarker panel can be quantified on a single flow cell while the same flow cell is used to sequence that subject's exome and transcriptome simultaneously. This could be used to provide a comprehensive assessment of the status of a subject's health.

Sequencing data (FIG. 2) indicates that higher protein concentration is correlated with higher numbers of reads of the associated barcoded reporter polynucleotide. Concentration-dependent detection was present for all three proteins. This demonstrates that this protocol can be used for concentration-dependent detection of a panel of proteins in multiplex.

EXAMPLE 3

This Example demonstrates that a combination of an enzyme-linked immunosorbent assay (ELISA) and sequencing of barcoded polynucleotides on a MinION can be used to determine the presence and concentration of a panel of proteins of clinical interest in multiplex.

Materials and Methods

A four-protein lung cancer biomarker panel as identified in *Panel of Serum Biomarkers for the Diagnosis of Lung Cancer* (Patz et al., J Clin Oncol. 2007 December) was selected for multiplex detection.

The following ELISA kits were selected for detection of the four specified proteins of interest:

AAT: Abcam Human alpha 1 Antitrypsin ELISA Kit (SERPINA1) (ab108799)
CEA: Abcam Human Carcino Embryonic Antigen ELISA Kit (CEA) (ab99992)
RBP: Abcam Human Retinol binding protein ELISA Kit (RBP) (ab108899)
SCC: RayBio Human Serpin B3/SCCA1 ELISA kit (ELH-SERPINB3-1)

For each, the protein standards were prepared as instructed in each ELISA kit protocol (n.b. diluents and concentrations vary protocol to protocol). This resulted in the following concentrations of proteins, which were each assigned a barcoded reporter polynucleotide (see polynucleotide sequences; all oligonucleotides synthesised by IDT) in preparation for reporter binding at the end of the protocol:

TABLE 3 concentration of protein standard (pg/ml) added to each ELISA well.

| Well | alpha-1 antitrypsin (AAT) Conc pg/ml | Reporter Polynucleotide | Carcino Embryonic Antigen (CEA) Conc pg/ml | Reporter Polynucleotide |
|---|---|---|---|---|
| 1 | 100000 | SEQ ID NO: 33 | 250000 | SEQ ID NO: 41 |
| 2 | 50000 | SEQ ID NO: 34 | 83330 | SEQ ID NO: 42 |
| 3 | 25000 | SEQ ID NO: 35 | 37780 | SEQ ID NO: 43 |
| 4 | 12500 | SEQ ID NO: 36 | 9259 | SEQ ID NO: 44 |
| 5 | 6250 | SEQ ID NO: 37 | 3086 | SEQ ID NO: 45 |
| 6 | 3125 | SEQ ID NO: 38 | 1029 | SEQ ID NO: 46 |
| 7 | 1563 | SEQ ID NO: 39 | 343 | SEQ ID NO: 47 |
| 8 | 0 | SEQ ID NO: 40 | 0 | SEQ ID NO: 48 |

| Well | Retinol binding protein (RBP) Conc pg/ml | Reporter Polynucleotide | Serpin B3/SCCA1 (SCC) Conc pg/ml | Reporter Polynucleotide |
|---|---|---|---|---|
| 1 | 500000 | SEQ ID NO: 49 | 500000 | SEQ ID NO: 49 |
| 2 | 250000 | SEQ ID NO: 50 | 250000 | SEQ ID NO: 50 |
| 3 | 125000 | SEQ ID NO: 51 | 125000 | SEQ ID NO: 51 |
| 4 | 62500 | SEQ ID NO: 52 | 62500 | SEQ ID NO: 52 |
| 5 | 31250 | SEQ ID NO: 53 | 31250 | SEQ ID NO: 53 |
| 6 | 15625 | SEQ ID NO: 54 | 15625 | SEQ ID NO: 54 |
| 7 | 7813 | SEQ ID NO: 55 | 7813 | SEQ ID NO: 55 |
| 8 | 0 | SEQ ID NO: 56 | 0 | SEQ ID NO: 56 |

AAT, CEA, RBP and SCC were detected using the following protocol:

1. Prepare reagents as described in detail in individual kit protocols.
2. Prepare standards as described in detail in individual kit protocols. Here, diluted PSA standards in assay diluent A (option of A or B), RBP/AAT standards in diluent N and SCC standards in diluent E2 provided in respective kits.
3. Add standards:
    a. Add 50 µl (AAT/RBP) or 100 µl (CEA/SCC) standard, as specified in appropriate kit protocols, per well of an 8-well ELISA plate, adding one standard dilution per well. Cover wells and incubate for 2.5 hours at room temperature with gentle agitation.
4. Wash:
    a. Discard solution.
    b. Add (300 µl for CEA and SCC, 200 µl for RBP and AAT) 1× appropriate wash solution provided in each ELISA kit. Discard wash solution.
    c. Repeat (b) for total of (4 washes for CEA and SCC, 5 washes for RBP and AAT).
    d. Remove any residual wash solution.
5. Add specified Biotinylated Detection Antibody:
    a. Dilute required detection antibody specific to each protein as described in relevant kit protocols.
    b. Add 50 µl (AAT/RBP) or 100 µl (CEA/SCC) 1× Detection Antibody as specified in appropriate kit protocols, per well, cover wells and incubate for 1 hour at room temperature with gentle agitation.
6. Wash (as step 5).
7. Add Streptavidin:
    a. Dilute Streptavidin (Streptavidin from *Streptomyces avidinii*, Sigma-Aldrich, S4762) to 40 ng/µl with 1× PBS (Phosphate buffered saline 10×, Sigma-Aldrich, P5493).
    b. Add 50 µl 40 ng/µl Streptavidin to each well, cover wells and incubate for 50 minutes at room temperature with gentle agitation.
8. Wash (as step 5)
9. Add barcoded reporters (see polynucleotide sequences for barcode reporter polynucleotide assigned to each well. All oligonucleotides synthesised by IDT.):
    a. Assign one barcoded reporter to each well and. Dilute each to 80 ng in 50 µl 1× TE (TE buffer (20×), ThermoFisher Scientific, T11493).
    b. Add one 50 µl barcoded reporter sample to each appropriate well. Cover wells, incubate at 4° C. overnight, then incubate for 30 minutes at room temperature with gentle agitation.
10. Wash (as step 5).
11. Elute barcoded reporters:
    a. Prepare a solution containing 2 µl USER™ Enzyme (USER™ Enzyme, NEB, M5505) to 50 µl 1× PBS per well.
    b. Add 50 µl USER/PBS solution per well, cover wells and incubate for 90 minutes at 37° C. with agitation.
    c. Pool each set of 8 eluted samples in separate 1.5 ml DNA LoBind tubes (Eppendorf® LoBind microcentrifuge tubes, Sigma-Aldrich, Z666548).
    d. SPRI clean:
        i. Add 400 µl Agencourt AMPure XP DNA SPRI beads (Agencourt AMPure XP, Beckman-Coulter, A63880) to each sample, incubate for 5 minutes with agitation. Pellet beads by placing tube on a magnetic rack.
        ii. Wash twice with 200 µl 70% ethanol.
        iii. Spin down and re-pellet beads, remove residual wash and dry pellet at room temperature for 5-10 minutes.
        iv. Elute each sample in 41 µl nuclease-free water (Nuclease-Free Water, ThermoFisher Scientific, AM9937) for 5 minutes at room temperature. Pellet beads, collect eluted samples.
        v. Pool all four eluted samples to form one barcoded reporter pool.
12. Ligate adapters in preparation for sequencing:
    a. Combine the following in a 1.5 ml DNA LoBind tube (Eppendorf):
        160 µl barcoded reporter pool
        64 µl 1D Barcode Adapter Mix (BAM) (Native Barcoding Kit 1D, Oxford Nanopore Technologies, EXP-NBD103)
        64 µl NEBNext T4 Quick ligation buffer (NEBNext® Quick Ligation Module, NEB, E6056)
        32 µl NEBNext T4 Quick ligase (NEBNext® Quick Ligation Module, NEB, E6056)
    b. Incubate for 10 minutes at room temperature
    c. Clean up with SPRI beads:
        i. Add 128 µl Agencourt AMPure XP DNA SPRI beads, incubate for 5 minutes at room temperature with agitation. Pellet beads by placing tube on a magnetic rack. Remove supernatant.

ii. Add 448 µl Adapter Bead Binding Buffer (ABB) (Ligation Sequencing Kit 1D, Oxford Nanopore Technologies, SQK-LSK108), flick tube to mix. Pellet beads and remove buffer.

iii. Add 25 µl Elution Buffer (ELB) (Ligation Sequencing Kit 1D, Oxford Nanopore Technologies, SQK-LSK108) and mix. Incubate for 10 minutes at room temperature. Pellet beads and collect eluted library.

13. Prepare the adapted library for loading on to Flow Cells:

a. Combine the following, in duplicate:

12 µl eluted adapter-ligated library 25.5 µl library loading beads (LLB) (Library Loading Bead Kit, Oxford Nanopore Technologies, EXP-LLB001)

37.5 µl Running buffer (RBF) (Ligation Sequencing Kit 1D, Oxford Nanopore Technologies, SQK-LSK108)

b. Load one 75 µl sample per SpotON Mk I (R9.4) Flow Cell (Oxford Nanopore Technologies, FLO-MIN106), set up on MinIONs (MinION Mk 1B, Oxford Nanopore Technologies) and primed as described in the protocol 1*D Native barcoding genomic DNA (with EXP-NBD*103 *and SQK-LSK*108) (Oxford Nanopore Technologies).

c. Sequence for 48 hours. Basecall sequencing data via the EPI2ME platform (Metrichor Ltd).

Discussion

Concentration-dependent detection was present for all four proteins, with high similarity in relative abundance of each barcode reporter seen Flow Cell-to-Flow Cell. As seen in Example 2, sequencing data (FIGS. 3A-3D) indicates that higher protein concentration is correlated with higher numbers of reads of the associated barcoded reporter polynucleotide. This demonstrates that this protocol can be used for concentration-dependent detection of a panel of protein biomarkers of clinical interest.

The invention claimed is:

1. A method of determining the presence of a target analyte in a sample, the method comprising:
   (a) immobilizing the target analyte present in the sample on a microparticle;
   (b) contacting the microparticle with: (i) a first detection agent that binds specifically to the target analyte; and (ii) a reporter polynucleotide, wherein the reporter polynucleotide is bound to, or binds to, the first detection agent and wherein the reporter polynucleotide is double-stranded; and
   (c) delivering the microparticle comprising the reporter polynucleotide towards a transmembrane pore, wherein the reporter polynucleotide is immobilized on the microparticle by binding of the first detection agent to the target analyte, and then contacting the transmembrane pore with the immobilized reporter polynucleotide to detect a strand of the immobilized reporter polynucleotide, thereby determining the presence of the target analyte in the sample.

2. The method according to claim 1, wherein the target analyte is immobilized to the microparticle by (i) binding to a capture agent that binds specifically to the target analyte, wherein the capture agent is immobilized on the microparticle, or (ii) binding to an antibody, which antibody is immobilized on the microparticle, wherein the antibody specifically binds to the target analyte.

3. The method according to claim 1, wherein the target analyte is a target antibody and (a) the first detection agent is an antibody which binds to the target antibody and the capture agent is an antigen to which the target antibody binds; or (b) the first detection agent is an antigen to which the target antibody binds and the capture agent is an antibody which binds to the target antibody.

4. The method according to claim 1, wherein the reporter polynucleotide is bound to, or binds to, the first detection agent indirectly.

5. The method according to claim 4, wherein the reporter polynucleotide is bound to, or binds to, the first detection agent indirectly via a second detection agent that binds to the first detection agent.

6. The method according to claim 1 wherein the reporter polynucleotide is bound to, or binds to, the first detection agent indirectly via a second detection agent that binds to the first detection agent, wherein the first detection agent or the second detection agent comprises a first component of an affinity tag and (a) the reporter polynucleotide is attached to a second component of the affinity tag that specifically binds to the first component; or (b) the reporter polynucleotide is attached to first component of an affinity tag, and a second component of the affinity tag that specifically binds to the first component is used to link the first detection agent or the second detection agent to the reporter polynucleotide.

7. The method according to claim 6, wherein the first component of the affinity tag is biotin and the second component of the affinity tag is streptavidin.

8. The method according to claim 6, wherein the reporter polynucleotide is bound to, or binds to, the first detection agent indirectly via the second detection agent that binds to the first detection agent, wherein the first detection agent or the second detection agent comprises the first component of the affinity tag and (a) the reporter polynucleotide is attached to the second component of the affinity tag that specifically binds to the first component.

9. The method according to claim 1, wherein the reporter polynucleotide is from about 10 to 5000 nucleotides in length and comprises DNA, RNA, or a synthetic nucleic acid.

10. The method according to claim 1, comprising determining the presence of two or more target analytes in the sample, wherein each target analyte is detected using a different reporter polynucleotide and the identities of the reporter polynucleotides are determined using the transmembrane pore, wherein the two or more target analytes are immobilized on separate microparticles or on the same microparticle.

11. The method according to claim 10, wherein the two or more target analytes are immobilized on separate microparticles.

12. The method according to claim 10, wherein the two or more target analytes are immobilized on the same microparticle.

13. The method according to claim 1, wherein the first detection agent comprises an antibody.

14. The method according to claim 1, wherein the reporter polynucleotide comprises a nucleic acid sequence selected from the group consisting of SEQ ID NOs: 1-8.

15. The method according to claim 1, wherein the sample is blood.

16. The method according to claim 1, wherein the target analyte is a protein biomarker.

17. The method according to claim 1, wherein the microparticle is a polymer bead.

18. The method according to claim 1 wherein the reporter polynucleotide comprises an adaptor at a free end, which adaptor facilitates interaction of the reporter polynucleotide with the transmembrane pore.

19. The method according to claim 1, wherein two or more reporter polynucleotides are bound to, or bind to, the first detection agent.

20. The method according to claim 19, wherein two or more of the reporter polynucleotides are identical.

* * * * *

SEQUENCE LISTING

```
<160> NUMBER OF SEQ ID NOS: 64

<210> SEQ ID NO 1
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 1
attgcuactt gcctgtcgct ctatcttctg gtgctgaaga aagttgtcgg tgtctttgtg      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataacettt gtcagtaaca tgcacagata cgtacagaaa     240
gacattcagg gaacaacaga accacaattc agaaactccc acagccggac ctccggcact     300
gtaacccttt acctgccggt atccacgttt gtgggtaccg gcttttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cgggagaaac cgtgaacggc ggaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa aacgactgtc     720
accagtggtg gtcttcagag agtgaacccc ggtggaagtg tctcagacac ggttatcagt     780
gccggaggcg gacagagcct tcagggacgg gctgtgaaca ccacgctgaa tggtggcgaa     840
cagtggatgc atgaggggc gatagccaca ggaaccgtca ttaatgataa gggctggcag     900
gtcgtcaagc ccggtacagt ggcaacggat accgttgtta ataccggggc ggaaggggga     960
ccggatgcag aaaacggtga taccgggcag tttgttcgcg gggatgccgt acgcacaacc    1020
atcaataaaa acggtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
```

```
cagattgtca aaaacggggg tgtggccggg aataccaccg ttaatcagaa gggcagactg   1260
caggtggacg ccggtggtac agccacgaat gtcaccctga agcagggcgg cgcactggtt   1320
accagtacgg ctgcaaccgt taccggcata aaccgcctgg gagcattctc tgttgtggag   1380
ggtaaagctg ataatgtcgt actggaaaat ggcggacgcc tggatgtgct gaccggacac   1440
acagccacta ataccgcgt ggatgatggc ggaacgctgg atgtccgcaa cggtggcacc   1500
gccaccaccg tatccatggg aaatggcggt gtactgctgg ccgattccgg tgccgctgtc   1560
agtggtaccc ggagcgacgg aaaggcattc agtatcggag gcggtcaggc ggatgccctg   1620
atgctggaaa aaggcagttc attcacgctg aacgccggtg atacggccac ggataccacg   1680
gtaaatggcg gactgttcac cgccaggggc ggcacactgg cgggcaccac cacgctgaat   1740
aacggcgcca aggttaaac acccaagcag acgccgcaat atcagcacca acagaaaggt   1800
taacacaaag acaccgacaa ctttcttcag caccagaaga tagagcgaca ggcaagtagc   1860
aat                                                                1863
```

<210> SEQ ID NO 2
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 2

```
attgcuactt gcctgtcgct ctatcttctg gtgctgtcga ttccgtttgt agtcgtctgt     60
ttaacctact tgcctgtcgc tctatcttcg gcgtctgctt gggtgtttaa ccgtctctct    120
tgtccgtgca atagctcaat aatagaataa acgatcaat atctatttta tcgatcgttt    180
atatcgatcg ataagctaat aataacccttt gtcagtaaca tgcacagata cgtacagaaa    240
gacattcagg gaacaacaga accacaattc agaaactccc acagccggac ctccggcact    300
gtaacccttt acctgccggt atccacgttt gtgggtaccg gcttttttat tcaccctcaa    360
tctaaggaaa agctgatgaa acgacatctg aatacctgct acaggctggt atggaatcac    420
atgacgggcg ctttcgtggt tgcctccgaa ctggcccgcg cacggggtaa acgtggcggt    480
gtggcggttg cactgtctct tgccgcagtc acgtcactcc cggtgctggc tgctgacatc    540
gttgtgcacc cggagaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa acgactgtc    720 accagtggtg gtcttcagag agtgaacccc ggtggaagtg tctcagacac ggttatcagt    780 gccgaggcg gacagagcct tcagggacgg gctgtgaaca ccacgctgaa tggtggcgaa    840
cagtggatgc atgagggggc gatagccaca ggaaccgtca ttaatgataa gggctggcag    900
gtcgtcaagc ccggtacagt ggcaacggat accgttgtta ataccggggc ggaaggggga    960
ccggatgcag aaaacggtga taccgggcag tttgttcgcg ggatgccgt acgcacaacc    1020 atcaataaa acgtcgcca gattgtgaga gctgaaggaa cggcaaatac cactgtggtt    1080
tatgccggcg cgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg   1260
```

```
caggtggacg ccggtggtac agccacgaat gtcaccctga agcagggcgg cgcactggtt      1320
accagtacgg ctgcaaccgt taccggcata aaccgcctgg gagcattctc tgttgtggag      1380
ggtaaagctg ataatgtcgt actggaaaat ggcggacgcc tggatgtgct gaccggacac      1440
acagccacta atacccgcgt ggatgatggc ggaacgctgg atgtccgcaa cggtggcacc      1500
gccaccaccg tatccatggg aaatggcggt gtactgctgg ccgattccgg tgccgctgtc      1560
agtggtaccc ggagcgacgg aaaggcattc agtatcggag cggtcaggc ggatgccctg       1620 atgctggaaa aaggcagttc attcacgctg aacgccggtg atacggccac ggataccacg      1680
gtaaatggcg gactgttcac cgccaggggc ggcacactgg cgggcaccac cacgctgaat      1740
aacggcgcca aaggttaaac acccaagcag acgccgcaat atcagcacca acagaaaggt      1800
taaacagacg actacaaacg gaatcgacag caccagaaga tagagcgaca ggcaagtagc      1860
aat                                                                   1863

<210> SEQ ID NO 3
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 3
attgcuactt gcctgtcgct ctatcttctg gtgctggagt cttgtgtccc agttaccagg       60
ttaacctact tgcctgtcgc tctatcttcg gcgtctgctt gggtgtttaa ccgtctctct      120
tgtccgtgca atagctcaat aatagaataa acgatcaat atctatttta tcgatcgttt       180
atatcgatcg ataagctaat aataacettt gtcagtaaca tgcacagata cgtacagaaa      240
gacattcagg gaacaacaga accacaattc agaaactccc acagccggac ctccggcact      300 gtaaccctt acctgccggt atccacgttt gtgggtaccg gcttttttat tcaccctcaa       360
tctaaggaaa agctgatgaa acgacatctg aatacctgct acaggctggt atggaatcac      420
atgacgggcg ctttcgtggt tgcctccgaa ctggcccgcg cacggggtaa acgtggcggt      480
gtggcggttg cactgtctct tgccgcagtc acgtcactcc cggtgctggc tgctgacatc      540
gttgtgcacc cggagaaaac cgtgaacggc ggaacactgg caaatcatga caaccagatt      600
gtcttcggta cgaccaacgg aatgaccatc agtaccgggc tggagtatgg gccggataac      660
gaggccaata ccggcgggca atgggtacag gatggcggaa cagccaacaa aacgactgtc      720
accagtggtg gtcttcagag agtgaacccc ggtggaagtg tctcagacac ggttatcagt      780
gccggaggcg gacagagcct tcagggacgg gctgtgaaca ccacgctgaa tggtggcgaa      840
cagtggatgc atgaggggc gatagccaca ggaaccgtca ttaatgataa gggctggcag      900
gtcgtcaagc ccggtacagt ggcaacggat accgttgtta taccgggggc ggaaggggga    960
ccggatgcag aaaacggtga taccgggcag tttgttcgcg gggatgccgt acgcacaacc      1020
atcaataaaa acggtcgcca gattgtgaga gctgaaggac cggcaaatac cactgtggtt      1080
tatgccggcg gcgaccagac tgtacatggt cacgcactgg ataccacgct gaatggggga    1140
taccagtatg tgcacaacgg cggtacagcg tctgacactg ttgtgaacag tgacggctgg      1200
cagattgtca aaaacggggg tgtggccggg aataccaccg ttaatcagaa gggcagactg      1260
```

-continued

| | |
|---|---|
| caggtggacg ccggtggtac agccacgaat gtcaccctga agcagggcgg cgcactggtt | 1320 |
| accagtacgg ctgcaaccgt taccggcata aaccgcctgg gagcattctc tgttgtggag | 1380 |
| ggtaaagctg ataatgtcgt actggaaaat ggcggacgcc tggatgtgct gaccggacac | 1440 |
| acagccacta atacccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag gcggtcaggc ggatgccctg | 1620 |
| atgctggaaa aaggcagttc attcacgctg aacgccggtg atacggccac ggataccacg | 1680 |
| gtaaatggcg gactgttcac cgccaggggc ggcacactgg cgggcaccac cacgctgaat | 1740 |
| aacggcgcca aaggttaaac acccaagcag acgccgcaat atcagcacca acagaaaggt | 1800 |
| taacctggta actgggacac aagactccag caccagaaga tagagcgaca ggcaagtagc | 1860 |
| aat | 1863 |

<210> SEQ ID NO 4
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 4

| | |
|---|---|
| attgcuactt gcctgtcgct ctatcttctg gtgctgcttg tccagggttt gtgtaacctt | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataaccttt gtcagtaaca tgcacagata cgtacagaaa | 240 |
| gacattcagg gaacaacaga accacaattc agaaactccc acagccggac ctccggcact | 300 |
| gtaaccctttt acctgccggt atccacgttt gtgggtaccg gcttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cgggagaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccggaggcg gacagagcct tcagggacgg gctgtgaaca ccacgctgaa tggtggcgaa | 840 |
| cagtggatgc atgagggggc gatagccaca ggaaccgtca ttaatgataa gggctggcag | 900 |
| gtcgtcaagc ccggtacagt ggcaacggat accgttgtta ataccggggc ggaagggga | 960 |
| ccggatgcag aaaacggtga taccgggcag tttgttcgcg gggatgccgt acgcacaacc | 1020 |
| atcaataaaa acggtcgcca gattgtgaga gctgaaggaa cggcaaatac cactgtggtt | 1080 |
| tatgccggcg gcgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcaccctga agcagggcgg cgcactggtt | 1320 |

```
accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta atacccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccaggggc ggcacactgg cgggcaccac cacgctgaat    1740
aacggcgcca aggttaaaac acccaagcag acgccgcaat atcagcacca acagaaaggt    1800
taaaaggtta cacaaaccct ggacaagcag caccagaaga tagagcgaca ggcaagtagc    1860
aat                                                                  1863

<210> SEQ ID NO 5
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 5
attgcuactt gcctgtcgct ctatcttctg gtgctgttct cgcaaaggca gaaagtagtc      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataacctt gtcagtaaca tgcacagata cgtacagaaa      240
gacattcagg gaacaacaga accacaattc agaaactccc acagccggac ctccggcact     300
gtaacccttt acctgccggt atccacgttt gtgggtaccg gcttttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cgggagaaac cgtgaacggc ggaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa aacgactgtc     720
accagtggtg gtcttcagag agtgaacccc ggtggaagtg tctcagacac ggttatcagt     780 gccgaggcg acagagcct tcagggacgg gctgtgaaca ccacgctgaa tggtggcgaa        840
cagtggatgc atgagggggc gatagccaca ggaaccgtca ttaatgataa gggctggcag     900
gtcgtcaagc ccggtacagt ggcaacggat accgttgtta taccggggc ggaagggga       960 ccggatgcag aaaacggtga taccgggcag tttgttcgcg gggatgccgt acgcacaacc    1020
atcaataaaa acggtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga agcagggcgg cgcactggtt    1320
```

| | |
|---|---|
| accagtacgg ctgcaaccgt taccggcata aaccgcctgg gagcattctc tgttgtggag | 1380 |
| ggtaaagctg ataatgtcgt actggaaaat ggcggacgcc tggatgtgct gaccggacac | 1440 |
| acagccacta atacccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag gcggtcaggc ggatgccctg | 1620 |
| atgctggaaa aaggcagttc attcacgctg aacgccggtg atacggccac ggataccacg | 1680 |
| gtaaatggcg gactgttcac cgccaggggc ggcacactgg cgggcaccac cacgctgaat | 1740 |
| aacggcgcca aaggttaaac acccaagcag acgccgcaat atcagcacca acagaaaggt | 1800 |
| taagactact ttctgccttt gcgagaacag caccagaaga tagagcgaca ggcaagtagc | 1860 |
| aat | 1863 |

<210> SEQ ID NO 6
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 6

| | |
|---|---|
| attgcuactt gcctgtcgct ctatcttctg gtgctgttca gggaacaaac caagttacgt | 60 |
| ttaacctact tgcctgtcgc tctatcttcg gcgtctgctt gggtgtttaa ccgtctctct | 120 |
| tgtccgtgca atagctcaat aatagaataa acgatcaat atctatttta tcgatcgttt | 180 |
| atatcgatcg ataagctaat aataaccttt gtcagtaaca tgcacagata cgtacagaaa | 240 |
| gacattcagg gaacaacaga accacaattc agaaactccc acagccggac ctccggcact | 300 |
| gtaacccttt acctgccggt atccacgttt gtgggtaccg gcttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cggagaaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa acgactgtc | 720 |
| accagtggtg gtcttcagag agtgaacccc ggtggaagtg tctcagacac ggttatcagt | 780 |
| gccgaggcg acagagcct tcagggacgg gctgtgaaca ccacgctgaa tggtggcgaa | 840 |
| cagtggatgc atgagggggc gatagccaca ggaaccgtca ttaatgataa gggctggcag | 900 |
| gtcgtcaagc ccggtacagt ggcaacggat accgttgtta taccggggc ggaagggggga | 960 |
| ccggatgcag aaaacggtga taccgggcag tttgttcgcg gggatgccgt acgcacaacc | 1020 |
| atcaataaaa acggtcgcca gattgtgaga gctgaaggaa cggcaaatac cactgtggtt | 1080 |
| tatgccggcg cgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcaccctga gcagggcgg cgcactggtt | 1320 |
| accagtacgg ctgcaaccgt taccggcata aaccgcctgg gagcattctc tgttgtggag | 1380 |

-continued

| | |
|---|---|
| ggtaaagctg ataatgtcgt actggaaaat ggcggacgcc tggatgtgct gaccggacac | 1440 |
| acagccacta atacccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag gcggtcaggc ggatgccctg | 1620 |
| atgctggaaa aaggcagttc attcacgctg aacgccggtg atacggccac ggataccacg | 1680 |
| gtaaatggcg gactgttcac cgccaggggc ggcacactgg cgggcaccac cacgctgaat | 1740 |
| aacggcgcca aggttaaac acccaagcag acgccgcaat atcagcacca acagaaaggt | 1800 |
| taaacgtaac ttggtttgtt ccctgaacag caccagaaga tagagcgaca ggcaagtagc | 1860 |
| aat | 1863 |

<210> SEQ ID NO 7
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 7

| | |
|---|---|
| attgcuactt gcctgtcgct ctatcttctg gtgctggttc ctcgtgcagt gtcaagagat | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataacctt gtcagtaaca tgcacagata cgtacagaaa | 240 |
| gacattcagg gaacaacaga accacaattc agaaactccc acagccggac ctccggcact | 300 |
| gtaaccctt acctgccggt atccacgttt gtgggtaccg gcttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cggagaaaac cgtgaacggc ggaacactgg caaatcatga caaccagatt | 600 |
| gtcttcggta cgaccaacgg aatgaccatc agtaccgggc tggagtatgg ccggataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccggaggcg gacagagcct tcagggacgg gctgtgaaca ccacgctgaa tggtggcgaa | 840 |
| cagtggatgc atgagggggc gatagccaca ggaaccgtca ttaatgataa gggctggcag | 900 |
| gtcgtcaagc ccggtacagt ggcaacggat accgttgtta taccgggggc ggaaggggga | 960 |
| ccggatgcag aaaacggtga taccgggcag tttgttcgcg gggatgccgt acgcacaacc | 1020 |
| atcaataaaa acgtcgcca gattgtgaga gctgaaggaa cggcaaatac cactgtggtt | 1080 |
| tatgccggcg cgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcaccctga gcagggcgg cgcactggtt | 1320 |
| accagtacgg ctgcaaccgt taccggcata aaccgcctgg gagcattctc tgttgtggag | 1380 |

| | |
|---|---|
| ggtaaagctg ataatgtcgt actggaaaat ggcggacgcc tggatgtgct gaccggacac | 1440 |
| acagccacta atacccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag cggtcaggc ggatgccctg | 1620 |
| atgctggaaa aaggcagttc attcacgctg aacgccggtg atacggccac ggataccacg | 1680 |
| gtaaatggcg gactgttcac cgccaggggc ggcacactgg cgggcaccac cacgctgaat | 1740 |
| aacggcgcca aggttaaac acccaagcag acgccgcaat atcagcacca acagaaaggt | 1800 |
| taaatctctt gacactgcac gaggaaccag caccagaaga tagagcgaca ggcaagtagc | 1860 |
| aat | 1863 |

<210> SEQ ID NO 8
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 8

| | |
|---|---|
| attgcuactt gcctgtcgct ctatcttctg gtgctgttgc gtcctgttac gagaactcat | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataacccttt gtcagtaaca tgcacagata cgtacagaaa | 240 |
| gacattcagg gaacaacaga accacaattc agaaactccc acagccggac ctccggcact | 300 |
| gtaacccttt acctgccggt atccacgttt gtgggtaccg gcttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cgggagaaac cgtgaacggc ggaacactgg caaatcatga caaccagatt | 600 |
| gtcttcggta cgaccaacgg aatgaccatc agtaccgggc tggagtatgg gccgataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccggaggcg gacagagcct tcagggacgg gctgtgaaca ccacgctgaa tggtggcgaa | 840 |
| cagtggatgc atgaggggc gatagccaca ggaaccgtca ttaatgataa gggctggcag | 900 |
| gtcgtcaagc ccggtacagt ggcaacggat accgttgtta ataccggggc ggaaggggga | 960 |
| ccggatgcag aaaacggtga taccgggcag tttgttcgcg gggatgccgt acgcacaacc | 1020 |
| atcaataaaa acgtcgcca gattgtgaga gctgaaggaa cggcaaatac cactgtggtt | 1080 |
| tatgccggcg gcgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcaccctga gcagggcgg cgcactggtt | 1320 |
| accagtacgc ctgcaaccgt taccggcata aaccgcctgg gagcattctc tgttgtggag | 1380 |
| ggtaaagctg ataatgtcgt actggaaaat ggcggacgcc tggatgtgct gaccggacac | 1440 |

```
acagccacta ataccogcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccaggggc ggcacactgg cgggcaccac cacgctgaat    1740
aacggcgcca aggttaaac acccaagcag acgccgcaat atcagcacca acagaaaggt    1800
taaatgagtt ctcgtaacag gacgcaacag caccagaaga tagagcgaca ggcaagtagc    1860
aat                                                                  1863
```

<210> SEQ ID NO 9
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 9

```
attgcuactt gcctgtcgct ctatcttctg gtgctgaaga aagttgtcgg tgtctttgtg     60
ttaacctact tgcctgtcgc tctatcttcg gcgtctgctt gggtgtttaa ccgtctctct    120
tgtccgtgca atagctcaat aatagaataa aacgatcaat atctatttta tcgatcgttt    180
atatcgatcg ataagctaat aataacccttt gtcagtaaca tgcacagata cgtacagaaa    240
gacattcagg gaacaacaga accacaattc agaaactccc acagccggac ctccggcact    300
gtaacccttt acctgccggt atccacgttt gtgggtaccg gctttttat tcaccctcaa    360 tctaaggaaa agctgatgaa acgacatctg aatacctgct acaggctggt atggaatcac    420
atgacgggcg ctttcgtggt tgcctccgaa ctggcccgcg cacggggtaa acgtggcggt    480
gtggcggttg cactgtctct tgccgcagtc acgtcactcc cggtgctggc tgctgacatc    540
gttgtgcacc cgggagaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa acgactgtc    720 accagtggtg gtcttcagag agtgaacccc ggtggaagtg tctcagacac ggttatcagt    780 gccgaggcg gacagagcct tcagggacgg gctgtgaaca ccacgctgaa tggtggcgaa    840
cagtggatgc atgaggggc gatagccaca ggaaccgtca ttaatgataa gggctggcag    900
gtcgtcaagc ccggtacagt ggcaacggat accgttgtta taccggggc ggaaggggga    960 ccggatgcag aaaacggtga taccgggcag tttgttcgcg gggatgccgt acgcacaacc    1020
atcaataaaa acggtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga agcagggcgg cgcactggtt    1320
accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
```

| | |
|---|---|
| acagccacta ataccogcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag gcggtcaggc ggatgccctg | 1620 |
| atgctggaaa aaggcagttc attcacgctg aacgccggtg atacggccac ggataccacg | 1680 |
| gtaaatggcg gactgttcac cgccaggggc ggcacactgg cgggcaccac cacgctgaat | 1740 |
| aacggcgcca aaggttaaac acccaagcag acgccgcaat atcagcacca acagaaaggt | 1800 |
| taacacaaag acaccgacaa ctttcttcag caccagaaga tagagcgaca ggcaagtagc | 1860 |
| aat | 1863 |

<210> SEQ ID NO 10
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 10

| | |
|---|---|
| attgcuactt gcctgtcgct ctatcttctg gtgctgtcga ttccgtttgt agtcgtctgt | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataacccttt gtcagtaaca tgcacagata cgtacagaaa | 240 |
| gacattcagg gaacaacaga accacaattc agaaactccc acagccggac ctccggcact | 300 |
| gtaacccttt acctgccggt atccacgttt gtgggtaccg gctttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cgggagaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccgaggcg gacagagcct tcagggacgg gctgtgaaca ccacgctgaa tggtggcgaa | 840 |
| cagtggatgc atgaggggc gatagccaca ggaaccgtca ttaatgataa gggctggcag | 900 |
| gtcgtcaagc ccggtacagt ggcaacggat accgttgtta ataccggggc ggaaggggga | 960 |
| ccggatgcag aaaacggtga taccgggcag tttgttcgcg gggatgccgt acgcacaacc | 1020 |
| atcaataaaa acggtcgcca gattgtgaga gctgaaggaa cggcaaatac cactgtggtt | 1080 |
| tatgccggcg gcgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcaccctga gcagggcgg cgcactggtt | 1320 |
| accagtacgg ctgcaaccgt taccggcata aaccgcctgg gagcattctc tgttgtggag | 1380 |
| ggtaaagctg ataatgtcgt actggaaaat ggcggacgcc tggatgtgct gaccggacac | 1440 |
| acagccacta ataccogcgt ggatgatggc ggaacgctgg atgtccgcaa cggtggcacc | 1500 |

```
gccaccaccg tatccatggg aaatggcggt gtactgctgg ccgattccgg tgccgctgtc    1560
agtggtaccc ggagcgacgg aaaggcattc agtatcggag cggtcaggc ggatgccctg     1620 atgctggaaa aaggcagttc attcacgctg aacgccggtg atacggccac ggataccacg    1680
gtaaatggcg gactgttcac cgccaggggc ggcacactgg cgggcaccac cacgctgaat    1740
aacggcgcca aggttaaac acccaagcag acgccgcaat atcagcacca acagaaaggt     1800
taaacagacg actacaaacg gaatcgacag caccagaaga tagagcgaca ggcaagtagc    1860
aat                                                                  1863
```

<210> SEQ ID NO 11
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 11

```
attgcuacttg cctgtcgct ctatcttctg gtgctggagt cttgtgtccc agttaccagg     60
ttaacctact tgcctgtcgc tctatcttcg gcgtctgctt gggtgtttaa ccgtctctct    120
tgtccgtgca atagctcaat aatagaataa aacgatcaat atctatttta tcgatcgttt    180
atatcgatcg ataagctaat aataacctttt gtcagtaaca tgcacagata cgtacagaaa    240
gacattcagg gaacaacaga accacaattc agaaactccc acagccggac ctccggcact    300
gtaaaccttt acctgccggt atccacgttt gtgggtaccg gctttttat tcaccctcaa     360 tctaaggaaa agctgatgaa acgacatctg aatacctgct acaggctggt atggaatcac    420
atgacgggcg ctttcgtggt tgcctccgaa ctggcccgcg cacggggtaa acgtggcggt    480
gtggcggttg cactgtctct tgccgcagtc acgtcactcc cggtgctggc tgctgacatc    540
gttgtgcacc cggagaaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa aacgactgtc    720
accagtggtg gtcttcagag agtgaacccc ggtggaagtg tctcagacac ggttatcagt    780
gccggaggcg acagagcct tcagggacgg gctgtgaaca ccacgctgaa tggtggcgaa    840
cagtggatgc atgagggggc gatagccaca ggaaccgtca ttaatgataa gggctggcag    900
gtcgtcaagc ccggtacagt ggcaacggat accgttgtta ataccggggc ggaaggggga    960
ccggatgcag aaaacggtga taccgggcag tttgttcgcg ggatgccgt acgcacaacc   1020 atcaataaaa acggtcgcca gattgtgaga gctgaaggaa cggcaaatac cactgtggtt    1080
tatgccggcg cgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcacccctga agcagggcgg cgcactggtt    1320
accagtacgg ctgcaacccgt taccggcata aaccgcctgg gagcattctc tgttgtggag    1380
ggtaaagctg ataatgtcgt actggaaaat ggcggacgcc tggatgtgct gaccggacac    1440
acagccacta ataccccgcgt ggatgatggc ggaacgctgg atgtccgcaa cggtggcacc    1500
```

```
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccagggcc ggcacactgg cgggcaccac cacgctgaat    1740
aacggcgcca aaggttaaac acccaagcag acgccgcaat atcagcacca acagaaaggt    1800
taacctggta actgggacac aagactccag caccagaaga tagagcgaca ggcaagtagc    1860
aat                                                                  1863

<210> SEQ ID NO 12
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 12
attgcuactt gcctgtcgct ctatcttctg gtgctgttcg gattctatcg tgtttcccta     60
ttaacctact tgcctgtcgc tctatcttcg gcgtctgctt gggtgtttaa ccgtctctct    120
tgtccgtgca atagctcaat aatagaataa aacgatcaat atctatttta tcgatcgttt    180
atatcgatcg ataagctaat aataaccttt gtcagtaaca tgcacagata cgtacagaaa    240
gacattcagg gaacaacaga accacaattc agaaactccc acagccggac ctccggcact    300
gtaacccttt acctgccggt atccacgttt gtgggtaccg gctttttat tcaccctcaa    360 tctaaggaaa agctgatgaa acgacatctg aatacctgct acaggctggt atggaatcac    420
atgacgggcg ctttcgtggt tgcctccgaa ctggcccgcg cacggggtaa acgtggcggt    480
gtggcggttg cactgtctct tgccgcagtc acgtcactcc cggtgctggc tgctgacatc    540
gttgtgcacc cggagaaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa aacgactgtc    720
accagtggtg gtcttcagag agtgaacccc ggtggaagtg tctcagacac ggttatcagt    780
gccggaggcg gacagagcct tcagggacgg gctgtgaaca ccacgctgaa tggtggcgaa    840
cagtggatgc atgagggggc gatagccaca ggaaccgtca ttaatgataa gggctggcag    900
gtcgtcaagc ccggtacagt ggcaacggat accgttgtta ataccggggc ggaagggga     960 ccggatgcag aaaacggtga taccgggcag tttgttcgcg gggatgccgt acgcacaacc   1020
atcaataaaa acggtcgcca gattgtgaga gctgaaggaa cggcaaatac cactgtggtt   1080
tatgccggcg cgaccagac tgtacatggt cacgcactgg ataccacgct gaatggggga   1140
taccagtatg tgcacaacgg cggtacagcg tctgacactg ttgtgaacag tgacggctgg   1200
cagattgtca aaaacggggg tgtggccggg aataccaccg ttaatcagaa gggcagactg   1260
caggtggacg ccggtggtac agccacgaat gtcaccctga gcagggcgg cgcactggtt   1320 accagtacgg ctgcaaccgt taccggcata aaccgcctgg gagcattctc tgttgtggag   1380
ggtaaagctg ataatgtcgt actggaaaat ggcggacgcc tggatgtgct gaccggacac   1440
acagccacta atacccgcgt ggatgatggc ggaacgctga atgtccgcaa cggtggcacc   1500
gccaccaccg tatccatggg aaatggcggt gtactgctgg ccgattccgg tgccgctgtc   1560
```

-continued

| | |
|---|---|
| agtggtaccc ggagcgacgg aaaggcattc agtatcggag gcggtcaggc ggatgccctg | 1620 |
| atgctggaaa aaggcagttc attcacgctg aacgccggtg atacggccac ggataccacg | 1680 |
| gtaaatggcg gactgttcac cgccaggggc ggcacactgg cgggcaccac cacgctgaat | 1740 |
| aacggcgcca aaggttaaac acccaagcag acgccgcaat atcagcacca acagaaaggt | 1800 |
| taatagggaa acacgataga atccgaacag caccagaaga tagagcgaca ggcaagtagc | 1860 |
| aat | 1863 |

<210> SEQ ID NO 13
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 13

| | |
|---|---|
| attgcuactt gcctgtcgct ctatcttctg gtgctgcttg tccagggttt gtgtaacctt | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataaccttt gtcagtaaca tgcacagata cgtacagaaa | 240 |
| gacattcagg gaacaacaga accacaattc agaaactccc acagccggac ctccggcact | 300 |
| gtaaccctt acctgccggt atccacgttt gtgggtaccg gcttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cgggagaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccgaggcg acagagcct tcaggacgg gctgtgaaca ccacgctgaa tggtggcgaa | 840 |
| cagtggatgc atgagggggc gatagccaca ggaaccgtca ttaatgataa gggctggcag | 900 |
| gtcgtcaagc ccggtacagt ggcaacggat accgttgtta ataccggggc ggaagggga | 960 |
| ccggatgcag aaaacggtga taccgggcag tttgttcgcg gggatgccgt acgcacaacc | 1020 |
| atcaataaaa acggtcgcca gattgtgaga gctgaaggaa cggcaaatac cactgtggtt | 1080 |
| tatgccggcg gcgaccagac tgtacatggt cacgcactgg ataccacgct gaatggggga | 1140 |
| taccagtatg tgcacaacgg cggtacagcc tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcacccctga agcagggcgg cgcactggtt | 1320 |
| accagtacgg ctgcaaccgt taccggcata aaccgcctgg gagcattctc tgttgtggag | 1380 |
| ggtaaagctg ataatgtcgt actggaaaat ggcggacgcc tggatgtgct gaccggacac | 1440 |
| acagccacta ataccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |

| | |
|---|---|
| agtggtaccc ggagcgacgg aaaggcattc agtatcggag gcggtcaggc ggatgccctg | 1620 |
| atgctggaaa aaggcagttc attcacgctg aacgccggtg atacggccac ggataccacg | 1680 |
| gtaaatggcg gactgttcac cgccagggc ggcacactgg cgggcaccac cacgctgaat | 1740 |
| aacggcgcca aggttaaac acccaagcag acgccgcaat atcagcacca acagaaaggt | 1800 |
| taaaaggtta cacaaaccct ggacaagcag caccagaaga tagagcgaca ggcaagtagc | 1860 |
| aat | 1863 |

<210> SEQ ID NO 14
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 14

| | |
|---|---|
| attgcuacttt gcctgtcgct ctatcttctg gtgctgttct cgcaaaggca gaaagtagtc | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataacccttt gtcagtaaca tgcacagata cgtacagaaa | 240 |
| gacattcagg gaacaacaga accacaattc agaaactccc acagccggac ctccggcact | 300 |
| gtaaccccttt acctgccggt atccacgttt gtgggtaccg gcttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cgggagaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccgagggcg gacagagcct tcagggacgg gctgtgaaca ccacgctgaa tggtggcgaa | 840 |
| cagtggatgc atgagggggc gatagccaca ggaaccgtca ttaatgataa gggctggcag | 900 |
| gtcgtcaagc ccggtacagt ggcaacggat accgttgtta ataccggggc ggaaggggga | 960 |
| ccggatgcag aaaacggtga taccgggcag tttgttcgcg gggatgccgt acgcacaacc | 1020 |
| atcaataaaa acggtcgcca gattgtgaga gctgaaggaa cggcaaatac cactgtggtt | 1080 |
| tatgccggcg gcgaccagac tgtacatggt cacgcactgg ataccacgct gaatggggga | 1140 |
| taccagtatg tgcacaacgg cggtacagcc tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcacccctga agcagggcgg cgcactggtt | 1320 |
| accagtacgg ctgcaaccgt taccggcata accgcctggg gagcattctc tgttgtggag | 1380 |
| ggtaaagctg ataatgtcgt actggaaaat ggcggacgcc tggatgtgct gaccggacac | 1440 |
| acagccacta atacccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag gcggtcaggc ggatgccctg | 1620 |

| | |
|---|---|
| atgctggaaa aaggcagttc attcacgctg aacgccggtg atacggccac ggataccacg | 1680 |
| gtaaatggcg gactgttcac cgccagggc ggcacactgg cgggcaccac cacgctgaat | 1740 |
| aacggcgcca aggttaaac acccaagcag acgccgcaat atcagcacca acagaaaggt | 1800 |
| taagactact ttctgccttt gcgagaacag caccagaaga tagagcgaca ggcaagtagc | 1860 |
| aat | 1863 |

<210> SEQ ID NO 15
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 15

| | |
|---|---|
| attgcuactt gcctgtcgct ctatcttctg gtgctgttca gggaacaaac caagttacgt | 60 |
| ttaacctact tgcctgtcgc tctatcttcg gcgtctgctt gggtgtttaa ccgtctctct | 120 |
| tgtccgtgca atagctcaat aatagaataa acgatcaat atctatttta tcgatcgttt | 180 |
| atatcgatcg ataagctaat aataaccttt gtcagtaaca tgcacagata cgtacagaaa | 240 |
| gacattcagg gaacaacaga accacaattc agaaactccc acagccggac ctccggcact | 300 |
| gtaaccctt acctgccggt atccacgttt gtgggtaccg gctttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cggagaaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa acgactgtc | 720 |
| accagtggtg gtcttcagag agtgaacccc ggtggaagtg tctcagacac ggttatcagt | 780 |
| gccggaggcg gacagagcct tcagggacgg gctgtgaaca ccacgctgaa tggtggcgaa | 840 |
| cagtggatgc atgaggggc gatagccaca ggaaccgtca ttaatgataa gggctggcag | 900 |
| gtcgtcaagc ccggtacagt ggcaacggat accgttgtta ataccggggc ggaagggga | 960 |
| ccggatgcag aaaacggtga taccgggcag tttgttcgcg gggatgccgt acgcacaacc | 1020 |
| atcaataaa acggtcgcca gattgtgaga gctgaaggaa cggcaaatac cactgtggtt | 1080 |
| tatgccggcg cgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaacggggg tgtggccggg aataccaccg ttaatcagaa gggcagactg | 1260 |
| caggtggacg ccggtggtac agccacgaat gtcaccctga gcagggcgg cgcactggtt | 1320 |
| accagtacgg ctgcaaccgt taccggcata aaccgcctgg gagcattctc tgttgtggag | 1380 |
| ggtaaagctg ataatgtcgt actggaaaat ggcggacgcc tggatgtgct gaccggacac | 1440 |
| acagccacta ataccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag gcggtcaggc ggatgccctg | 1620 |

| | |
|---|---|
| atgctggaaa aaggcagttc attcacgctg aacgccggtg atacggccac ggataccacg | 1680 |
| gtaaatggcg gactgttcac cgccaggggc ggcacactgg cgggcaccac cacgctgaat | 1740 |
| aacggcgcca aaggttaaac acccaagcag acgccgcaat atcagcacca acagaaaggt | 1800 |
| taaacgtaac ttggtttgtt ccctgaacag caccagaaga tagagcgaca ggcaagtagc | 1860 |
| aat | 1863 |

<210> SEQ ID NO 16
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 16

| | |
|---|---|
| attgcuactt gcctgtcgct ctatcttctg gtgctgaagc gttgaaacct ttgtcctctc | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataaccttt gtcagtaaca tgcacagata cgtacagaaa | 240 |
| gacattcagg gaacaacaga accacaattc agaaactccc acagccggac ctccggcact | 300 |
| gtaacccttt acctgccggt atccacgttt gtgggtaccg cttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cggagaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccggaggcg gacagagcct tcagggacgg gctgtgaaca ccacgctgaa tggtggcgaa | 840 |
| cagtggatgc atgaggggc gatagccaca ggaaccgtca ttaatgataa gggctggcag | 900 |
| gtcgtcaagc ccggtacagt ggcaacggat accgttgtta ataccggggc ggaaggggga | 960 |
| ccggatgcag aaaacggtga taccgggcag tttgttcgcg gggatgccgt acgcacaacc | 1020 |
| atcaataaaa acgtcgcca gattgtgaga gctgaaggaa cggcaaatac cactgtggtt | 1080 |
| tatgccggcg cgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcacccctga agcagggcgg cgcactggtt | 1320 |
| accagtacgg ctgcaaccgt taccggcata aaccgcctgg gagcattctc tgttgtggag | 1380 |
| ggtaaagctg ataatgtcgt actgaaaat ggcggacgcc tggatgtgct gaccggacac | 1440 |
| acagccacta ataccgcgt ggatgatggc ggaacgctgg atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag cggtcaggc ggatgccctg | 1620 |
| atgctggaaa aaggcagttc attcacgctg aacgccggtg atacggccac ggataccacg | 1680 |

| | |
|---|---|
| gtaaatggcg gactgttcac cgccagggc ggcacactgg cgggcaccac cacgctgaat | 1740 |
| aacggcgcca aaggttaaac acccaagcag acgccgcaat atcagcacca acagaaaggt | 1800 |
| taagagagga caaaggtttc aacgcttcag caccagaaga tagagcgaca ggcaagtagc | 1860 |
| aat | 1863 |

<210> SEQ ID NO 17
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 17

| | |
|---|---|
| attgcuactt gcctgtcgct ctatcttctg gtgctgaagc gttgaaacct ttgtcctctc | 60 |
| ttaacctact tgcctgtcgc tctatcttcg gcgtctgctt gggtgtttaa ccgtctctct | 120 |
| tgtccgtgca atagctcaat aatagaataa aacgatcaat atctatttta tcgatcgttt | 180 |
| atatcgatcg ataagctaat aataacccttt gtcagtaaca tgcacagata cgtacagaaa | 240 |
| gacattcagg gaacaacaga accacaattc agaaactccc acagccggac ctccggcact | 300 |
| gtaacccttt acctgccggt atccacgttt gtgggtaccg gcttttttat tcaccctcaa | 360 |
| tctaaggaaa agctgatgaa acgacatctg aatacctgct acaggctggt atggaatcac | 420 |
| atgacgggcg ctttcgtggt tgcctccgaa ctggcccgcg cacggggtaa acgtggcggt | 480 |
| gtggcggttg cactgtctct tgccgcagtc acgtcactcc cggtgctggc tgctgacatc | 540 |
| gttgtgcacc cgggagaaac cgtgaacggc ggaacactgg caaatcatga caaccagatt | 600 |
| gtcttcggta cgaccaacgg aatgaccatc agtaccgggc tggagtatgg gccggataac | 660 |
| gaggccaata ccggcgggca atgggtacag gatggcggaa cagccaacaa aacgactgtc | 720 |
| accagtggtg gtcttcagag agtgaacccc ggtggaagtg tctcagacac ggttatcagt | 780 |
| gccggaggcg gacagagcct tcagggacgg gctgtgaaca ccacgctgaa tggtggcgaa | 840 |
| cagtggatgc atgagggggc gatagccaca ggaaccgtca ttaatgataa gggctggcag | 900 |
| gtcgtcaagc ccggtacagt ggcaacggat accgttgtta taccggggc ggaagggga | 960 |
| ccggatgcag aaaacggtga taccgggcag tttgttcgcg gggatgccgt acgcacaacc | 1020 |
| atcaataaaa acggtcgcca gattgtgaga gctgaaggaa cggcaaatac cactgtggtt | 1080 |
| tatgccggcg gcgaccagac tgtacatggt cacgcactgg ataccacgct gaatggggga | 1140 |
| taccagtatg tgcacaacgg cggtacagcg tctgacactg ttgtgaacag tgacggctgg | 1200 |
| cagattgtca aaaacggggg tgtggccggg aataccaccg ttaatcagaa gggcagactg | 1260 |
| caggtggacg ccggtggtac agccacgaat gtcaccctga gcagggcgg cgcactggtt | 1320 |
| accagtacgg ctgcaaccgt taccggcata aaccgcctgg gagcattctc tgttgtggag | 1380 |
| ggtaaagctg ataatgtcgt actggaaaat ggcggacgcc tggatgtgct gaccggacac | 1440 |
| acagccacta atacccgcgt ggatgatggc ggaacgctga atgtccgcaa cggtggcacc | 1500 |
| gccaccaccg tatccatggg aaatggcggt gtactgctgg ccgattccgg tgccgctgtc | 1560 |
| agtggtaccc ggagcgacgg aaaggcattc agtatcggag gcggtcaggc ggatgccctg | 1620 |
| atgctggaaa aaggcagttc attcacgctg aacgccggtg atacggccac ggataccacg | 1680 |

```
gtaaatggcg gactgttcac cgccaggggc ggcacactgg cgggcaccac cacgctgaat    1740
aacggcgcca aggttaaac acccaagcag acgccgcaat atcagcacca acagaaaggt    1800
taagagagga caaaggtttc aacgcttcag caccagaaga tagagcgaca ggcaagtagc    1860
aat                                                                 1863
```

<210> SEQ ID NO 18
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 18

```
attgcuactt gcctgtcgct ctatcttctg gtgctgcagg tagaaagaag cagaatcgga     60
ttaacctact tgcctgtcgc tctatcttcg gcgtctgctt gggtgtttaa ccgtctctct    120
tgtccgtgca atagctcaat aatagaataa aacgatcaat atctatttta tcgatcgttt    180
atatcgatcg ataagctaat aataacctt gtcagtaaca tgcacagata cgtacagaaa    240
gacattcagg gaacaacaga accacaattc agaaactccc acagccggac ctccggcact    300 gtaaccctt acctgccggt atccacgttt gtgggtaccg gcttttttat tcaccctcaa    360
tctaaggaaa agctgatgaa acgacatctg aatacctgct acaggctggt atggaatcac    420
atgacgggcg ctttcgtggt tgcctccgaa ctggcccgcg cacggggtaa acgtggcggt    480
gtggcggttg cactgtctct tgccgcagtc acgtcactcc cggtgctggc tgctgacatc    540
gttgtgcacc cggagaaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa acgactgtc    720 accagtggtg gtcttcagag agtgaacccc ggtggaagtg tctcagacac ggttatcagt    780 gccgaggcg gacagagcct tcagggacgg gctgtgaaca ccacgctgaa tggtggcgaa    840
cagtggatgc atgagggggc gatagccaca ggaaccgtca ttaatgataa gggctggcag    900
gtcgtcaagc ccggtacagt ggcaacggat accgttgtta taccggggc ggaagggga    960 ccggatgcag aaaacggtga taccgggcag tttgttcgcg gggatgccgt acgcacaacc    1020
atcaataaaa acggtcgcca gattgtgaga gctgaaggaa cggcaaatac cactgtggtt    1080
tatgccggcg gcgaccagac tgtacatggt cacgcactgg ataccacgct gaatgggga    1140 taccagtatg tgcacaacgg cggtacagcg tctgacactg ttgtgaacag tgacggctgg    1200
cagattgtca aaacgggg tgtggccggg aataccaccg ttaatcagaa gggcagactg    1260
caggtggacg ccggtggtac agccacgaat gtcaccctga gcagggcgg cgcactggtt    1320 accagtacgg ctgcaaccgt taccggcata accgcctgg gagcattctc tgttgtggag    1380
ggtaaagctg ataatgtcgt actggaaaat ggcggacgcc tggatgtgct gaccggacac    1440
acagccacta ataccccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccaggggc ggcacactgg cgggcaccac cacgctgaat    1740
```

```
aacggcgcca aaggttaaac acccaagcag acgccgcaat atcagcacca acagaaaggt    1800
taatccgatt ctgcttcttt ctacctgcag caccagaaga tagagcgaca ggcaagtagc    1860
aat                                                                  1863

<210> SEQ ID NO 19
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 19
attgcuactt gcctgtcgct ctatcttctg gtgctgagaa cgacttccat actcgtgtga      60
ttaacctact tgcctgtcgc tctatcttcg gcgtctgctt gggtgtttaa ccgtctctct     120
tgtccgtgca atagctcaat aatagaataa acgatcaat atctatttta tcgatcgttt      180
atatcgatcg ataagctaat aataacctt gtcagtaaca tgcacagata cgtacagaaa     240
gacattcagg gaacaacaga accacaattc agaaactccc acagccggac ctccggcact     300
gtaacccttt acctgccggt atccacgttt gtgggtaccg cttttttat tcaccctcaa     360 tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cggagaaaac cgtgaacggc ggaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa acgactgtc      720 accagtggtg gtcttcagag agtgaacccc ggtggaagtg tctcagacac ggttatcagt     780
gccggaggcg gacagagcct tcagggacgg gctgtgaaca ccacgctgaa tggtggcgaa     840
cagtggatgc atgagggggc gatagccaca ggaaccgtca ttaatgataa gggctggcag     900
gtcgtcaagc ccggtacagt ggcaacggat accgttgtta ataccggggc ggaaggggga     960
ccggatgcag aaaacggtga taccgggcag tttgttcgcg gggatgccgt acgcacaacc    1020
atcaataaaa acggtcgcca gattgtgaga gctgaaggaa cggcaaatac cactgtggtt    1080
tatgccggcg cgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga agcagggcgg cgcactggtt    1320
accagtacgg ctgcaaccgt taccggcata accgcctgg gagcattctc tgttgtggag     1380
ggtaaagctg ataatgtcgt actggaaaat ggcggacgcc tggatgtgct gaccggacac    1440
acagccacta taccccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccaggggc ggcacactgg cgggcaccac cacgctgaat    1740
```

| | | |
|---|---|---|
| aacggcgcca aaggttaaac acccaagcag acgccgcaat atcagcacca acagaaaggt | 1800 | |
| taatcacacg agtatggaag tcgttctcag caccagaaga tagagcgaca ggcaagtagc | 1860 | |
| aat | 1863 | |

<210> SEQ ID NO 20
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 20

| | | |
|---|---|---|
| attgcuactt gcctgtcgct ctatcttctg gtgctgaggt ctacctcgct aacaccactg | 60 | |
| ttaacctact tgcctgtcgc tctatcttcg gcgtctgctt gggtgtttaa ccgtctctct | 120 | |
| tgtccgtgca atagctcaat aatagaataa aacgatcaat atctatttta tcgatcgttt | 180 | |
| atatcgatcg ataagctaat aataaccttt gtcagtaaca tgcacagata cgtacagaaa | 240 | |
| gacattcagg gaacaacaga accacaattc agaaactccc acagccggac ctccggcact | 300 | |
| gtaacccttt acctgccggt atccacgttt gtgggtaccg gctttttat tcaccctcaa | 360 | |
| tctaaggaaa agctgatgaa acgacatctg aatacctgct acaggctggt atggaatcac | 420 | |
| atgacgggcg ctttcgtggt tgcctccgaa ctggcccgcg cacggggtaa acgtggcggt | 480 | |
| gtggcggttg cactgtctct tgccgcagtc acgtcactcc cggtgctggc tgctgacatc | 540 | |
| gttgtgcacc cggagaaaac cgtgaacggc ggaacactgg caaatcatga caaccagatt | 600 | |
| gtcttcggta cgaccaacgg aatgaccatc agtaccgggc tggagtatgg gccggataac | 660 | |
| gaggccaata ccggcgggca atgggtacag gatggcggaa cagccaacaa acgactgtc | 720 | |
| accagtggtg gtcttcagag agtgaacccc ggtggaagtg tctcagacac ggttatcagt | 780 | |
| gccggaggcg gacagagcct tcagggacgg gctgtgaaca ccacgctgaa tggtggcgaa | 840 | |
| cagtggatgc atgagggggc gatagccaca ggaaccgtca ttaatgataa gggctggcag | 900 | |
| gtcgtcaagc ccggtacagt ggcaacggat accgttgtta ataccggggc ggaagggga | 960 | |
| ccggatgcag aaaacggtga taccgggcag tttgttcgcg gggatgccgt acgcacaacc | 1020 | |
| atcaataaaa acggtcgcca gattgtgaga gctgaaggaa cggcaaatac cactgtggtt | 1080 | |
| tatgccggcg cgaccagac tgtacatggt cacgcactgg ataccacgct gaatggggga | 1140 | |
| taccagtatg tgcacaacgg cggtacagcg tctgacactg ttgtgaacag tgacggctgg | 1200 | |
| cagattgtca aaaacggggg tgtggccggg aataccaccg ttaatcagaa gggcagactg | 1260 | |
| caggtggacg ccggtggtac agccacgaat gtcaccctga agcagggcgg cgcactggtt | 1320 | |
| accagtacgg ctgcaaccgt taccggcata aaccgcctgg gagcattctc tgttgtggag | 1380 | |
| ggtaaagctg ataatgtcgt actggaaaat ggcggacgcc tggatgtgct gaccggacac | 1440 | |
| acagccacta ataccgcgt ggatgatggc ggaacgctgg atgtccgcaa cggtggcacc | 1500 | |
| gccaccaccg tatccatggg aaatggcggt gtactgctgg ccgattccgg tgccgctgtc | 1560 | |
| agtggtaccc ggagcgacgg aaaaggcatt cagtatcgga gcggtcaggc ggatgccctg | 1620 | |
| atgctggaaa aaggcagttc attcacgctg aacgccggtg atacggccac ggataccacg | 1680 | |
| gtaaatggcg gactgttcac cgccagggc ggcacactgg cgggcaccac cacgctgaat | 1740 | |
| aacggcgcca aaggttaaac acccaagcag acgccgcaat atcagcacca acagaaaggt | 1800 |

```
taacagtggt gttagcgagg tagacctcag caccagaaga tagagcgaca ggcaagtagc    1860
aat                                                                 1863

<210> SEQ ID NO 21
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 21
attgcuactt gcctgtcgct ctatcttctg gtgctgaccc tccaggaaag tacctctgat      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataacccttt gtcagtaaca tgcacagata cgtacagaaa    240
gacattcagg gaacaacaga accacaattc agaaactccc acagccggac ctccggcact     300
gtaacccttt acctgccggt atccacgttt gtgggtaccg gctttttat tcaccctcaa     360 tctaaggaaa agctgatgaa acgacatctg aatacctgct acaggctggt atggaatcac     420
atgacgggcg ctttcgtggt tgcctccgaa ctggcccgcg cacggggtaa acgtggcggt    480
gtggcggttg cactgtctct tgccgcagtc acgtcactcc cggtgctggc tgctgacatc    540
gttgtgcacc cgggagaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa aacgactgtc    720
accagtggtg gtcttcagag agtgaacccc ggtggaagtg tctcagacac ggttatcagt    780
gccggaggcg gacagagcct tcagggacgg gctgtgaaca ccacgctgaa tggtggcgaa    840
cagtggatgc atgaggggc gatagccaca ggaaccgtca ttaatgataa gggctggcag    900
gtcgtcaagc ccggtacagt ggcaacggat accgttgtta ataccggggc ggaaggggga    960
ccggatgcag aaaacggtga taccgggcag tttgttcgcg gggatgccgt acgcacaacc    1020
atcaataaaa acgtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga gcagggcgg cgcactggtt    1320 accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta tacccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag cggtcaggc ggatgccctg    1620 atgctggaaa aaggcagttc attcacgctg aacgccggtg atacggccac ggataccacg    1680
gtaaatggcg gactgttcac cgccagggc ggcacactgg cggcaccac cacgctgaat    1740 aacggcgcca aaggttaaac acccaagcag acgccgcaat atcagcacca acagaaaggt    1800
```

```
taaatcagag gtactttcct ggagggtcag caccagaaga tagagcgaca ggcaagtagc    1860
aat                                                                 1863

<210> SEQ ID NO 22
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 22
attgcuactt gcctgtcgct ctatcttctg gtgctggttc ctcgtgcagt gtcaagagat     60
ttaacctact tgcctgtcgc tctatcttcg gcgtctgctt gggtgtttaa ccgtctctct    120
tgtccgtgca atagctcaat aatagaataa aacgatcaat atctatttta tcgatcgttt    180
atatcgatcg ataagctaat aataaccttt gtcagtaaca tgcacagata cgtacagaaa    240
gacattcagg gaacaacaga accacaattc agaaactccc acagccggac ctccggcact    300 gtaaccettt acctgccggt atccacgttt gtgggtaccg gctttttat tcaccctcaa    360 tctaaggaaa agctgatgaa acgacatctg aatacctgct acaggctggt atggaatcac    420
atgacgggcg ctttcgtggt tgcctccgaa ctggcccgcg cacggggtaa acgtggcggt    480
gtggcggttg cactgtctct tgccgcagtc acgtcactcc cggtgctggc tgctgacatc    540
gttgtgcacc cggagaaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa acgactgtc    720 accagtggtg gtcttcagag agtgaacccc ggtggaagtg tctcagacac ggttatcagt    780 gccgaggcg gacagagcct tcagggacgg gctgtgaaca ccacgctgaa tggtggcgaa    840
cagtggatgc atgagggggc gatagccaca ggaaccgtca ttaatgataa gggctggcag    900
gtcgtcaagc ccggtacagt ggcaacggat accgttgtta ataccggggc ggaaggggga    960
ccggatgcag aaaacggtga taccgggcag tttgttcgcg gggatgccgt acgcacaacc    1020
atcaataaaa acggtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcc tctgacactg ttgtgaacag tgacggctgg    1200
cagattgtca aaacgggggg tgtggccggg aataccaccg ttaatcagaa gggcagactg    1260
caggtggacg ccggtggtac agccacgaat gtcaccctga gcagggcgg cgcactggtt    1320 accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta tacccgcgt ggatgatggc ggaacgctat atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccagggc ggcacactgg cggcaccac cacgctgaat    1740 aacgcgcca aaggttaaac acccaagcag acgccgcaat atcagcacca acagaaaggt    1800
taaatctctt gacactgcac gaggaaccag caccagaaga tagagcgaca ggcaagtagc    1860
``` aat                                                                      1863

<210> SEQ ID NO 23
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 23

```
attgcuacttt gcctgtcgct ctatcttctg gtgctgttgc gtcctgttac gagaactcat      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataacccttt gtcagtaaca tgcacagata cgtacagaaa     240
gacattcagg gaacaacaga accacaattc agaaactccc acagccggac ctccggcact     300
gtaaccctt  acctgccggt atccacgttt gtgggtaccg gctttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cgggagaaac cgtgaacggc ggaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa aacgactgtc     720
accagtggtg gtcttcagag agtgaacccc ggtggaagtg tctcagacac ggttatcagt     780
gccgaggcg  gacagagcct tcagggacgg gctgtgaaca ccacgctgaa tggtggcgaa     840
cagtggatgc atgaggggc  gatagccaca ggaaccgtca ttaatgataa gggctggcag     900
gtcgtcaagc ccggtacagt ggcaacggat accgttgtta ataccggggc ggaaggggga     960
ccggatgcag aaaacggtga taccgggcag tttgttcgcg gggatgccgt acgcacaacc    1020
atcaataaaa acgtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga agcagggcgg cgcactggtt    1320
accagtacgc ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta ataccccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacgccac  ggataccacg    1680
gtaaatggcg gactgttcac cgccagggc  ggcacactgg cgggcaccac cacgctgaat    1740
aacggcgcca aggttaaac  acccaagcag acgccgcaat atcagcacca acagaaaggt    1800
taaatgagtt ctcgtaacag gacgcaacag caccagaaga tagagcgaca ggcaagtagc    1860
``` aat                                                                1863

<210> SEQ ID NO 24
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 24

```
attgcuactt gcctgtcgct ctatcttctg gtgctgctta ctacccagtg aacctcctcg      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataacctttt gtcagtaaca tgcacagata cgtacagaaa     240
gacattcagg gaacaacaga accacaattc agaaactccc acagccggac ctccggcact     300 gtaaccctttt acctgccggt atccacgttt gtgggtaccg gcttttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cggagaaac cgtgaacggc ggaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa acgactgtc     720 accagtggtg gtcttcagag agtgaacccc ggtggaagtg tctcagacac ggttatcagt     780
gccggaggcg gacagagcct tcagggacgg gctgtgaaca ccacgctgaa tggtggcgaa     840
cagtggatgc atgaggggc gatagccaca ggaaccgtca ttaatgataa gggctggcag     900
gtcgtcaagc ccggtacagt ggcaacggat accgttgtta ataccggggc ggaaggggga     960
ccggatgcag aaaacggtga taccgggcag tttgttcgcg gggatgccgt acgcacaacc    1020
atcaataaaa acgtcgcca gattgtgaga gctgaaggaa cggcaaatac cactgtggtt    1080
tatgccggcg cgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga agcagggcgg cgcactggtt    1320
accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta atacccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccaggggc ggcacactgg cgggcaccac cacgctgaat    1740
aacggcgcca aaggttaaac acccaagcag acgccgcaat atcagcacca acagaaaggt    1800
taacgaggag gttcactggg tagtaagcag caccagaaga tagagcgaca ggcaagtagc    1860
aat                                                                 1863
```

<210> SEQ ID NO 25
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 25

| | | | | | | |
|---|---|---|---|---|---|---|
| attgcuactt | gcctgtcgct | ctatcttctg | gtgctggcat | agttctgcat | gatgggttag | 60 |
| ttaacctact | tgcctgtcgc | tctatcttcg | gcgtctgctt | gggtgtttaa | ccgtctctct | 120 |
| tgtccgtgca | atagctcaat | aatagaataa | aacgatcaat | atctatttta | tcgatcgttt | 180 |
| atatcgatcg | ataagctaat | aataaccttt | gtcagtaaca | tgcacagata | cgtacagaaa | 240 |
| gacattcagg | gaacaacaga | accacaattc | agaaactccc | acagccggac | ctccggcact | 300 |
| gtaacccttt | acctgccggt | atccacgttt | gtgggtaccg | gcttttttat | tcaccctcaa | 360 |
| tctaaggaaa | agctgatgaa | acgacatctg | aatacctgct | acaggctggt | atggaatcac | 420 |
| atgacgggcg | ctttcgtggt | tgcctccgaa | ctggcccgcg | cacggggtaa | acgtggcggt | 480 |
| gtggcggttg | cactgtctct | tgccgcagtc | acgtcactcc | cggtgctggc | tgctgacatc | 540 |
| gttgtgcacc | cgggagaaac | cgtgaacggc | ggaacactgg | caaatcatga | caaccagatt | 600 |
| gtcttcggta | cgaccaacgg | aatgaccatc | agtaccgggc | tggagtatgg | gccggataac | 660 |
| gaggccaata | ccggcgggca | atgggtacag | gatggcggaa | cagccaacaa | aacgactgtc | 720 |
| accagtggtg | gtcttcagag | agtgaacccc | ggtggaagtg | tctcagacac | ggttatcagt | 780 |
| gccggaggcg | gacagagcct | tcagggacgg | gctgtgaaca | ccacgctgaa | tggtggcgaa | 840 |
| cagtggatgc | atgaggggc | gatagccaca | ggaaccgtca | ttaatgataa | gggctggcag | 900 |
| gtcgtcaagc | ccggtacagt | ggcaacggat | accgttgtta | ataccggggc | ggaagggga | 960 |
| ccggatgcag | aaaacggtga | taccgggcag | tttgttcgcg | gggatgccgt | acgcacaacc | 1020 |
| atcaataaaa | acgtcgcca | gattgtgaga | gctgaaggaa | cggcaaatac | cactgtggtt | 1080 |
| tatgccggcg | gcgaccagac | tgtacatggt | cacgcactgg | ataccacgct | gaatggggga | 1140 |
| taccagtatg | tgcacaacgg | cggtacagcg | tctgacactg | ttgtgaacag | tgacggctgg | 1200 |
| cagattgtca | aaacggggg | tgtggccggg | aataccaccg | ttaatcagaa | gggcagactg | 1260 |
| caggtggacg | ccggtggtac | agccacgaat | gtcacccctga | agcagggcgg | cgcactggtt | 1320 |
| accagtacgg | ctgcaaccgt | taccggcata | aaccgcctgg | gagcattctc | tgttgtggag | 1380 |
| ggtaaagctg | ataatgtcgt | actggaaaat | ggcggacgcc | tggatgtgct | gaccggacac | 1440 |
| acagccacta | ataccgcgt | ggatgatggc | ggaacgctgg | atgtccgcaa | cggtggcacc | 1500 |
| gccaccaccg | tatccatggg | aaatggcggt | gtactgctgg | ccgattccgg | tgccgctgtc | 1560 |
| agtggtaccc | ggagcgacgg | aaaggcattc | agtatcggag | gcggtcaggc | ggatgccctg | 1620 |
| atgctggaaa | aaggcagttc | attcacgctg | aacgccggtg | atacggccac | ggataccacg | 1680 |
| gtaaatggcg | gactgttcac | cgccaggggc | ggcacactgg | cgggcaccac | cacgctgaat | 1740 |
| aacggcgcca | aaggttaaac | acccaagcag | acgccgcaat | atcagcacca | acagaaaggt | 1800 |
| taactaaccc | atcatgcaga | actatgccag | caccagaaga | tagagcgaca | ggcaagtagc | 1860 |
| aat | | | | | | 1863 |

<210> SEQ ID NO 26
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 26

```
attgcuactt gcctgtcgct ctatcttctg gtgctgcata cagcgactac gcattctcat      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataaccttt gtcagtaaca tgcacagata cgtacagaaa     240
gacattcagg gaacaacaga accacaattc agaaactccc acagccggac ctccggcact     300
gtaaccctttt acctgccggt atccacgttt gtgggtaccg gcttttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cggagaaaac cgtgaacggc ggaaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa aacgactgtc     720
accagtggtg gtcttcagag agtgaacccc ggtggaagtg tctcagacac ggttatcagt     780
gccgaggcg acagagcct tcagggacgg gctgtgaaca ccacgctgaa tggtggcgaa     840
cagtggatgc atgagggggc gatagccaca ggaaccgtca ttaatgataa gggctggcag     900
gtcgtcaagc ccggtacagt ggcaacggat accgttgtta ataccggggc ggaaggggga     960
ccggatgcag aaaacggtga taccgggcag tttgttcgcg gggatgccgt acgcacaacc    1020
atcaataaaa acgtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga gcagggcgg cgcactggtt    1320
accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta ataccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag cggtcaggc ggatgccctg    1620
atgctggaaa aaggcagttc attcacgctg aacgccggtg atacggccac ggataccacg    1680
gtaaatggcg gactgttcac cgccagggc ggcacactgg cggcaccac cacgctgaat    1740
aacggcgcca aaggttaaac acccaagcag acgccgcaat atcagcacca acagaaaggt    1800
taaatgagaa tgcgtagtcg ctgtatgcag caccagaaga tagagcgaca ggcaagtagc    1860
aat                                                                  1863
```

<210> SEQ ID NO 27
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 27

```
attgcuactt gcctgtcgct ctatcttctg gtgctgcgac ggttagattc acctcttaca    60
ttaacctact tgcctgtcgc tctatcttcg gcgtctgctt gggtgtttaa ccgtctctct   120
tgtccgtgca atagctcaat aatagaataa acgatcaat atctatttta tcgatcgttt    180
atatcgatcg ataagctaat aataacctt gtcagtaaca tgcacagata cgtacagaaa    240
gacattcagg gaacaacaga accacaattc agaaactccc acagccggac ctccggcact   300
gtaacccttt acctgccggt atccacgttt gtgggtaccg gctttttat tcaccctcaa    360
tctaaggaaa agctgatgaa acgacatctg aatacctgct acaggctggt atggaatcac   420
atgacgggcg ctttcgtggt tgcctccgaa ctggcccgcg cacggggtaa acgtggcggt   480
gtggcggttg cactgtctct tgccgcagtc acgtcactcc cggtgctggc tgctgacatc   540
gttgtgcacc cggagaaaac cgtgaacggc ggaacactgg caaatcatga caaccagatt   600
gtcttcggta cgaccaacgg aatgaccatc agtaccgggc tggagtatgg gccggataac   660
gaggccaata ccggcgggca atgggtacag gatggcggaa cagccaacaa acgactgtc    720
accagtggtg gtcttcagag agtgaacccc ggtggaagtg tctcagacac ggttatcagt   780
gccgaggcg acagagcct tcagggacgg gctgtgaaca ccacgctgaa tggtggcgaa    840
cagtggatgc atgaggggggc gatagccaca ggaaccgtca ttaatgataa gggctggcag   900
gtcgtcaagc ccggtacagt ggcaacggat accgttgtta taccggggc ggaaggggga    960
ccggatgcag aaaacggtga taccgggcag tttgttcgcg gggatgccgt acgcacaacc  1020
atcaataaaa acgtcgcca gattgtgaga gctgaaggaa cggcaaatac cactgtggtt  1080
tatgccggcg gcgaccagac tgtacatggt cacgcactgg ataccacgct gaatggggga  1140
taccagtatg tgcacaacgg cggtacagcg tctgacactg ttgtgaacag tgacggctgg  1200
cagattgtca aaaacggggg tgtggccggg aataccaccg ttaatcagaa gggcagactg  1260
caggtggacg ccggtggtac agccacgaat gtcaccctga agcagggcgg cgcactggtt  1320
accagtacgc ctgcaaccgt taccggcata accgcctgg gagcattctc tgttgtggag  1380
ggtaaagctg ataatgtcgt actggaaaat ggcggacgcc tggatgtgct gaccggacac  1440
acagccacta atacccgcgt ggatgatggc ggaacgctgg atgtccgcaa cggtggcacc  1500
gccaccaccg tatccatggg aaatggcggt gtactgctgg ccgattccgg tgccgctgtc  1560
agtggtaccc ggagcgacgg aaaggcattc agtatcggag gcggtcaggc ggatgccctg  1620
atgctggaaa aaggcagttc attcacgctg aacgccggtg atacggccac ggataccacg  1680
gtaaatggcg gactgttcac cgccagggc ggcacactgg cgggcaccac cacgctgaat  1740
aacggcgcca aaggttaaac acccaagcag acgccgcaat atcagcacca acagaaaggt  1800
taatgtaaga ggtgaatcta accgtcgcag caccagaaga tagagcgaca ggcaagtagc  1860
aat                                                                1863
```

<210> SEQ ID NO 28

<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 28

| | | | | | |
|---|---|---|---|---|---|
| attgcuacttt | gcctgtcgct | ctatcttctg | gtgctgctag | acaccttggg | ttgacagacc | 60 |
| ttaacctact | tgcctgtcgc | tctatcttcg | gcgtctgctt | gggtgtttaa | ccgtctctct | 120 |
| tgtccgtgca | atagctcaat | aatagaataa | aacgatcaat | atctatttta | tcgatcgttt | 180 |
| atatcgatcg | ataagctaat | aataacccttt | gtcagtaaca | tgcacagata | cgtacagaaa | 240 |
| gacattcagg | gaacaacaga | accacaattc | agaaactccc | acagccggac | ctccggcact | 300 |
| gtaacccttt | acctgccggt | atccacgttt | gtgggtaccg | gcttttttat | tcaccctcaa | 360 |
| tctaaggaaa | agctgatgaa | acgacatctg | aatacctgct | acaggctggt | atggaatcac | 420 |
| atgacgggcg | ctttcgtggt | tgcctccgaa | ctggcccgcg | cacggggtaa | acgtggcggt | 480 |
| gtggcggttg | cactgtctct | tgccgcagtc | acgtcactcc | cggtgctggc | tgctgacatc | 540 |
| gttgtgcacc | cggagaaaac | cgtgaacggc | ggaacactgg | caaatcatga | caaccagatt | 600 |
| gtcttcggta | cgaccaacgg | aatgaccatc | agtaccgggc | tggagtatgg | gccggataac | 660 |
| gaggccaata | ccggcgggca | atgggtacag | gatggcggaa | cagccaacaa | aacgactgtc | 720 |
| accagtggtg | gtcttcagag | agtgaacccc | ggtggaagtg | tctcagacac | ggttatcagt | 780 |
| gccggaggcg | gacagagcct | tcagggacgg | gctgtgaaca | ccacgctgaa | tggtggcgaa | 840 |
| cagtggatgc | atgaggggcg | gatagccaca | ggaaccgtca | ttaatgataa | gggctggcag | 900 |
| gtcgtcaagc | ccggtacagt | ggcaacggat | accgttgtta | ataccggggc | ggaaggggga | 960 |
| ccggatgcag | aaaacggtga | taccgggcag | tttgttcgcg | gggatgccgt | acgcacaacc | 1020 |
| atcaataaaa | acggtcgcca | gattgtgaga | gctgaaggaa | cggcaaatac | cactgtggtt | 1080 |
| tatgccggcg | gcgaccagac | tgtacatggt | cacgcactgg | ataccacgct | gaatggggga | 1140 |
| taccagtatg | tgcacaacgg | cggtacagcg | tctgacactg | ttgtgaacag | tgacggctgg | 1200 |
| cagattgtca | aaaacggggg | tgtggccggg | aataccaccg | ttaatcagaa | gggcagactg | 1260 |
| caggtggacg | ccggtggtac | agccacgaat | gtcaccctga | agcagggcgg | cgcactggtt | 1320 |
| accagtacgg | ctgcaaccgt | taccggcata | aaccgcctgg | gagcattctc | tgttgtggag | 1380 |
| ggtaaagctg | ataatgtcgt | actggaaaat | ggcggacgcc | tggatgtgct | gaccggacac | 1440 |
| acagccacta | ataccgcgt | ggatgatggc | ggaacgctgg | atgtccgcaa | cggtggcacc | 1500 |
| gccaccaccg | tatccatggg | aaatggcggt | gtactgctgg | ccgattccgg | tgccgctgtc | 1560 |
| agtggtaccc | ggagcgacgg | aaaggcattc | agtatcggag | gcggtcaggc | ggatgccctg | 1620 |
| atgctggaaa | aaggcagttc | attcacgctg | aacgccggtg | atacggccac | ggataccacg | 1680 |
| gtaaatggcg | gactgttcac | cgccaggggc | ggcacactgg | cgggcaccac | cacgctgaat | 1740 |
| aacggcgcca | aaggttaaac | acccaagcag | acgccgcaat | atcagcacca | acagaaaggt | 1800 |
| taaggtctgt | caacccaagg | tgtctagcag | caccagaaga | tagagcgaca | ggcaagtagc | 1860 |
| aat | | | | | | 1863 |

<210> SEQ ID NO 29
<211> LENGTH: 1863

<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 29

```
attgcuactt gcctgtcgct ctatcttctg gtgctgtcag tgaggatcta cttcgaccca      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataaccttt gtcagtaaca tgcacagata cgtacagaaa     240
gacattcagg gaacaacaga accacaattc agaaactccc acagccggac ctccggcact     300
gtaacccttt acctgccggt atccacgttt gtgggtaccg gcttttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cggagaaaac cgtgaacggc ggaacactgg caaatcatga caaccagatt     600
gtcttcggta cgaccaacgg aatgaccatc agtaccgggc tggagtatgg gccgataaac     660
gaggccaata ccggcgggca atgggtacag gatggcggaa cagccaacaa aacgactgtc     720
accagtggtg gtcttcagag agtgaacccc ggtggaagtg tctcagacac ggttatcagt     780
gccggaggcg gacagagcct tcagggacgg gctgtgaaca ccacgctgaa tggtggcgaa     840
cagtggatgc atgagggggc gatagccaca ggaaccgtca ttaatgataa gggctggcag     900
gtcgtcaagc ccggtacagt ggcaacggat accgttgtta ataccggggc ggaaggggga     960
ccggatgcag aaaacggtga taccgggcag tttgttcgcg gggatgccgt acgcacaacc    1020
atcaataaaa acggtcgcca gattgtgaga gctgaaggaa cggcaaatac cactgtggtt    1080
tatgccggcg cgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga gcagggcgg cgcactggtt    1320
accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta ataccccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccaggggc ggcacactgg cgggcaccac cacgctgaat    1740
aacggcgcca aaggttaaac acccaagcag acgccgcaat atcagcacca acagaaaggt    1800
taatgggtcg aagtagatcc tcactgacag caccagaaga tagagcgaca ggcaagtagc    1860
aat                                                                 1863
```

<210> SEQ ID NO 30
<211> LENGTH: 1863
<212> TYPE: DNA

<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 30

```
attgcuactt gcctgtcgct ctatcttctg gtgctgtgcg tacagcaatc agttacattg      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataaccttt gtcagtaaca tgcacagata cgtacagaaa     240
gacattcagg gaacaacaga accacaattc agaaactccc acagccggac ctccggcact     300
gtaacccttt acctgccggt atccacgttt gtgggtaccg gcttttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cggagaaaac cgtgaacggc ggaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa aacgactgtc     720
accagtggtg gtcttcagag agtgaacccc ggtggaagtg tctcagacac ggttatcagt     780
gccggaggcg gacagagcct tcagggacgg gctgtgaaca ccacgctgaa tggtggcgaa     840
cagtggatgc atgagggggc gatagccaca ggaaccgtca ttaatgataa gggctggcag     900
gtcgtcaagc ccgtacagt ggcaacggat accgttgtta taccggggc ggaaggggga     960
ccggatgcag aaaacggtga taccgggcag tttgttcgcg gggatgccgt acgcacaacc    1020
atcaataaaa acgtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga agcagggcgg cgcactggtt    1320
accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta ataccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccaggggc ggcacactgg cgggcaccac cacgctgaat    1740
aacggcgcca aggttaaac acccaagcag acgccgcaat atcagcacca acagaaaggt    1800
taacaatgta actgattgct gtacgcacag caccagaaga tagagcgaca ggcaagtagc    1860
aat                                                                  1863
```

<210> SEQ ID NO 31
<211> LENGTH: 1863
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 31

```
attgcuactt gcctgtcgct ctatcttctg gtgctgccag tagaagtccg acaacgtcat      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataaccttt gtcagtaaca tgcacagata cgtacagaaa     240
gacattcagg gaacaacaga accacaattc agaaactccc acagccggac ctccggcact     300
gtaaccctt acctgccggt atccacgttt gtgggtaccg gcttttttat tcaccctcaa     360
tctaaggaaa agctgatgaa acgacatctg aatacctgct acaggctggt atggaatcac     420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cggagaaac cgtgaacggc ggaacactgg caaatcatga caaccagatt     600
gtcttcggta cgaccaacgg aatgaccatc agtaccgggc tggagtatgg gccggataac     660
gaggccaata ccggcgggca atgggtacag gatggcggaa cagccaacaa acgactgtc     720
accagtggtg gtcttcagag agtgaacccc ggtggaagtg tctcagacac ggttatcagt     780
gccgaggcg gacagagcct tcagggacgg gctgtgaaca ccacgctgaa tggtggcgaa     840
cagtggatgc atgaggggc gatagccaca ggaaccgtca ttaatgataa gggctggcag     900
gtcgtcaagc ccggtacagt ggcaacggat accgttgtta ataccggggc ggaaggggga     960
ccggatgcag aaaacggtga taccgggcag tttgttcgcg gggatgccgt acgcacaacc    1020
atcaataaaa acgtcgcca gattgtgaga gctgaaggaa cggcaaatac cactgtggtt    1080
tatgccggcg gcgaccagac tgtacatggt cacgcactgg ataccacgct gaatggggga    1140
taccagtatg tgcacaacgg cggtacagcg tctgacactg ttgtgaacag tgacggctgg    1200
cagattgtca aaaacggggg tgtggccggg aataccaccg ttaatcagaa gggcagactg    1260
caggtggacg ccggtggtac agccacgaat gtcaccctga agcagggcgg cgcactggtt    1320
accagtacgg ctgcaaccgt taccggcata aaccgcctgg gagcattctc tgttgtggag    1380
ggtaaagctg ataatgtcgt actggaaaat ggcggacgcc tggatgtgct gaccggacac    1440
acagccacta atacccgcgt ggatgatggc ggaacgctgg atgtccgcaa cggtggcacc    1500
gccaccaccg tatccatggg aaatggcggt gtactgctgg ccgattccgg tgccgctgtc    1560
agtggtaccc ggagcgacgg aaaggcattc agtatcggag gcggtcaggc ggatgccctg    1620
atgctggaaa aaggcagttc attcacgctg aacgccggtg atacggccac ggataccacg    1680
gtaaatggcg gactgttcac cgccagggc ggcacactgg cgggcaccac cacgctgaat    1740
aacggcgcca aggttaaac acccaagcag acgccgcaat atcagcacca acagaaaggt    1800
taaatgacgt tgtcggactt ctactggcag caccagaaga tagagcgaca ggcaagtagc    1860
aat                                                                  1863
```

<210> SEQ ID NO 32
<211> LENGTH: 1863
<212> TYPE: DNA
<213> ORGANISM: Artificial Sequence
<220> FEATURE:

<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 32

```
attgcuactt gcctgtcgct ctatcttctg gtgctgtagt ttggatgacc aaggatagcc      60
ttaacctact tgcctgtcgc tctatcttcg gcgtctgctt gggtgtttaa ccgtctctct     120
tgtccgtgca atagctcaat aatagaataa aacgatcaat atctatttta tcgatcgttt     180
atatcgatcg ataagctaat aataacccttt gtcagtaaca tgcacagata cgtacagaaa    240
gacattcagg gaacaacaga accacaattc agaaactccc acagccggac ctccggcact     300
gtaacccttt acctgccggt atccacgttt gtgggtaccg ctttttttat tcaccctcaa     360
tctaaggaaa agctgatgaa cgacatctg aatacctgct acaggctggt atggaatcac      420
atgacgggcg ctttcgtggt tgcctccgaa ctggcccgcg cacggggtaa acgtggcggt     480
gtggcggttg cactgtctct tgccgcagtc acgtcactcc cggtgctggc tgctgacatc     540
gttgtgcacc cggagaaaac cgtgaacggc ggaacactgg caaatcatga caaccagatt    600
gtcttcggta cgaccaacgg aatgaccatc agtaccgggc tggagtatgg gccggataac    660
gaggccaata ccggcgggca atgggtacag gatggcggaa cagccaacaa aacgactgtc    720
accagtggtg gtcttcagag agtgaacccc ggtggaagtg tctcagacac ggttatcagt    780
gccggaggcg gacagagcct tcagggacgg gctgtgaaca ccacgctgaa tggtggcgaa    840
cagtggatgc atgaggggggc gatagccaca ggaaccgtca ttaatgataa gggctggcag   900
gtcgtcaagc ccggtacagt ggcaacggat accgttgtta ataccggggc ggaagggga    960
ccggatgcag aaaacggtga taccgggcag tttgttcgcg gggatgccgt acgcacaacc  1020
atcaataaaa acgtcgcca gattgtgaga gctgaaggaa cggcaaatac cactgtggtt   1080
tatgccggcg cgaccagac tgtacatggt cacgcactgg ataccacgct gaatggggga   1140
taccagtatg tgcacaacgg cggtacagcg tctgacactg ttgtgaacag tgacggctgg  1200
cagattgtca aaaacggggg tgtggccggg aataccaccg ttaatcagaa gggcagactg  1260
caggtggacg ccggtggtac agccacgaat gtcaccctga agcagggcgg cgcactggtt  1320
accagtacgc ctgcaaccgt taccggcata aaccgcctgg gagcattctc tgttgtggag  1380
ggtaaagctg ataatgtcgt actggaaaat ggcggacgcc tggatgtgct gaccggacac  1440
acagccacta atacccgcgt ggatgatggc ggaacgctgg atgtccgcaa cggtggcacc  1500
gccaccaccg tatccatggg aaatggcggt gtactgctgg ccgattccgg tgccgctgtc  1560
agtggtaccc ggagcgacgg aaaggcattc agtatcggag gcggtcaggc ggatgccctg  1620
atgctggaaa aaggcagttc attcacgctg aacgccggtg atacggccac ggataccacg  1680
gtaaatggcg gactgttcac cgccaggggc ggcacactgg cggcaccac cacgctgaat  1740
aacggcgcca aaggttaaac acccaagcag acgccgcaat atcagcacca acagaaaggt  1800
taaggctatc cttggtcatc caaactacag caccagaaga tagagcgaca ggcaagtagc  1860
aat                                                                 1863
```

<210> SEQ ID NO 33
<211> LENGTH: 1077
<212> TYPE: DNA
<213> ORGANISM: Artificial Sequence
<220> FEATURE:
<223> OTHER INFORMATION: Synthetic reporter polynucleotide

```
<220> FEATURE:
<221> NAME/KEY: misc_feature
<222> LOCATION: (1)..(1)
<223> OTHER INFORMATION: 5' Biotinylation

<400> SEQUENCE: 33
attgcuactt gcctgtcgct ctatcttcta aggttaaaag aaagttgtcg gtgtctttgt      60
gcagcacctc actgcctggc cgtaaatacg cgtatcaaac ggaccaacat cattctggta     120
gtaattaacg tctaactgcg gctctgccga gtagctactg gtgttctgtt cgctgaaaac     180
ctggaactgc ttggttgaaa cggtggcatt gaagttttgc accgcatagc caacgctgaa     240
tttttgcgtt gcgtagccgt cagtactgga accgtacttg ttatcgaaat cattgaagta     300
gctaggatcg ctgaccttgg tgtagtcgac gttgaaacgc cacacctgat ccatgacccc     360
ggagtggttc cagtagaata accaacgacg tgaactgtca tcgttcgggt gttcatcttc     420
atagacttta tctgaaggca gatagtccag ttccatcaag ccagcgcccg cctgggagag     480
gtagcggaat tcgttctccc acatgatgtt gccacgacga tgcatataat gcggcgtgat     540
ggtggcatcc atatttggcg cgatgttcca gtaatatggc aggtagaact caaagtagtt     600
ggtggtggtg tacttggcgt tcgggatcaa gaaaccagag cgacgtttgt cacccaccgg     660
caactgcaaa taggggctat aaaagatcgg taccggaccc accttaaagc gggcgttcca     720
gatctccgca acttgttctt cgcggtcatg aataatttcg ctacctacca cgctccaggt     780
gtcagaaccc ggcagacagg aggtaaagct accgttatcc agaatggtat agcggttttc     840
gccacgttgt ttcatcaggt ccgctttacc gcgaccctgg cgacccacca tctggtaatc     900
accttcccag acgttggtat ctttggtgtt cagattcgcc cagcctttcg gcccttgag      960
gatcacctgg ttatcgtcgt aatggacatt accgagcgca tcaacaggtg ctgcacaaag    1020
acaccgacaa ctttctttta accttgccag caatatcagc accaacagaa aagcaat       1077

<210> SEQ ID NO 34
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 34
attgcuactt gcctgtcgct ctatcttcta aggttaatcg attccgtttg tagtcgtctg      60
tcagcacctc actgcctggc cgtaaatacg cgtatcaaac ggaccaacat cattctggta     120
gtaattaacg tctaactgcg gctctgccga gtagctactg gtgttctgtt cgctgaaaac     180
ctggaactgc ttggttgaaa cggtggcatt gaagttttgc accgcatagc caacgctgaa     240
tttttgcgtt gcgtagccgt cagtactgga accgtacttg ttatcgaaat cattgaagta     300
gctaggatcg ctgaccttgg tgtagtcgac gttgaaacgc cacacctgat ccatgacccc     360
ggagtggttc cagtagaata accaacgacg tgaactgtca tcgttcgggt gttcatcttc     420
atagacttta tctgaaggca gatagtccag ttccatcaag ccagcgcccg cctgggagag     480
gtagcggaat tcgttctccc acatgatgtt gccacgacga tgcatataat gcggcgtgat     540
ggtggcatcc atatttggcg cgatgttcca gtaatatggc aggtagaact caaagtagtt     600
ggtggtggtg tacttggcgt tcgggatcaa gaaaccagag cgacgtttgt cacccaccgg     660
```

```
caactgcaaa tagggctat aaaagatcgg taccggaccc accttaaagc gggcgttcca      720
gatctccgca acttgttctt cgcggtcatg aataatttcg ctacctacca cgctccaggt      780
gtcagaaccc ggcagacagg aggtaaagct accgttatcc agaatggtat agcggttttc      840
gccacgttgt ttcatcaggt ccgctttacc gcgaccctgg cgaccacca tctggtaatc        900 accttcccag acgttggtat ctttggtgtt cagattcgcc cagcctttcg gccctttgag      960
gatcacctgg ttatcgtcgt aatggacatt accgagcgca tcaacaggtg ctgacagacg     1020
actacaaacg gaatcgatta accttgccag caatatcagc accaacagaa aagcaat       1077
```

<210> SEQ ID NO 35
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 35

```
attgcuactt gcctgtcgct ctatcttcta aggttaagag tcttgtgtcc cagttaccag       60
gcagcacctc actgcctggc cgtaaatacg cgtatcaaac ggaccaacat cattctggta      120
gtaattaacg tctaactgcg gctctgccga gtagctactg gtgttctgtt cgctgaaaac      180
ctggaactgc ttggttgaaa cggtggcatt gaagttttgc accgcatagc caacgctgaa     240
tttttgcgtt gcgtagccgt cagtactgga accgtacttg ttatcgaaat cattgaagta     300
gctaggatcg ctgaccttgg tgtagtcgac gttgaaacgc cacacctgat ccatgacccc    360
ggagtggttc cagtagaata ccaacgacg tgaactgtca tcgttcgggt gttcatcttc      420
atagacttta tctgaaggca gatagtccag ttccatcaag ccagcgcccg cctgggagag    480
gtagcggaat tcgttctccc acatgatgtt gccacgacga tgcatataat gcggcgtgat    540
ggtggcatcc atatttggcg cgatgttcca gtaatatggc aggtagaact caaagtagtt    600
ggtggtggtg tacttggcgt tcgggatcaa gaaaccagag cgacgtttgt cacccaccgg   660
caactgcaaa tagggctat aaaagatcgg taccggaccc accttaaagc gggcgttcca     720
gatctccgca acttgttctt cgcggtcatg aataatttcg ctacctacca cgctccaggt    780
gtcagaaccc ggcagacagg aggtaaagct accgttatcc agaatggtat agcggttttc    840
gccacgttgt ttcatcaggt ccgctttacc gcgaccctgg cgaccacca tctggtaatc     900 accttcccag acgttggtat ctttggtgtt cagattcgcc cagcctttcg gccctttgag    960
gatcacctgg ttatcgtcgt aatggacatt accgagcgca tcaacaggtg ctgcctggta  1020
actgggacac aagactctta accttgccag caatatcagc accaacagaa aagcaat      1077
```

<210> SEQ ID NO 36
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 36

```
attgcuactt gcctgtcgct ctatcttcta aggttaattc ggattctatc gtgtttccct       60
```

```
acagcacctc actgcctggc cgtaaatacg cgtatcaaac ggaccaacat cattctggta    120
gtaattaacg tctaactgcg gctctgccga gtagctactg tgttctgtt cgctgaaaac    180 ctggaactgc ttggttgaaa cggtggcatt gaagttttgc accgcatagc caacgctgaa    240
tttttgcgtt gcgtagccgt cagtactgga accgtacttg ttatcgaaat cattgaagta    300
gctaggatcg ctgaccttgg tgtagtcgac gttgaaacgc cacacctgat ccatgacccc    360
ggagtggttc cagtagaata accaacgacg tgaactgtca tcgttcgggt gttcatcttc    420
atagacttta tctgaaggca gatagtccag ttccatcaag ccagcgcccg cctgggagag    480
gtagcggaat tcgttctccc acatgatgtt gccacgacga tgcatataat gcggcgtgat    540
ggtggcatcc atatttggcg cgatgttcca gtaatatggc aggtagaact caaagtagtt    600
ggtggtggtg tacttggcgt tcgggatcaa gaaaccagag cgacgtttgt cacccaccgg    660
caactgcaaa taggggctat aaaagatcgg taccggaccc accttaaagc gggcgttcca    720
gatctccgca acttgttctt cgcggtcatg aataatttcg ctacctacca cgctccaggt    780
gtcagaaccc ggcagacagg aggtaaagct accgttatcc agaatggtat agcggttttc    840
gccacgttgt ttcatcaggt ccgctttacc gcgaccctgg cgaccacca tctggtaatc    900 accttcccag acgttggtat ctttggtgtt cagattcgcc cagcctttcg gccctttgag    960
gatcacctgg ttatcgtcgt aatggacatt accgagcgca tcaacaggtg ctgtagggaa   1020
acacgataga atccgaatta accttgccag caatatcagc accaacagaa aagcaat      1077

<210> SEQ ID NO 37
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 37 attgcuacttt gcctgtcgct ctatcttcta aggttaactt gtccagggtt tgtgtaacct     60
tcagcacctc actgcctggc cgtaaatacg cgtatcaaac ggaccaacat cattctggta    120
gtaattaacg tctaactgcg gctctgccga gtagctactg tgttctgtt cgctgaaaac    180 ctggaactgc ttggttgaaa cggtggcatt gaagttttgc accgcatagc caacgctgaa    240
tttttgcgtt gcgtagccgt cagtactgga accgtacttg ttatcgaaat cattgaagta    300
gctaggatcg ctgaccttgg tgtagtcgac gttgaaacgc cacacctgat ccatgacccc    360
ggagtggttc cagtagaata accaacgacg tgaactgtca tcgttcgggt gttcatcttc    420
atagacttta tctgaaggca gatagtccag ttccatcaag ccagcgcccg cctgggagag    480
gtagcggaat tcgttctccc acatgatgtt gccacgacga tgcatataat gcggcgtgat    540
ggtggcatcc atatttggcg cgatgttcca gtaatatggc aggtagaact caaagtagtt    600
ggtggtggtg tacttggcgt tcgggatcaa gaaaccagag cgacgtttgt cacccaccgg    660
caactgcaaa taggggctat aaaagatcgg taccggaccc accttaaagc gggcgttcca    720
gatctccgca acttgttctt cgcggtcatg aataatttcg ctacctacca cgctccaggt    780
gtcagaaccc ggcagacagg aggtaaagct accgttatcc agaatggtat agcggttttc    840
gccacgttgt ttcatcaggt ccgctttacc gcgaccctgg cgaccacca tctggtaatc    900
```

| | |
|---|---|
| accttcccag acgttggtat cttggtgtt cagattcgcc cagcctttcg gcccttgag | 960 |
| gatcacctgg ttatcgtcgt aatggacatt accgagcgca tcaacaggtg ctgaaggtta | 1020 |
| cacaaaccct ggacaagtta accttgccag caatatcagc accaacagaa aagcaat | 1077 |

```
<210> SEQ ID NO 38
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 38
```

| | |
|---|---|
| attgcuactt gcctgtcgct ctatcttcta aggttaattc tcgcaaaggc agaaagtagt | 60 |
| ccagcacctc actgcctggc cgtaaatacg cgtatcaaac ggaccaacat cattctggta | 120 |
| gtaattaacg tctaactgcg gctctgccga gtagctactg gtgttctgtt cgctgaaaac | 180 |
| ctggaactgc ttggttgaaa cggtggcatt gaagttttgc accgcatagc caacgctgaa | 240 |
| tttttgcgtt gcgtagccgt cagtactgga accgtacttg ttatcgaaat cattgaagta | 300 |
| gctaggatcg ctgaccttgg tgtagtcgac gttgaaacgc cacacctgat ccatgacccc | 360 |
| ggagtggttc cagtagaata accaacgacg tgaactgtca tcgttcgggt gttcatcttc | 420 |
| atagacttta tctgaaggca gatagtccag ttccatcaag ccagcgcccg cctgggagag | 480 |
| gtagcggaat tcgttctccc acatgatgtt gccacgacga tgcatataat gcggcgtgat | 540 |
| ggtggcatcc atatttggcg cgatgttcca gtaatatggc aggtagaact caaagtagtt | 600 |
| ggtggtggtg tacttggcgt tcgggatcaa gaaaccagag cgacgtttgt cacccaccgg | 660 |
| caactgcaaa taggggctat aaaagatcgg taccggaccc accttaaagc gggcgttcca | 720 |
| gatctccgca acttgttctt cgcggtcatg aataatttcg ctacctacca cgctccaggt | 780 |
| gtcagaaccc ggcagacagg aggtaaagct accgttatcc agaatggtat agcggttttc | 840 |
| gccacgttgt ttcatcaggt ccgctttacc gcgaccctgg cgacccacca tctggtaatc | 900 |
| accttcccag acgttggtat cttggtgtt cagattcgcc cagcctttcg gcccttgag | 960 |
| gatcacctgg ttatcgtcgt aatggacatt accgagcgca tcaacaggtg ctggactact | 1020 |
| ttctgccttt gcgagaatta accttgccag caatatcagc accaacagaa aagcaat | 1077 |

```
<210> SEQ ID NO 39
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 39
```

| | |
|---|---|
| attgcuactt gcctgtcgct ctatcttcta aggttaagtg ttaccgtggg aatgaatcct | 60 |
| tcagcacctc actgcctggc cgtaaatacg cgtatcaaac ggaccaacat cattctggta | 120 |
| gtaattaacg tctaactgcg gctctgccga gtagctactg gtgttctgtt cgctgaaaac | 180 |
| ctggaactgc ttggttgaaa cggtggcatt gaagttttgc accgcatagc caacgctgaa | 240 |
| tttttgcgtt gcgtagccgt cagtactgga accgtacttg ttatcgaaat cattgaagta | 300 |

```
gctaggatcg ctgaccttgg tgtagtcgac gttgaaacgc cacacctgat ccatgacccc    360
ggagtggttc cagtagaata accaacgacg tgaactgtca tcgttcgggt gttcatcttc    420
atagacttta tctgaaggca gatagtccag ttccatcaag ccagcgcccg cctgggagag    480
gtagcggaat tcgttctccc acatgatgtt gccacgacga tgcatataat gcggcgtgat    540
ggtggcatcc atatttggcg cgatgttcca gtaatatggc aggtagaact caaagtagtt    600
ggtggtggtg tacttggcgt tcgggatcaa gaaaccagag cgacgtttgt cacccaccgg    660
caactgcaaa tagggctat aaaagatcgg taccggaccc accttaaagc gggcgttcca    720
gatctccgca acttgttctt cgcggtcatg aataatttcg ctacctacca cgctccaggt    780
gtcagaaccc ggcagacagg aggtaaagct accgttatcc agaatggtat agcggttttc    840
gccacgttgt ttcatcaggt ccgctttacc gcgaccctgg cgaccacca tctggtaatc    900 accttcccag acgttggtat ctttggtgtt cagattcgcc cagcctttcg gccctttgag    960
gatcacctgg ttatcgtcgt aatggacatt accgagcgca tcaacaggtg ctgaaggatt   1020
cattcccacg gtaacactta accttgccag caatatcagc accaacagaa aagcaat     1077
```

```
<210> SEQ ID NO 40
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 40
```

```
attgcuactt gcctgtcgct ctatcttcta aggttaattc agggaacaaa ccaagttacg     60
tcagcacctc actgcctggc cgtaaatacg cgtatcaaac ggaccaacat cattctggta    120
gtaattaacg tctaactgcg gctctgccga gtagctactg gtgttctgtt cgctgaaaac    180
ctggaactgc ttggttgaaa cggtggcatt gaagttttgc accgcatagc caacgctgaa    240
tttttgcgtt gcgtagccgt cagtactgga accgtacttg ttatcgaaat cattgaagta    300
gctaggatcg ctgaccttgg tgtagtcgac gttgaaacgc cacacctgat ccatgacccc    360
ggagtggttc cagtagaata accaacgacg tgaactgtca tcgttcgggt gttcatcttc    420
atagacttta tctgaaggca gatagtccag ttccatcaag ccagcgcccg cctgggagag    480
gtagcggaat tcgttctccc acatgatgtt gccacgacga tgcatataat gcggcgtgat    540
ggtggcatcc atatttggcg cgatgttcca gtaatatggc aggtagaact caaagtagtt    600
ggtggtggtg tacttggcgt tcgggatcaa gaaaccagag cgacgtttgt cacccaccgg    660
caactgcaaa tagggctat aaaagatcgg taccggaccc accttaaagc gggcgttcca    720
gatctccgca acttgttctt cgcggtcatg aataatttcg ctacctacca cgctccaggt    780
gtcagaaccc ggcagacagg aggtaaagct accgttatcc agaatggtat agcggttttc    840
gccacgttgt ttcatcaggt ccgctttacc gcgaccctgg cgaccacca tctggtaatc    900 accttcccag acgttggtat ctttggtgtt cagattcgcc cagcctttcg gccctttgag    960
gatcacctgg ttatcgtcgt aatggacatt accgagcgca tcaacaggtg ctgacgtaac   1020
ttggtttgtt ccctgaatta accttgccag caatatcagc accaacagaa aagcaat     1077
```

```
<210> SEQ ID NO 41
```

```
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 41
attgcuactt gcctgtcgct ctatcttcta aggttaaaag aaagttgtcg gtgtctttgt      60
gcagcacctc aatgtaaccg ctaccaccgg taaccagaac tctcataatt cgctccatta     120
ggcttatggt atgaaataac catagcataa caaagatgcg aaaagtgtga catggaataa     180
attagtggaa tcgtttacac aagaatttag ccgtttttta tgcgcgatta agtgattata     240
aaacagaggg tttatgaatg attgcgcttt ttatctgaaa aaagacgcgg tttcatgcct     300
gcatgcgtcg aaccgttggc cggagagggt gctaaggccg cctccggcaa ggtcagcact     360
accgactcaa tatattttg tcagcacata gcgatagagt ccaccgtccg cacgaactc      420
aagacgatgg gtaatacagg caggcgcatc ttcagcgtgg tgcgaaacaa acaacaattg     480
cgtttcacct tcgctaatca gcacatcaac aaaacggcgg ataagctggc gattcagcgg     540
atcaagcccc tgtagtggtt catcgagaat aagcaacgtc ggatgtttca ccagtgcgcg     600
gacaatcagc gccagacgct gctgtcccca ggaaagacta tggaacgag cgtcagccgt      660
gcgtttatca atgccgagaa tatccagcca ctgctgcacc agttttgct ggcgatccga      720
aacggcctga taaatgccaa tcgaatcaaa atagccagaa agaatcacat acgcacggt      780
agtgctgacc cggtaatcca gatgcaaact actgctgacg taaccgatat gcttttgat      840
atcccagatg gtttcgccgc tgccgcgacg tcgtccgaaa agcgtcaaat cgttgctgta     900
accttgcgga tgatcgccag taaccaggct aataacgtc gattttcctg caccatttgg      960
cccgacaatt tgccagtgtt cgcctggatt cacctgccag ctaaggtagg tgctgcacaa    1020
agacaccgac aactttcttt taaccttgcc agcaatatca gcaccaacag aaaagcaat    1079

<210> SEQ ID NO 42
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 42
attgcuactt gcctgtcgct ctatcttcta aggttaatcg attccgtttg tagtcgtctg      60
tcagcacctc aatgtaaccg ctaccaccgg taaccagaac tctcataatt cgctccatta     120
ggcttatggt atgaaataac catagcataa caaagatgcg aaaagtgtga catggaataa     180
attagtggaa tcgtttacac aagaatttag ccgtttttta tgcgcgatta agtgattata     240
aaacagaggg tttatgaatg attgcgcttt ttatctgaaa aaagacgcgg tttcatgcct     300
gcatgcgtcg aaccgttggc cggagagggt gctaaggccg cctccggcaa ggtcagcact     360
accgactcaa tatattttg tcagcacata gcgatagagt ccaccgtccg cacgaactc      420
aagacgatgg gtaatacagg caggcgcatc ttcagcgtgg tgcgaaacaa acaacaattg     480
cgtttcacct tcgctaatca gcacatcaac aaaacggcgg ataagctggc gattcagcgg     540
```

```
atcaagcccc tgtagtggtt catcgagaat aagcaacgtc ggatgtttca ccagtgcgcg        600
gacaatcagc gccagacgct gctgtcccca ggaaagacta tggaacggag cgtcagccgt        660
gcgtttatca atgccgagaa tatccagcca ctgctgcacc agttttttgct ggcgatccga       720 aacggcctga taaatgccaa tcgaatcaaa atagccagaa agaatcacat tacgcacggt       780
agtgctgacc cggtaatcca gatgcaaact actgctgacg taaccgatat gcttttgat        840 atcccagatg gtttcgccgc tgccgcgacg tcgtccgaaa agcgtcaaat cgttgctgta       900
accttgcgga tgatcgccag taaccaggct taataacgtc gattttcctg caccatttgg       960
cccgacaatt tgccagtgtt cgcctggatt cacctgccag ctaaggtagg tgctgacaga      1020
cgactacaaa cggaatcgat taaccttgcc agcaatatca gcaccaacag aaaagcaat       1079
```

<210> SEQ ID NO 43
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 43

```
attgcuactt gcctgtcgct ctatcttcta aggttaagag tcttgtgtcc cagttaccag         60
gcagcacctc aatgtaaccg ctaccaccgg taaccagaac tctcataatt cgctccatta       120
ggcttatggt atgaaataac catagcataa caaagatgcg aaaagtgtga catggaataa       180
attagtggaa tcgtttacac aagaatttag ccgttttttta tgcgcgatta agtgattata     240
aaacagaggg tttatgaatg attgcgcttt ttatctgaaa aaagacgcgg tttcatgcct       300
gcatgcgtcg aaccgttggc cggagagggt gctaaggccg cctccggcaa ggtcagcact      360
accgactcaa tatattttg tcagcacata gcgatagagt ccaccgtccg gcacgaactc        420
aagacgatgg gtaatacagg caggcgcatc ttcagcgtgg tgcgaaacaa caacaattg       480 cgtttcacct tcgctaatca gcacatcaac aaaacggcgg ataagctggc gattcagcgg      540
atcaagcccc tgtagtggtt catcgagaat aagcaacgtc ggatgtttca ccagtgcgcg      600
gacaatcagc gccagacgct gctgtcccca ggaaagacta tggaacggag cgtcagccgt      660
gcgtttatca atgccgagaa tatccagcca ctgctgcacc agttttttgct ggcgatccga     720 aacggcctga taaatgccaa tcgaatcaaa atagccagaa agaatcacat tacgcacggt     780
agtgctgacc cggtaatcca gatgcaaact actgctgacg taaccgatat gcttttgat      840 atcccagatg gtttcgccgc tgccgcgacg tcgtccgaaa agcgtcaaat cgttgctgta     900
accttgcgga tgatcgccag taaccaggct taataacgtc gattttcctg caccatttgg    960
cccgacaatt tgccagtgtt cgcctggatt cacctgccag ctaaggtagg tgctgcctgg    1020
taactgggac acaagactct taaccttgcc agcaatatca gcaccaacag aaaagcaat     1079
```

<210> SEQ ID NO 44
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)

<223> OTHER INFORMATION: 5' Biotinylation

<400> SEQUENCE: 44

| | |
|---|---|
| attgcuactt gcctgtcgct ctatcttcta aggttaattc ggattctatc gtgtttccct | 60 |
| acagcacctc aatgtaaccg ctaccaccgg taaccagaac tctcataatt cgctccatta | 120 |
| ggcttatggt atgaaataac catagcataa caaagatgcg aaaagtgtga catggaataa | 180 |
| attagtggaa tcgtttacac aagaatttag ccgttttta tgcgcgatta agtgattata | 240 |
| aaacagaggg tttatgaatg attgcgcttt ttatctgaaa aagacgcgg tttcatgcct | 300 |
| gcatgcgtcg aaccgttggc cggagagggt gctaaggccg cctccggcaa ggtcagcact | 360 |
| accgactcaa tatattttg tcagcacata gcgatagagt ccaccgtccg gcacgaactc | 420 |
| aagacgatgg gtaatacagg caggcgcatc ttcagcgtgg tgcgaaacaa acaacaattg | 480 |
| cgtttcacct tcgctaatca gcacatcaac aaaacggcgg ataagctggc gattcagcgg | 540 |
| atcaagcccc tgtagtggtt catcgagaat aagcaacgtc ggatgtttca ccagtgcgcg | 600 |
| gacaatcagc gccagacgct gctgtcccca ggaaagacta tggaacggag cgtcagccgt | 660 |
| gcgtttatca atgccgagaa tatccagcca ctgctgcacc agtttttgct ggcgatccga | 720 |
| aacggcctga taaatgccaa tcgaatcaaa atagccagaa agaatcacat tacgcacggt | 780 |
| agtgctgacc cggtaatcca gatgcaaact actgctgacg taaccgatat gcttttgat | 840 |
| atcccagatg gtttcgccgc tgccgcgacg tcgtccgaaa agcgtcaaat cgttgctgta | 900 |
| accttgcgga tgatcgccag taaccaggct taataacgtc gattttcctg caccatttgg | 960 |
| cccgacaatt tgccagtgtt cgcctggatt cacctgccag ctaaggtagg tgctgtaggg | 1020 |
| aaacacgata gaatccgaat taaccttgcc agcaatatca gcaccaacag aaaagcaat | 1079 |

<210> SEQ ID NO 45
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 45

| | |
|---|---|
| attgcuactt gcctgtcgct ctatcttcta aggttaactt gtccagggtt tgtgtaacct | 60 |
| tcagcacctc aatgtaaccg ctaccaccgg taaccagaac tctcataatt cgctccatta | 120 |
| ggcttatggt atgaaataac catagcataa caaagatgcg aaaagtgtga catggaataa | 180 |
| attagtggaa tcgtttacac aagaatttag ccgttttta tgcgcgatta agtgattata | 240 |
| aaacagaggg tttatgaatg attgcgcttt ttatctgaaa aagacgcgg tttcatgcct | 300 |
| gcatgcgtcg aaccgttggc cggagagggt gctaaggccg cctccggcaa ggtcagcact | 360 |
| accgactcaa tatattttg tcagcacata gcgatagagt ccaccgtccg gcacgaactc | 420 |
| aagacgatgg gtaatacagg caggcgcatc ttcagcgtgg tgcgaaacaa acaacaattg | 480 |
| cgtttcacct tcgctaatca gcacatcaac aaaacggcgg ataagctggc gattcagcgg | 540 |
| atcaagcccc tgtagtggtt catcgagaat aagcaacgtc ggatgtttca ccagtgcgcg | 600 |
| gacaatcagc gccagacgct gctgtcccca ggaaagacta tggaacggag cgtcagccgt | 660 |
| gcgtttatca atgccgagaa tatccagcca ctgctgcacc agtttttgct ggcgatccga | 720 |
| aacggcctga taaatgccaa tcgaatcaaa atagccagaa agaatcacat tacgcacggt | 780 |

```
agtgctgacc cggtaatcca gatgcaaact actgctgacg taaccgatat gcttttgat      840 atcccagatg gtttcgccgc tgccgcgacg tcgtccgaaa agcgtcaaat cgttgctgta      900
accttgcgga tgatcgccag taaccaggct taataacgtc gattttcctg caccatttgg      960
cccgacaatt tgccagtgtt cgcctggatt cacctgccag ctaaggtagg tgctgaaggt     1020
tacacaaacc ctggacaagt taaccttgcc agcaatatca gcaccaacag aaaagcaat     1079
```

<210> SEQ ID NO 46
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 46

```
attgcuactt gcctgtcgct ctatcttcta aggttaattc tcgcaaaggc agaaagtagt       60
ccagcacctc aatgtaaccg ctaccaccgg taaccagaac tctcataatt cgctccatta      120
ggcttatggt atgaaataac catagcataa caaagatgcg aaaagtgtga catggaataa      180
attagtggaa tcgtttacac aagaatttag ccgtttttta tgcgcgatta agtgattata      240
aaacagaggg tttatgaatg attgcgcttt ttatctgaaa aaagacgcgg tttcatgcct      300
gcatgcgtcg aaccgttggc cggagagggt gctaaggccg cctccggcaa ggtcagcact      360
accgactcaa tatattttg tcagcacata gcgatagagt ccaccgtccg gcacgaactc      420
aagacgatgg gtaatacagg caggcgcatc ttcagcgtgg tgcgaaacaa caacaattg      480 cgtttcacct tcgctaatca gcacatcaac aaaacggcgg ataagctggc gattcagcgg      540
atcaagcccc tgtagtggtt catcgagaat aagcaacgtc ggatgtttca ccagtgcgcg      600
gacaatcagc gccagacgct gctgtcccca ggaaagacta tggaacggag cgtcagccgt      660
gcgtttatca atgccgagaa tatccagcca ctgctgcacc agttttgct ggcgatccga      720 aacggcctga taaatgccaa tcgaatcaaa atagccagaa agaatcacat tacgcacggt      780
agtgctgacc cggtaatcca gatgcaaact actgctgacg taaccgatat gcttttgat      840 atcccagatg gtttcgccgc tgccgcgacg tcgtccgaaa agcgtcaaat cgttgctgta      900
accttgcgga tgatcgccag taaccaggct taataacgtc gattttcctg caccatttgg      960
cccgacaatt tgccagtgtt cgcctggatt cacctgccag ctaaggtagg tgctggacta     1020
ctttctgcct ttgcgagaat taaccttgcc agcaatatca gcaccaacag aaaagcaat     1079
```

<210> SEQ ID NO 47
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 47

```
attgcuactt gcctgtcgct ctatcttcta aggttaagtg ttaccgtggg aatgaatcct       60
tcagcacctc aatgtaaccg ctaccaccgg taaccagaac tctcataatt cgctccatta      120
```

```
ggcttatggt atgaaataac catagcataa caaagatgcg aaaagtgtga catggaataa      180
attagtggaa tcgtttacac aagaatttag ccgttttta tgcgcgatta agtgattata      240
aaacagaggg tttatgaatg attgcgcttt ttatctgaaa aaagacgcgg tttcatgcct     300
gcatgcgtcg aaccgttggc cggagagggt gctaaggccg cctccggcaa ggtcagcact     360
accgactcaa tatattttg tcagcacata gcgatagagt ccaccgtccg gcacgaactc      420
aagacgatgg gtaatacagg caggcgcatc ttcagcgtgg tgcgaaacaa acaacaattg     480
cgtttcacct tcgctaatca gcacatcaac aaaacggcgg ataagctggc gattcagcgg     540
atcaagcccc tgtagtggtt catcgagaat aagcaacgtc ggatgtttca ccagtgcgcg     600
gacaatcagc gccagacgct gctgtcccca ggaaagacta tggaacggag cgtcagccgt     660
gcgtttatca atgccgagaa tatccagcca ctgctgcacc agttttttgct ggcgatccga    720 aacggcctga taaatgccaa tcgaatcaaa atagccagaa agaatcacat tacgcacggt     780
agtgctgacc cggtaatcca gatgcaaact actgctgacg taaccgatat gcttttgat    840 atcccagatg gtttcgccgc tgccgcgacg tcgtccgaaa agcgtcaaat cgttgctgta    900
accttgcgga tgatcgccag taaccaggct taataacgtc gattttcctg caccatttgg    960
cccgacaatt tgccagtgtt cgcctggatt cacctgccag ctaaggtagg tgctgaagga    1020
ttcattccca cggtaacact taaccttgcc agcaatatca gcaccaacag aaaagcaat     1079
```

<210> SEQ ID NO 48
<211> LENGTH: 1079
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 48

```
attgcuactt gcctgtcgct ctatcttcta aggttaattc agggaacaaa ccaagttacg       60
tcagcacctc aatgtaaccg ctaccaccgg taaccagaac tctcataatt cgctccatta     120
ggcttatggt atgaaataac catagcataa caaagatgcg aaaagtgtga catggaataa     180
attagtggaa tcgtttacac aagaatttag ccgttttta tgcgcgatta agtgattata     240
aaacagaggg tttatgaatg attgcgcttt ttatctgaaa aaagacgcgg tttcatgcct    300
gcatgcgtcg aaccgttggc cggagagggt gctaaggccg cctccggcaa ggtcagcact    360
accgactcaa tatattttg tcagcacata gcgatagagt ccaccgtccg gcacgaactc     420
aagacgatgg gtaatacagg caggcgcatc ttcagcgtgg tgcgaaacaa acaacaattg    480
cgtttcacct tcgctaatca gcacatcaac aaaacggcgg ataagctggc gattcagcgg    540
atcaagcccc tgtagtggtt catcgagaat aagcaacgtc ggatgtttca ccagtgcgcg    600
gacaatcagc gccagacgct gctgtcccca ggaaagacta tggaacggag cgtcagccgt    660
gcgtttatca atgccgagaa tatccagcca ctgctgcacc agttttttgct ggcgatccga   720 aacggcctga taaatgccaa tcgaatcaaa atagccagaa agaatcacat tacgcacggt    780
agtgctgacc cggtaatcca gatgcaaact actgctgacg taaccgatat gcttttgat   840 atcccagatg gtttcgccgc tgccgcgacg tcgtccgaaa agcgtcaaat cgttgctgta   900
accttgcgga tgatcgccag taaccaggct taataacgtc gattttcctg caccatttgg   960
cccgacaatt tgccagtgtt cgcctggatt cacctgccag ctaaggtagg tgctgacgta   1020
```

```
acttggtttg ttccctgaat taaccttgcc agcaatatca gcaccaacag aaaagcaat    1079
```

<210> SEQ ID NO 49
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 49

```
attgcuactt gcctgtcgct ctatcttcta aggttaaaag aaagttgtcg gtgtctttgt     60
gcagcaccta attaaacccg gctaccccac aaatcgtact catcggcgtg ctcgactttc    120
acacgcagga tatcacccgg cttaacgttg gtttcaccat tgagataaac cgcgccgtcg    180
atttccggtg catctgccat gctgcgacca atcgcgcctt cttcgtccac ttcgtcgata    240
atcaccagaa tttcacggcc cactttctct tgcaggcgct cggcggaaat ctgctgctgc    300
agctgcatga acggttcca gcgttcttct ttaacttctt ccggaacctg gtcaggcagg    360
gcattggcgt ctgcaccttc aaccgggctg tatttaaagc agccaacgcg atccagacgc    420
gcttctttca ggaagtcgag tagcatctgg aaatcttctt ctgtctcgcc agggaagccg    480
acaataaagg ttgagcgtag ggtcagttcc gggcagattt cgcgccactg tttgatgcgc    540
gccagttggc gatctacaga acccggacgc ttcatcagtt tgagaatgcg cgggctggcg    600
tgctgcaacg gaatgtccag atacggcagg attttgcctt ctgccatcag tgggatgacg    660
tcgtccacat gcggataagg gtaaacgtag tgcagacgtg tccagatccc cagtttcgat    720
aactgttcgc acaggctgac catgctggtt tttaccggct cgccgttgtg gaagccagta    780
cgatgtttaa catcaacgcc ataggcggaa gtatcctgcg agatcaccag aatctcttta    840
acgcccgcat ctaccagacg tttcgcttca cttaacactt cgccaatcgg acggctcacc    900
aggtcgccgc gcatagacgg aataatgcag aaggtgcagc ggtgattaca gccttcagaa    960
attttcagat aggcataatg acgcggcgtc agtttcacac cttgtaggtg ctgcacaaag   1020
acaccgacaa ctttctttta accttgccag caatatcagc accaacagaa aagcaat      1077
```

<210> SEQ ID NO 50
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 50

```
attgcuactt gcctgtcgct ctatcttcta aggttaatcg attccgtttg tagtcgtctg     60
tcagcaccta attaaacccg gctaccccac aaatcgtact catcggcgtg ctcgactttc    120
acacgcagga tatcacccgg cttaacgttg gtttcaccat tgagataaac cgcgccgtcg    180
atttccggtg catctgccat gctgcgacca atcgcgcctt cttcgtccac ttcgtcgata    240
atcaccagaa tttcacggcc cactttctct tgcaggcgct cggcggaaat ctgctgctgc    300
agctgcatga acggttcca gcgttcttct ttaacttctt ccggaacctg gtcaggcagg    360
```

```
gcattggcgt ctgcaccttc aaccgggctg tatttaaagc agccaacgcg atccagacgc    420
gcttctttca ggaagtcgag tagcatctgg aaatcttctt ctgtctcgcc agggaagccg    480
acaataaagg ttgagcgtag ggtcagttcc gggcagattt cgcgccactg tttgatgcgc    540
gccagttggc gatctacaga acccggacgc ttcatcagtt tgagaatgcg cgggctggcg    600
tgctgcaacg gaatgtccag atacggcagg attttgcctt ctgccatcag tgggatgacg    660
tcgtccacat gcggataagg gtaaacgtag tgcagacgtg tccagatccc cagtttcgat    720
aactgttcgc acaggctgac catgctggtt tttaccggct cgccgttgtg gaagccagta    780
cgatgtttaa catcaacgcc ataggcggaa gtatcctgcg agatcaccag aatctcttta    840
acgcccgcat ctaccagacg tttcgcttca cttaacactt cgccaatcgg acggctcacc    900
aggtcgccgc gcatagacgg aataatgcag aaggtgcagc ggtgattaca gccttcagaa    960
attttcagat aggcataatg acgcggcgtc agtttcacac cttgtaggtg ctgacagacg   1020
actacaaacg gaatcgatta accttgccag caatatcagc accaacagaa aagcaat     1077
```

<210> SEQ ID NO 51
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 51

```
attgcuactt gcctgtcgct ctatcttcta aggttaagag tcttgtgtcc cagttaccag     60
gcagcaccta attaaacccg gctacccccac aaatcgtact catcggcgtg ctcgactttc   120
acacgcagga tatcacccgg cttaacgttg gtttcaccat tgagataaac cgcgccgtcg    180
atttccggtg catctgccat gctgcgacca atcgcgcctt cttcgtccac ttcgtcgata    240
atcaccagaa tttcacggcc cactttctct tgcaggcgct cggcggaaat ctgctgctgc    300
agctgcatga acggttcca gcgttcttct ttaacttctt ccggaacctg gtcaggcagg    360
gcattggcgt ctgcaccttc aaccgggctg tatttaaagc agccaacgcg atccagacgc    420
gcttctttca ggaagtcgag tagcatctgg aaatcttctt ctgtctcgcc agggaagccg    480
acaataaagg ttgagcgtag ggtcagttcc gggcagattt cgcgccactg tttgatgcgc    540
gccagttggc gatctacaga acccggacgc ttcatcagtt tgagaatgcg cgggctggcg    600
tgctgcaacg gaatgtccag atacggcagg attttgcctt ctgccatcag tgggatgacg    660
tcgtccacat gcggataagg gtaaacgtag tgcagacgtg tccagatccc cagtttcgat    720
aactgttcgc acaggctgac catgctggtt tttaccggct cgccgttgtg gaagccagta    780
cgatgtttaa catcaacgcc ataggcggaa gtatcctgcg agatcaccag aatctcttta    840
acgcccgcat ctaccagacg tttcgcttca cttaacactt cgccaatcgg acggctcacc    900
aggtcgccgc gcatagacgg aataatgcag aaggtgcagc ggtgattaca gccttcagaa    960
attttcagat aggcataatg acgcggcgtc agtttcacac cttgtaggtg ctgcctggta   1020
actgggacac aagactctta accttgccag caatatcagc accaacagaa aagcaat     1077
```

<210> SEQ ID NO 52
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 52

```
attgcuactt gcctgtcgct ctatcttcta aggttaattc ggattctatc gtgtttccct    60
acagcaccta attaaacccg gctaccccac aaatcgtact catcggcgtg ctcgactttc   120
acacgcagga tatcacccgg cttaacgttg gtttcaccat tgagataaac cgcgccgtcg   180
atttccggtg catctgccat gctgcgacca atcgcgcctt cttcgtccac ttcgtcgata   240
atcaccagaa tttcacggcc cactttctct tgcaggcgct cggcggaaat ctgctgctgc   300
agctgcatga acggttcca gcgttcttct ttaacttctt ccggaacctg gtcaggcagg   360
gcattggcgt ctgcaccttc aaccgggctg tatttaaagc agccaacgcg atccagacgc   420
gcttctttca ggaagtcgag tagcatctgg aaatcttctt ctgtctcgcc agggaagccg   480
acaataaagg ttgagcgtag ggtcagttcc gggcagattt cgcgccactg tttgatgcgc   540
gccagttggc gatctacaga acccggacgc ttcatcagtt tgagaatgcg cgggctggcg   600
tgctgcaacg gaatgtccag atacggcagg attttgcctt ctgccatcag tgggatgacg   660
tcgtccacat gcggataagg gtaaacgtag tgcagacgtg tccagatccc cagtttcgat   720
aactgttcgc acaggctgac catgctggtt tttaccggct cgccgttgtg gaagccagta   780
cgatgtttaa catcaacgcc ataggcggaa gtatcctgcg agatcaccag aatctcttta   840
acgcccgcat ctaccagacg tttcgcttca cttaacactt cgccaatcgg acggctcacc   900
aggtcgccgc gcatagacgg aataatgcag aaggtgcagc ggtgattaca gccttcagaa   960
attttcagat aggcataatg acgcggcgtc agtttcacac cttgtaggtg ctgtagggaa  1020
acacgataga atccgaatta accttgccag caatatcagc accaacagaa aagcaat     1077
```

<210> SEQ ID NO 53
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 53

```
attgcuactt gcctgtcgct ctatcttcta aggttaactt gtccagggtt tgtgtaacct    60
tcagcaccta attaaacccg gctaccccac aaatcgtact catcggcgtg ctcgactttc   120
acacgcagga tatcacccgg cttaacgttg gtttcaccat tgagataaac cgcgccgtcg   180
atttccggtg catctgccat gctgcgacca atcgcgcctt cttcgtccac ttcgtcgata   240
atcaccagaa tttcacggcc cactttctct tgcaggcgct cggcggaaat ctgctgctgc   300
agctgcatga acggttcca gcgttcttct ttaacttctt ccggaacctg gtcaggcagg   360
gcattggcgt ctgcaccttc aaccgggctg tatttaaagc agccaacgcg atccagacgc   420
gcttctttca ggaagtcgag tagcatctgg aaatcttctt ctgtctcgcc agggaagccg   480
acaataaagg ttgagcgtag ggtcagttcc gggcagattt cgcgccactg tttgatgcgc   540
gccagttggc gatctacaga acccggacgc ttcatcagtt tgagaatgcg cgggctggcg   600
```

| | |
|---|---|
| tgctgcaacg gaatgtccag atacggcagg attttgcctt ctgccatcag tgggatgacg | 660 |
| tcgtccacat gcggataagg gtaaacgtag tgcagacgtg tccagatccc cagtttcgat | 720 |
| aactgttcgc acaggctgac catgctggtt tttaccggct cgccgttgtg gaagccagta | 780 |
| cgatgtttaa catcaacgcc ataggcggaa gtatcctgcg agatcaccag aatctcttta | 840 |
| acgcccgcat ctaccagacg tttcgcttca cttaacactt cgccaatcgg acggctcacc | 900 |
| aggtcgccgc gcatagacgg aataatgcag aaggtgcagc ggtgattaca gccttcagaa | 960 |
| attttcagat aggcataatg acgcggcgtc agtttcacac cttgtaggtg ctgaaggtta | 1020 |
| cacaaaccct ggacaagtta accttgccag caatatcagc accaacagaa aagcaat | 1077 |

<210> SEQ ID NO 54
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 54

| | |
|---|---|
| attgcuactt gcctgtcgct ctatcttcta aggttaattc tcgcaaaggc agaaagtagt | 60 |
| ccagcaccta attaaacccg gctacccac aaatcgtact catcggcgtg ctcgactttc | 120 |
| acacgcagga tatcacccgg cttaacgttg gtttcaccat tgagataaac cgcgccgtcg | 180 |
| atttccggtg catctgccat gctgcgacca atcgcgcctt cttcgtccac ttcgtcgata | 240 |
| atcaccagaa tttcacggcc cactttctct tgcaggcgct cggcggaaat ctgctgctgc | 300 |
| agctgcatga aacggttcca gcgttcttct ttaacttctt ccggaacctg gtcaggcagg | 360 |
| gcattggcgt ctgcaccttc aaccgggctg tatttaaagc agccaacgcg atccagacgc | 420 |
| gcttctttca ggaagtcgag tagcatctgg aaatcttctt ctgtctcgcc agggaagccg | 480 |
| acaataaagg ttgagcgtag ggtcagttcc gggcagattt cgcgccactg tttgatgcgc | 540 |
| gccagttggc gatctacaga acccggacgc ttcatcagtt tgagaatgcg cgggctggcg | 600 |
| tgctgcaacg gaatgtccag atacggcagg attttgcctt ctgccatcag tgggatgacg | 660 |
| tcgtccacat gcggataagg gtaaacgtag tgcagacgtg tccagatccc cagtttcgat | 720 |
| aactgttcgc acaggctgac catgctggtt tttaccggct cgccgttgtg gaagccagta | 780 |
| cgatgtttaa catcaacgcc ataggcggaa gtatcctgcg agatcaccag aatctcttta | 840 |
| acgcccgcat ctaccagacg tttcgcttca cttaacactt cgccaatcgg acggctcacc | 900 |
| aggtcgccgc gcatagacgg aataatgcag aaggtgcagc ggtgattaca gccttcagaa | 960 |
| attttcagat aggcataatg acgcggcgtc agtttcacac cttgtaggtg ctggactact | 1020 |
| ttctgccttt gcgagaatta accttgccag caatatcagc accaacagaa aagcaat | 1077 |

<210> SEQ ID NO 55
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 55

```
attgcuactt gcctgtcgct ctatcttcta aggttaagtg ttaccgtggg aatgaatcct      60
tcagcaccta attaaacccg gctacccaac aaatcgtact catcggcgtg ctcgactttc     120
acacgcagga tatcacccgg cttaacgttg gtttcaccat tgagataaac cgcgccgtcg     180
atttccggtg catctgccat gctgcgacca atcgcgcctt cttcgtccac ttcgtcgata     240
atcaccagaa tttcacggcc cactttctct tgcaggcgct cggcggaaat ctgctgctgc     300
agctgcatga acggttcca gcgttcttct ttaacttctt ccggaacctg gtcaggcagg      360
gcattggcgt ctgcaccttc aaccgggctg tatttaaagc agccaacgcg atccagacgc     420
gcttctttca ggaagtcgag tagcatctgg aaatcttctt ctgtctcgcc agggaagccg     480
acaataaagg ttgagcgtag ggtcagttcc gggcagattt cgcgccactg tttgatgcgc     540
gccagttggc gatctacaga acccggacgc ttcatcagtt tgagaatgcg cgggctggcg     600
tgctgcaacg gaatgtccag atacggcagg attttgcctt ctgccatcag tgggatgacg     660
tcgtccacat gcggataagg gtaaacgtag tgcagacgtg tccagatccc cagtttcgat     720
aactgttcgc acaggctgac catgctggtt tttaccggct cgccgttgtg gaagccagta     780
cgatgtttaa catcaacgcc ataggcggaa gtatcctgcg agatcaccag aatctcttta     840
acgcccgcat ctaccagacg tttcgcttca cttaacactt cgccaatcgg acggctcacc     900
aggtcgccgc gcatagacgg aataatgcag aaggtgcagc ggtgattaca gccttcagaa     960
attttcagat aggcataatg acgcggcgtc agtttcacac cttgtaggtg ctgaaggatt    1020
cattcccacg gtaacactta accttgccag caatatcagc accaacagaa aagcaat      1077
```

<210> SEQ ID NO 56
<211> LENGTH: 1077
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 56

```
attgcuactt gcctgtcgct ctatcttcta aggttaattc agggaacaaa ccaagttacg      60
tcagcaccta attaaacccg gctacccaac aaatcgtact catcggcgtg ctcgactttc     120
acacgcagga tatcacccgg cttaacgttg gtttcaccat tgagataaac cgcgccgtcg     180
atttccggtg catctgccat gctgcgacca atcgcgcctt cttcgtccac ttcgtcgata     240
atcaccagaa tttcacggcc cactttctct tgcaggcgct cggcggaaat ctgctgctgc     300
agctgcatga acggttcca gcgttcttct ttaacttctt ccggaacctg gtcaggcagg      360
gcattggcgt ctgcaccttc aaccgggctg tatttaaagc agccaacgcg atccagacgc     420
gcttctttca ggaagtcgag tagcatctgg aaatcttctt ctgtctcgcc agggaagccg     480
acaataaagg ttgagcgtag ggtcagttcc gggcagattt cgcgccactg tttgatgcgc     540
gccagttggc gatctacaga acccggacgc ttcatcagtt tgagaatgcg cgggctggcg     600
tgctgcaacg gaatgtccag atacggcagg attttgcctt ctgccatcag tgggatgacg     660
tcgtccacat gcggataagg gtaaacgtag tgcagacgtg tccagatccc cagtttcgat     720
aactgttcgc acaggctgac catgctggtt tttaccggct cgccgttgtg gaagccagta     780
cgatgtttaa catcaacgcc ataggcggaa gtatcctgcg agatcaccag aatctcttta     840
```

```
acgcccgcat ctaccagacg tttcgcttca cttaacactt cgccaatcgg acggctcacc    900
aggtcgccgc gcatagacgg aataatgcag aaggtgcagc ggtgattaca gccttcagaa    960
attttcagat aggcataatg acgcggcgtc agtttcacac cttgtaggtg ctgacgtaac   1020
ttggtttgtt ccctgaatta accttgccag caatatcagc accaacagaa aagcaat     1077
```

```
<210> SEQ ID NO 57
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 57
attgcuactt gcctgtcgct ctatcttcta aggttaaaag aaagttgtcg gtgtctttgt     60
gcagcacctg atggtgaccg gcattcttcc gctgttgatt agcctgctgg ttatcatgaa    120
cgcactgatt aattttatcg gtcagcatcg tattgaacgt tttgctcaac gttgcgccgg    180
taaccctgtt tcccgttacc tactgttacc gtgcattggc acgtttgtct tttgcaatcc    240
gatgacccta agcctgggtc gctttatgcc ggaaaagtac aaacccagct actacgcggc    300
ggcctcttat agctgccact caatgaatgg cctcttcccc catatcaacc ctggcgaact    360
gtttgtttat cttggcattg ccagcggtct gacaacgctg aacctgccac ttggcccact    420
ggcggtgagt tatctgctgg ttggtctggt caccaatttc ttccgcggct gggtgaccga    480
tctgaccacc gccattttg agaaaaagat gggcattcaa cttgaacaaa aagttcacct    540
ggcaggagca acatcatgac gcatattcgg atcgaaaaag gaacgggtgg ctggggcggc    600
ccgcttgagc tgaaagccac gccgggaaaa aaatcgtct atatcaccgc cggtacccgg    660
cctgcgattg ttgacaaact ggcacagctt actggctggc aggctattga cggatttaaa    720
gaaggtgaac ccgcggaggc ggaaattggt gtcgcggtaa tcgactgtgg cggcacatta    780
cgctgcggca tctatccgaa acgacgtatt cccaccatta atatccactc gacgggcaag    840
tccggtccgc tggcgcagta cattgtggaa gatatttatg tctctggcgt aaaagaagaa    900
aacatcactg tagtaggtga tgcgacacca caaccctctt ccgtgggccg tgactatgac    960
accagtaaga aaatcaccga acaaagcgat ggtttactgg cgaaggaggt gctgcacaaa   1020
gacaccgaca actttctttt aaccttgcca gcaatatcag caccaacaga aaagcaat    1078
```

```
<210> SEQ ID NO 58
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 58
attgcuactt gcctgtcgct ctatcttcta aggttaatcg attccgtttg tagtcgtctg     60
tcagcacctg atggtgaccg gcattcttcc gctgttgatt agcctgctgg ttatcatgaa    120
cgcactgatt aattttatcg gtcagcatcg tattgaacgt tttgctcaac gttgcgccgg    180
taaccctgtt tcccgttacc tactgttacc gtgcattggc acgtttgtct tttgcaatcc    240
```

```
gatgacccta agcctgggtc gctttatgcc ggaaaagtac aaacccagct actacgcggc    300
ggcctcttat agctgccact caatgaatgg cctcttcccc catatcaacc ctggcgaact    360
gtttgtttat cttggcattg ccagcggtct gacaacgctg aacctgccac ttggcccact    420
ggcggtgagt tatctgctgg ttggtctggt caccaatttc ttccgcgcgct gggtgaccga    480 tctgaccacc gccattttg agaaaaagat gggcattcaa cttgaacaaa aagttcacct    540
ggcaggagca acatcatgac gcatattcgg atcgaaaaag gaacgggtgg ctggggcggc    600
ccgcttgagc tgaaagccac gccgggaaaa aaaatcgtct atatcaccgc cggtacccgg    660
cctgcgattg ttgacaaact ggcacagctt actggctggc aggctattga cggatttaaa    720
gaaggtgaac ccgcggaggc ggaaattggt gtcgcggtaa tcgactgtgg cggcacatta    780
cgctgcggca tctatccgaa acgacgtatt cccaccatta atatccactc gacgggcaag    840
tccggtccgc tggcgcagta cattgtggaa gatatttatg tctctggcgt aaaagaagaa    900
aacatcactg tagtaggtga tgcgacacca caaccctctt ccgtgggccg tgactatgac    960
accagtaaga aaatcaccga acaaagcgat ggtttactgg cgaaggaggt gctgacagac   1020
gactacaaac ggaatcgatt aaccttgcca gcaatatcag caccaacaga aaagcaat    1078
```

<210> SEQ ID NO 59
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 59

```
attgcuactt gcctgtcgct ctatcttcta aggttaagag tcttgtgtcc cagttaccag     60
gcagcacctg atggtgaccg gcattcttcc gctgttgatt agcctgctgg ttatcatgaa    120
cgcactgatt aattttatcg gtcagcatcg tattgaacgt tttgctcaac gttgcgccgg    180
taaccctgtt tcccgttacc tactgttacc gtgcattggc acgtttgtct tttgcaatcc    240
gatgacccta agcctgggtc gctttatgcc ggaaaagtac aaacccagct actacgcggc    300
ggcctcttat agctgccact caatgaatgg cctcttcccc catatcaacc ctggcgaact    360
gtttgtttat cttggcattg ccagcggtct gacaacgctg aacctgccac ttggcccact    420
ggcggtgagt tatctgctgg ttggtctggt caccaatttc ttccgcgcgct gggtgaccga    480 tctgaccacc gccattttg agaaaaagat gggcattcaa cttgaacaaa aagttcacct    540
ggcaggagca acatcatgac gcatattcgg atcgaaaaag gaacgggtgg ctggggcggc    600
ccgcttgagc tgaaagccac gccgggaaaa aaaatcgtct atatcaccgc cggtacccgg    660
cctgcgattg ttgacaaact ggcacagctt actggctggc aggctattga cggatttaaa    720
gaaggtgaac ccgcggaggc ggaaattggt gtcgcggtaa tcgactgtgg cggcacatta    780
cgctgcggca tctatccgaa acgacgtatt cccaccatta atatccactc gacgggcaag    840
tccggtccgc tggcgcagta cattgtggaa gatatttatg tctctggcgt aaaagaagaa    900
aacatcactg tagtaggtga tgcgacacca caaccctctt ccgtgggccg tgactatgac    960
accagtaaga aaatcaccga acaaagcgat ggtttactgg cgaaggaggt gctgcctggt   1020
aactgggaca caagactctt aaccttgcca gcaatatcag caccaacaga aaagcaat    1078
```

<210> SEQ ID NO 60
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 60

```
attgcuactt gcctgtcgct ctatcttcta aggttaattc ggattctatc gtgtttccct      60
acagcacctg atggtgaccg gcattcttcc gctgttgatt agcctgctgg ttatcatgaa     120
cgcactgatt aattttatcg gtcagcatcg tattgaacgt tttgctcaac gttgcgccgg     180
taaccctgtt tcccgttacc tactgttacc gtgcattggc acgtttgtct tttgcaatcc     240
gatgacccta agcctgggtc gctttatgcc ggaaaagtac aaacccagct actacgcggc     300
ggcctcttat agctgccact caatgaatgg cctcttcccc catatcaacc ctggcgaact     360
gtttgtttat cttggcattg ccagcggtct gacaacgctg aacctgccac ttggcccact     420
ggcggtgagt tatctgctgg ttggtctggt caccaatttc ttccgcggct gggtgaccga     480
tctgaccacc gccattttg agaaaaagat gggcattcaa cttgaacaaa agttcacct      540
ggcaggagca acatcatgac gcatattcgg atcgaaaaag gaacgggtgg ctggggcggc     600
ccgcttgagc tgaaagccac gccgggaaaa aaatcgtct atatcaccgc cggtacccgg     660
cctgcgattg ttgacaaact ggcacagctt actggctggc aggctattga cggatttaaa     720
gaaggtgaac ccgcggaggc ggaaattggt gtcgcggtaa tcgactgtgg cggcacatta     780
cgctgcggca tctatccgaa acgacgtatt cccaccatta atatccactc gacgggcaag     840
tccggtccgc tggcgcagta cattgtggaa gatatttatg tctctggcgt aaaagaagaa     900
aacatcactg tagtaggtga tgcgacacca caaccctctt ccgtgggccg tgactatgac     960
accagtaaga aaatcaccga acaaagcgat ggtttactgg cgaaggaggt gctgtaggga    1020
aacacgatag aatccgaatt aaccttgcca gcaatatcag caccaacaga aaagcaat     1078
```

<210> SEQ ID NO 61
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 61

```
attgcuactt gcctgtcgct ctatcttcta aggttaactt gtccagggtt tgtgtaacct      60
tcagcacctg atggtgaccg gcattcttcc gctgttgatt agcctgctgg ttatcatgaa     120
cgcactgatt aattttatcg gtcagcatcg tattgaacgt tttgctcaac gttgcgccgg     180
taaccctgtt tcccgttacc tactgttacc gtgcattggc acgtttgtct tttgcaatcc     240
gatgacccta agcctgggtc gctttatgcc ggaaaagtac aaacccagct actacgcggc     300
ggcctcttat agctgccact caatgaatgg cctcttcccc catatcaacc ctggcgaact     360
gtttgtttat cttggcattg ccagcggtct gacaacgctg aacctgccac ttggcccact     420
ggcggtgagt tatctgctgg ttggtctggt caccaatttc ttccgcggct gggtgaccga     480
```

-continued

| | |
|---|---|
| tctgaccacc gccattttg agaaaaagat gggcattcaa cttgaacaaa aagttcacct | 540 |
| ggcaggagca acatcatgac gcatattcgg atcgaaaaag gaacgggtgg ctggggcggc | 600 |
| ccgcttgagc tgaaagccac gccgggaaaa aaaatcgtct atatcaccgc cggtacccgg | 660 |
| cctgcgattg ttgacaaact ggcacagctt actggctggc aggctattga cggatttaaa | 720 |
| gaaggtgaac ccgcggaggc ggaaattggt gtcgcggtaa tcgactgtgg cggcacatta | 780 |
| cgctgcggca tctatccgaa acgacgtatt cccaccatta atatccactc gacgggcaag | 840 |
| tccggtccgc tggcgcagta cattgtggaa gatatttatg tctctggcgt aaaagaagaa | 900 |
| aacatcactg tagtaggtga tgcgacacca caaccctctt ccgtgggccg tgactatgac | 960 |
| accagtaaga aaatcaccga acaaagcgat ggtttactgg cgaaggaggt gctgaaggtt | 1020 |
| acacaaaccc tggacaagtt aaccttgcca gcaatatcag caccaacaga aaagcaat | 1078 |

<210> SEQ ID NO 62
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 62

| | |
|---|---|
| attgcuactt gcctgtcgct ctatcttcta aggttaattc tcgcaaaggc agaaagtagt | 60 |
| ccagcacctg atggtgaccg gcattcttcc gctgttgatt agcctgctgg ttatcatgaa | 120 |
| cgcactgatt aattttatcg gtcagcatcg tattgaacgt tttgctcaac gttgcgccgg | 180 |
| taaccctgtt tcccgttacc tactgttacc gtgcattggc acgtttgtct tttgcaatcc | 240 |
| gatgacccta agcctgggtc gctttatgcc ggaaaagtac aaacccagct actacgcggc | 300 |
| ggcctcttat agctgccact caatgaatgg cctcttcccc catatcaacc ctggcgaact | 360 |
| gtttgtttat cttggcattg ccagcggtct gacaacgctg aacctgccac ttggcccact | 420 |
| ggcggtgagt tatctgctgg ttggtctggt caccaatttc ttccgcggct gggtgaccga | 480 |
| tctgaccacc gccattttg agaaaaagat gggcattcaa cttgaacaaa aagttcacct | 540 |
| ggcaggagca acatcatgac gcatattcgg atcgaaaaag gaacgggtgg ctggggcggc | 600 |
| ccgcttgagc tgaaagccac gccgggaaaa aaaatcgtct atatcaccgc cggtacccgg | 660 |
| cctgcgattg ttgacaaact ggcacagctt actggctggc aggctattga cggatttaaa | 720 |
| gaaggtgaac ccgcggaggc ggaaattggt gtcgcggtaa tcgactgtgg cggcacatta | 780 |
| cgctgcggca tctatccgaa acgacgtatt cccaccatta atatccactc gacgggcaag | 840 |
| tccggtccgc tggcgcagta cattgtggaa gatatttatg tctctggcgt aaaagaagaa | 900 |
| aacatcactg tagtaggtga tgcgacacca caaccctctt ccgtgggccg tgactatgac | 960 |
| accagtaaga aaatcaccga acaaagcgat ggtttactgg cgaaggaggt gctggactac | 1020 |
| tttctgcctt tgcgagaatt aaccttgcca gcaatatcag caccaacaga aaagcaat | 1078 |

<210> SEQ ID NO 63
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:

<221> NAME/KEY: misc_feature
<222> LOCATION: (1)..(1)
<223> OTHER INFORMATION: 5' Biotinylation

<400> SEQUENCE: 63

```
attgcuactt gcctgtcgct ctatcttcta aggttaagtg ttaccgtggg aatgaatcct    60
tcagcacctg atggtgaccg gcattcttcc gctgttgatt agcctgctgg ttatcatgaa   120
cgcactgatt aattttatcg gtcagcatcg tattgaacgt tttgctcaac gttgcgccgg   180
taaccctgtt tcccgttacc tactgttacc gtgcattggc acgtttgtct tttgcaatcc   240
gatgacccta agcctgggtc gctttatgcc ggaaaagtac aaacccagct actacgcggc   300
ggcctcttat agctgccact caatgaatgg cctcttcccc catatcaacc ctggcgaact   360
gtttgtttat cttggcattg ccagcggtct gacaacgctg aacctgccac ttggcccact   420
ggcggtgagt tatctgctgg ttggtctggt caccaatttc ttccgcggct gggtgaccga   480
tctgaccacc gccattttg agaaaaagat gggcattcaa cttgaacaaa aagttcacct   540
ggcaggagca acatcatgac gcatattcgg atcgaaaaag gaacgggtgg ctggggcggc   600
ccgcttgagc tgaaagccac gccgggaaaa aaatcgtct atatcaccgc cggtacccgg   660
cctgcgattg ttgacaaact ggcacagctt actggctggc aggctattga cggatttaaa   720
gaaggtgaac ccgcggaggc ggaaattggt gtcgcggtaa tcgactgtgg cggcacatta   780
cgctgcggca tctatccgaa acgacgtatt cccaccatta atatccactc gacgggcaag   840
tccggtccgc tggcgcagta cattgtggaa gatatttatg tctctggcgt aaaagaagaa   900
aacatcactg tagtaggtga tgcgacacca caaccctctt ccgtgggccg tgactatgac   960
accagtaaga aaatcaccga acaaagcgat ggtttactgg cgaaggaggt gctgaaggat  1020
tcattcccac ggtaacactt aaccttgcca gcaatatcag caccaacaga aaagcaat   1078
```

<210> SEQ ID NO 64
<211> LENGTH: 1078
<212> TYPE: DNA
<213> ORGANISM: Artificial Sequence
<220> FEATURE:
<223> OTHER INFORMATION: Synthetic reporter polynucleotide
<220> FEATURE:
<221> NAME/KEY: misc_feature
<222> LOCATION: (1)..(1)
<223> OTHER INFORMATION: 5' Biotinylation

<400> SEQUENCE: 64

```
attgcuactt gcctgtcgct ctatcttcta aggttaattc agggaacaaa ccaagttacg    60
tcagcacctg atggtgaccg gcattcttcc gctgttgatt agcctgctgg ttatcatgaa   120
cgcactgatt aattttatcg gtcagcatcg tattgaacgt tttgctcaac gttgcgccgg   180
taaccctgtt tcccgttacc tactgttacc gtgcattggc acgtttgtct tttgcaatcc   240
gatgacccta agcctgggtc gctttatgcc ggaaaagtac aaacccagct actacgcggc   300
ggcctcttat agctgccact caatgaatgg cctcttcccc catatcaacc ctggcgaact   360
gtttgtttat cttggcattg ccagcggtct gacaacgctg aacctgccac ttggcccact   420
ggcggtgagt tatctgctgg ttggtctggt caccaatttc ttccgcggct gggtgaccga   480
tctgaccacc gccattttg agaaaaagat gggcattcaa cttgaacaaa aagttcacct   540
ggcaggagca acatcatgac gcatattcgg atcgaaaaag gaacgggtgg ctggggcggc   600
ccgcttgagc tgaaagccac gccgggaaaa aaatcgtct atatcaccgc cggtacccgg   660
cctgcgattg ttgacaaact ggcacagctt actggctggc aggctattga cggatttaaa   720
```

```
gaaggtgaac ccgcggaggc ggaaattggt gtcgcggtaa tcgactgtgg cggcacatta    780
cgctgcggca tctatccgaa acgacgtatt cccaccatta atatccactc gacgggcaag    840
tccggtccgc tggcgcagta cattgtggaa gatatttatg tctctggcgt aaaagaagaa    900
aacatcactg tagtaggtga tgcgacacca caaccctctt ccgtgggccg tgactatgac    960
accagtaaga aaatcaccga acaaagcgat ggtttactgg cgaaggaggt gctgacgtaa   1020
cttggtttgt tccctgaatt aaccttgcca gcaatatcag caccaacaga aaagcaat    1078
```